(12) United States Patent
Mazur et al.

(10) Patent No.: US 7,087,759 B2
(45) Date of Patent: Aug. 8, 2006

(54) MELANOCORTIN RECEPTOR LIGANDS

(75) Inventors: Wieslaw Adam Mazur, Mason, OH (US); Xinrong Tian, Mason, OH (US); Xiufeng Eric Hu, Cincinnati, OH (US); Frank Hallock Ebetino, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 94 days.

(21) Appl. No.: 10/856,983

(22) Filed: May 28, 2004

(65) Prior Publication Data

US 2004/0224985 A1    Nov. 11, 2004

Related U.S. Application Data

(62) Division of application No. 10/121,874, filed on Apr. 12, 2002, now Pat. No. 6,911,447.

(60) Provisional application No. 60/286,610, filed on Apr. 25, 2001.

(51) Int. Cl.
*C07D 261/20* (2006.01)
*C07D 211/36* (2006.01)
*C07D 207/48* (2006.01)
*A61K 31/445* (2006.01)

(52) U.S. Cl. ............... 546/242; 514/315; 514/423; 514/424; 548/540; 548/530

(58) Field of Classification Search ........ 514/315, 514/423, 424; 546/242; 548/540, 530
See application file for complete search history.

(56) References Cited

U.S. PATENT DOCUMENTS

| | | |
|---|---|---|
| 5,492,916 A | 2/1996 | Morriello et al. |
| 5,494,919 A | 2/1996 | Morriello et al. |
| 5,536,716 A | 7/1996 | Chen et al. |
| 5,721,250 A | 2/1998 | Morriello et al. |
| 5,721,251 A | 2/1998 | Chen et al. |
| 5,741,792 A * | 4/1998 | Kimball et al. ......... 514/237.2 |
| 5,741,799 A * | 4/1998 | Kimball et al. ........... 514/316 |
| 5,783,582 A | 7/1998 | Guo et al. |
| 5,804,578 A | 9/1998 | Chakravarty et al. |
| 5,877,182 A | 3/1999 | Nargund et al. |
| 5,880,125 A | 3/1999 | Nargund |
| 5,936,089 A | 8/1999 | Carpino et al. |
| 5,965,565 A | 10/1999 | Chen et al. |
| 6,294,534 B1 | 9/2001 | Nargund et al. |
| 6,350,760 B1 | 2/2002 | Bakshi et al. |
| 6,534,536 B1 * | 3/2003 | Kimball et al. ............ 514/423 |
| 6,713,487 B1 * | 3/2004 | Yu et al. ..................... 514/278 |

FOREIGN PATENT DOCUMENTS

| | | |
|---|---|---|
| WO | WO 94/13696 A1 | 6/1994 |
| WO | WO 94/19367 A1 | 9/1994 |
| WO | WO 96/02530 A1 | 2/1996 |
| WO | WO 96/13265 A1 | 5/1996 |
| WO | WO 96/38471 A1 | 12/1996 |
| WO | WO 98/10653 A1 | 3/1998 |
| WO | WO 99/55679 A1 | 11/1999 |
| WO | WO 99/58501 A1 | 11/1999 |
| WO | WO 99/64002 A1 | 12/1999 |
| WO | WO 00/74679 A1 | 12/2000 |
| WO | WO 01/70337 A1 | 9/2001 |
| WO | WO 01/70708 A1 | 9/2001 |
| WO | WO 01/91752 A1 | 12/2001 |
| WO | WO 02/00654 A1 | 1/2002 |
| WO | WO 02/15909 A1 | 2/2002 |
| WO | WO 02/59107 A1 | 8/2002 |
| WO | WO 02/59117 A1 | 8/2002 |
| WO | WO 02/68387 A2 | 9/2002 |
| WO | WO 02/68388 A2 | 9/2002 |
| WO | WO 02/70511 A1 | 9/2002 |
| WO | WO 03/031410 A1 | 4/2003 |

* cited by examiner

*Primary Examiner*—D. Margaret Seaman
(74) *Attorney, Agent, or Firm*—Richard S. Echler, Sr.

(57) ABSTRACT

Disclosed are MC-3/MC-4 receptor ligands, the ligands having the following formula:

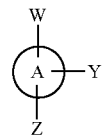

wherein A is a conformationally restricted ring system selected from the group consisting of:
a) non-aromatic carbocyclic rings;
b) aromatic carbocyclic rings;
c) non-aromatic heterocyclic rings;
d) aromatic heterocyclic rings;
wherein said rings comprises from 5 to 8 atoms; and W is a unit which preferable comprises D-1-fluorophenylalanine, Y comprises a heteroatom, and Z comprises an aromatic carbocyclic ring. Also disclosed are pharmaceutical compositions comprising the ligands of the invention as well as methods of treating diseases mediated through MC-3/MC-4 receptors.

15 Claims, No Drawings

MELANOCORTIN RECEPTOR LIGANDS

CROSS REFERENCE TO RELATED APPLICATIONS

This application is a Divisional Application of application Ser. No. 10/121,874 filed Apr. 12, 2002 now U.S. Pat. No. 6,911,447 which claims priority under Title 35, United States Code 119(e) from Provisional Application Ser. No. 60/286,610 filed Apr. 25, 2001.

FIELD OF THE INVENTION

The present invention relates to melanocortin (MC) receptor ligands that have a conformationally restricted ring element, which provides for enhanced activity. These ligands preferably exhibit selectivity for the MC-3 and/or MC-4 receptors relative to the other melanocortin receptors (in particular the MC-1 receptor) and are suitable for use in pharmaceutical compositions and in treatment methods.

BACKGROUND OF THE INVENTION

Melanocortin peptides (melanocortins) are natural peptide hormones in animals and man that bind to and stimulate MC receptors. Examples of melanocortins are α-MSH (melanocyte stimulating hormone), β-MSH, γ-MSH, ACTH (adrenocorticotropic hormone) and their peptide fragments. MSH is mainly known for its ability to regulate peripheral pigmentation, whereas ACTH is known to induce steroidoneogenesis. The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as other events related to parturition.

Both the MC-4 and MC-3 receptors have been localized to the hypothalamus, a region of the brain believed to be involved in the modulation of feeding behavior. Compounds showing selectivity for the MC-3/MC-4 receptors have been shown to alter food intake following intracerebroventricular and peripheral injection in rodents. Specifically, agonists have been shown to reduce feeding, while antagonists have been shown to increase feeding. The role of the MC-4 and MC-3 receptors have been defined in the control of body weight regulation in mammals. It is believed that the MC-3 receptor influences feeding efficiency and the partitioning of fuel stores into fat, whereas the MC-4 receptor regulates food intake and possibly energy expenditure. Thus, these receptor subtypes appear to reduce body weight through distinct and complementary pathways. Therefore compounds that stimulate both the MC-3 and MC-4 receptors may have a greater weight loss effect than those that are selective for either the MC-3 or MC-4 receptor.

Body weight disorders such as obesity, anorexia and cachexia are widely recognized as significant public health issues and there is a need for compounds and pharmaceutical compositions, which can treat these disorders.

The Applicants have discovered a class of compounds that surprisingly have high affinity for the MC-4 and/or the MC-3 receptor subtypes, and that are typically selective for these MC receptors relative to the other melanocortin receptor subtypes, particularly the MC-1 subtype.

SUMMARY OF THE INVENTION

The present invention relates to a class of compounds that are ligands for MC-3 and/or MC-4 receptors and comprise a 5–8 atom ring, which conformationally restricts the orientation of the three pendant units.

The compounds of the present invention include all enantiomeric and diasteriomeric forms and pharmaceutically acceptable salts thereof, said compounds having the formula:

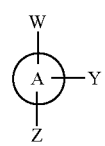

wherein A is a conformationally restricted ring system selected from the group consisting of:
a) non-aromatic carbocyclic rings;
b) aromatic carbocyclic rings;
c) non-aromatic heterocyclic rings;
d) aromatic heterocyclic rings;

wherein said rings comprises from 5 to 8 atoms;

W is a pendant unit having the formula:

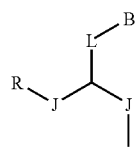

wherein R is selected from the group consisting of:
a) non-aromatic carbocyclic rings;
b) aromatic carbocyclic rings;
c) non-aromatic heterocyclic rings;
d) aromatic heterocyclic rings;

said rings comprising from 3 to 12 atoms;

J is selected from the group consisting of:
i) —[C(R")$_d$]$_k$—; wherein each R" is independently hydrogen, $C_1$–$C_{12}$ linear or branched alkyl, -SUB, two R" units can be taken together with an oxygen atom to form a carbonyl unit, two R" units from any J units or an R" unit and an R' unit. from a T unit can be taken together to form a carbocyclic or heterocyclic fused ring, bicyclo ring, or spiroannulated ring comprising from 3 to 7 atoms; the index d has the value of 1 or 2; the index k has the value of 1 or 2;
ii)

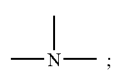

iii) —NR'—; wherein R' is hydrogen, $C_1$–$C_6$ linear or branched alkyl, or a SUB unit;
iv) —O—;

v) —S—;
vi) —P(O)— or —P(O)$_2$—;
vii) and mixtures thereof.

L is a suitable linking unit;

B comprises a unit selected from the group consisting of:
  a) hydrogen;
  b) substituted or unsubstituted aromatic carbocyclic rings;
  c) substituted or unsubstituted aromatic heterocyclic rings; and
  d) mixtures thereof;

Y is a pendant unit comprising at least one heteroatom;

Z is a pendant unit, which comprises an aromatic ring or non-aromatic ring moiety.

The present invention further relates to pharmaceutical compositions comprising the herein described MC3 and/or MC4 receptor ligands, said ligands having a high affinity and selectivity for the MC3 and/or MC4 receptor subtypes over the MCl receptor subtype.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to receptor ligands. The melanocortin (MC) class of peptides mediates a wide range of physiological effects. Synthetic peptides and peptide mimetics, which modulate the interaction of natural MC ligands have varying degrees of selectivity and binding. The present invention is directed to ligands that are selective for the MC4 receptor, or that are selective for both the MC4 and MC3 receptor while minimizing the interaction at the MC1, MC2, and MC5 receptors.

It has been surprisingly discovered that conformationally restricting the rotation along a key peptide linkage provides receptor ligands having increased selectivity and binding. Key to the present invention is the discovery that the conformationally restricted structure can comprise structural isosteres in several embodiments, inter alia, 5-member rings and 6-member rings as well as chemical bonds, which simply restrict the rotation of the normal peptide link.

Although not wishing to be limited by theory, once the peptide or peptide mimetic rotation is fixed, the resulting appended moieties begin to differentiate between themselves as it relates to their physiological and biological functions. The appending units or moieties from the core ring structure are herein described as "W pendant units" or "units," "Y pendant units" or "units having a base moiety, a quaternary nitrogen moiety, or mixtures thereof," and "Z pendant units." The units are so named to assist not only in differentiating their prospective functionality, but also as mnemonic devices to assist the formulator in conceptualizing the scope and embodiments described herein. Therefore, units conveniently described as units (W pendant units) may play one or more other roles in eliciting the desired physiological and biological response. The scope of the present invention is not limited by this need to differentiate the appendages for the sake of clearly defining the metes and bound of each group, unit, or moiety.

As it relates to the term "amino acid", those of ordinary skill in the art will recognize this term to mean the naturally occurring constituent elements of peptides, enzymes, and the like, as well as non-naturally occurring variants. The following is a non-limiting list of common amino acids together with their abbreviation and single letter codes: alanine (Ala, A); arginine (Arg; R); asparagines (Asp; N); aspartic acid (Asp, D); cysteine (Cys, C); glutamic acid (Glu, Q); glutamine (Gin, E); glycine (Gly, G); histidine (His, H); isoleucine(Ile, I); leucine (Leu, L); lysine (Lys, K); methionin (Met, M); phenylalanine (Phe, F); proline (Pro, P); serine (Ser, S); threonine (Thr, T); tryptophan (Trp, W); tyrosine (Tyr, Y); valine (Val, V). Other non-naturally occurring amino acids includes p-Benzoyl-phenylalanine (Bpa); β-(1-Naphthyl)-alanine (1-Nal); β-(2-naphthyl)-alanine (2-Nal); β-cyclohexylalanine (Cha), 3,4-dichlorophenylalanine (3,4-Dcp); 4-fluorophenylalanine (4-Fpa); 4-nitrophenylalanine (4-Npa); 2-thienylalanine (Tha); 1,2,3,4-tetrahydroisoquinoline-3-carboxylic acid (Tic); 3-benzothienylalanine (3-Bal); 4-cyanophenylalanine (4-Ypa); 4-iodophenylalanine (4-lpa); 4-bromophenylalanine (4-Rpa); 4,4'-biphenylalanine (Bip); ornithine (Orn); sarcosine (Sar); pentafluorophenylalanine (Pfp); and β,β-diphenylalanine (Dip). For the purposes of the present invention, the amino acids are in the L-form (levorotatory) unless otherwise indicated. For the common amino acids, the D-form is indicated by the lower case single letter abbreviation, for example, D-alanine is "a", D-threonine is "t".

For the purposes of the present invention, when describing particular embodiments or examples, one or more units may be identified or highlighted with an asterisk, for example, R*, J*. This serves only to delineate one unit from another and to emphasize that the example focuses on changes or iterations in the particular unit. For example, each J unit whether J or J* can comprise the same elements, but for a particular example the focus is on the value of J units.

Substituted Units, -SUB

SUB units are units capable of replacing hydrogen atoms. The term "substituted" is used throughout the specification and for the purposes of the present invention the term "substituted" is defined as "replacement of a hydrogen atom, two hydrogen atoms, or three hydrogen atoms from a carbon atom to form a moiety, or the replacement of hydrogen atoms from adjacent carbon atoms to form a moiety." For example, a substituted unit that requires a single hydrogen atom replacement includes halogen, hydroxyl, and the like. A two-hydrogen atom replacement includes carbonyl, oximino, and the like. Three hydrogen replacement includes cyano, and the like. The term substituted is used throughout the present specification to indicate that a moiety, inter alia, aromatic ring, alkyl chain, can have one or more of the hydrogen atoms replaced by a substituent. For example, 4-hydroxyphenyl is a "substituted aromatic carbocyclic ring", and 3-guanidinopropyl is a "substituted $C_3$ alkyl unit." The term -SUB' is used to indicate a substitute for hydrogen is a unit which is capable of hydrogen bonding, inter alia, hydroxyl, carbonyl.

The following are non-limiting examples of moieties, which can replace one or more hydrogen atoms on carbon to form -SUB units:
  i) —NHCOR$^{30}$;
  ii) —COR$^{30}$;
  iii) —COOR$^{30}$;
  iv) —COCH=CH$_2$;
  v) —C(=NH)NH$_2$;

vi) —NHC(=NH)NH$_2$;
vii) —N(R$^{30}$)$_2$;
viii) —NHC$_6$H$_5$;
ix) =CHC$_6$H$_5$;
x) —CON(R$^{30}$)$_2$;
xi) —CONHNH$_2$;
xii) —NHCN;
xiii) —OCN;
xiv) —CN;
xv) F, Cl, Br, I, and mixtures thereof;
xvi) =O;
xvii) —OR$^{30}$;
xviii) —NHCHO;
xix) —OH;
xx) —NHN(R$^{30}$)$_2$;
xxi) =NR$^{30}$;
xxii) =NOR$^{30}$;
xxiii) —NHOR$^{30}$;
xxiv) —CNO;
xxv) —NCS;
xxvi) =C(R$^{30}$)$_2$;
xxvii) —SO$_3$M;
xxviii) —OSO$_3$M;
xxix) —SCN;
xxx) —P(O)(OH)R$^{30}$;
xxxi) —P(O)(R$^{30}$)R$^{30}$;
xxxii) —P(O)(OH)$_2$;
xxxiii) —SO$_2$NH$_2$;
xxxiv) —SO$_2$R$^{30}$;
xxxv) —NO$_2$;
xxxvi) —CF$_3$, —CCl$_3$, —CBr$_3$;
xxxvii) and mixtures thereof;

wherein R$^{30}$ is hydrogen, C$_1$–C$_{20}$ linear or branched alkyl, C$_6$–C$_{20}$ aryl, C$_7$–C$_{20}$ alkylenearyl, and mixtures thereof; M is hydrogen, or a salt forming cation. Suitable salt forming cations include, sodium, lithium, potassium, calcium, magnesium, ammonium, and the like. Non-limiting examples of an alkylenearyl unit include benzyl, 2-phenylethyl, 3-phenylpropyl, and 2-phenylpropyl. As described further herein below, units defined herein as "substituted units capable of forming a hydrogen bond" are -SUB' units, examples of which include hydroxyl and carbonyl.

For illustrative purposes, the following is a conformationally restricted ring having W, Y, and Z units attached thereto as well as an SUB substituted unit. In this example -SUB is an acetate (group (ii) wherein R$^{30}$ is methyl):

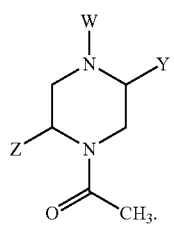

For the purposes or the present invention, the substitution for a hydrogen atom may occur on the main hydrocarbyl chain or on a branch chain.

The conformationally restricted ligands of the present invention include all enatiomeric and diasteriomeric forms and pharmaceutically acceptable salts thereof, as described herein below, said ligands having the formula:

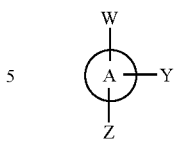

wherein A is a conformationally restricted ring system selected from the group consisting of:
  a) non-aromatic carbocyclic rings;
  b) aromatic carbocyclic rings;
  c) non-aromatic heterocyclic rings;
  d) aromatic heterocyclic rings;

wherein said rings comprises from 5 to 8 atoms. The formulator may select from any of these four types of ring systems. For the purposes of the present invention the term "carbocyclic ring" is defined herein as "a any ring, which comprises only carbon atoms." The carbon atoms may in turn be bonded to hydrogen atoms, for example, as in the case of cyclohexanyl rings, or two or more bonds may be taken together with a heteroatom, for example, and oxygen atom to form a carbonyl moiety. Also two adjacent hydrogen atoms may be absent thereby forming a double bond between two adjacent carbon atoms, for example, a cyclohexenyl ring. The rings may be substituted by any number of other atoms in addition to the 3 units, W, X, and Y described herein below. For the purposes of the present invention the term "heterocyclic ring" is defined herein "as a ring, which comprises at least one atom, nitrogen, inter alia, other than carbon." Non-limiting examples of heterocyclic rings include, piperidine, ketopiperazine, ketodiazepine, proline, piperazine, pyrroline, and pyrrolidone.

Non-limiting embodiments of non-aromatic, carbocyclic and heterocyclic rings include:

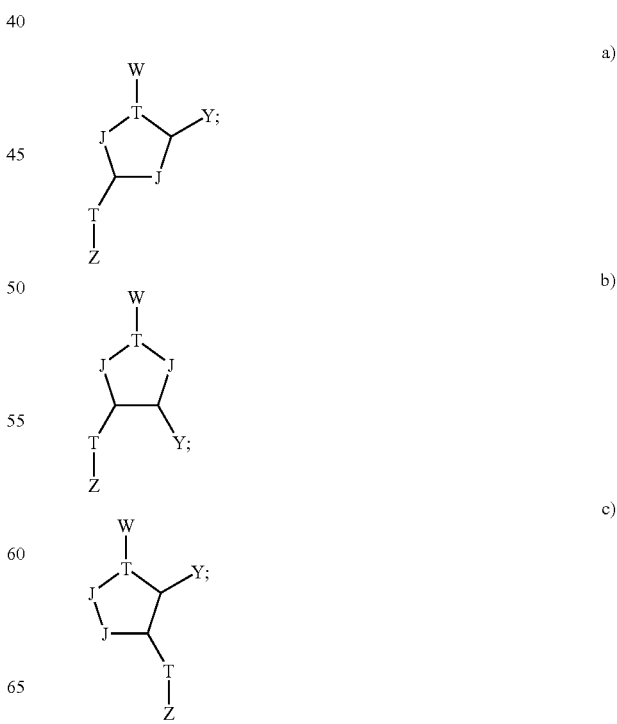

-continued d) 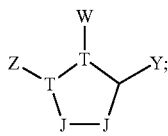

e) 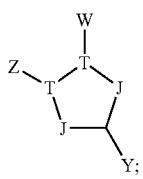

f) 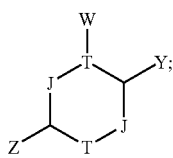

g) 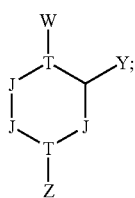

h) 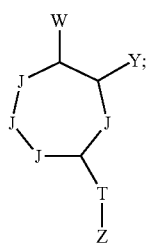

i) 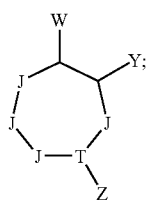

j) 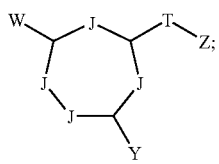

k) 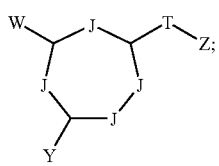

wherein W, Y and Z units are described herein below;

T is selected from the group consisting of:
i) —C(R')$_d$—; wherein each R' is independently hydrogen, $C_1$–$C_6$ linear or branched alkyl, -SUB, and mixtures thereof, d is an index having the value 1 or 2;
ii)

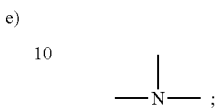

iii) —NR'—; wherein R' is hydrogen, $C_1$–$C_6$ linear or branched alkyl, -SUB, or a W, Y, or Z unit; in several embodiments R' is hydrogen, non-limiting examples of which include conformationally restricted analogs with rings having the formula:

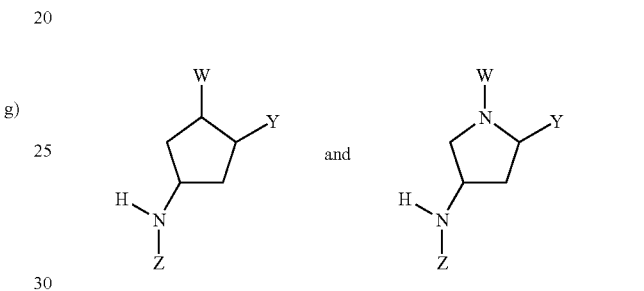

and iv) —O—;
v) —S—;
vi) —P(O)—; for example, in conjunction with conformationally restricted analogs with rings having the formula:

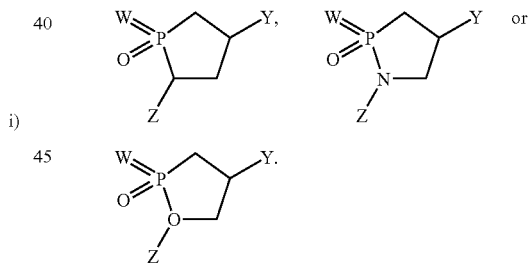

or

J is selected from the group consisting of:
i) —[C(R")$_d$]$_k$—; wherein each R" is independently hydrogen, $C_1$–$C_{12}$ linear or branched alkyl, -SUB, two R" units can be taken together with an oxygen atom to form a carbonyl unit, two R" units from any J units or an R" unit and an R' unit from a T unit can be taken together to form a carbocyclic or heterocyclic fused ring, bicyclo ring, or spiroannulated ring comprising from 3 to 7 atoms; the index d has the value of 1 or 2; the index k has the value of 1 or 2; in one embodiment, at least one J unit comprises the moiety —CF$_2$—; in other embodiments J has the formula —CH$_2$—, —C(O)—, and mixtures thereof; fused ring embodiments of J include conformationally restricted rings having the formula:

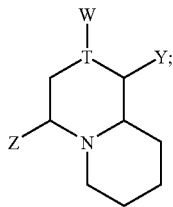

however R″ can form heterocyclic rings, for example, a cyclic ether having the formula:

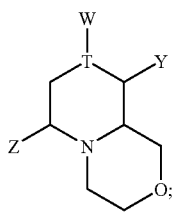

ii)

iii) —NR'—; wherein R' is hydrogen, $C_1$–$C_6$ linear or branched alkyl, or a SUB unit;
iv) —O—;
v) —S—;
vi) —P(O)— or —P(O)$_2$—; for example, in conjunction with other J or T units can form moieties having the formula —OP(O)—; —OP(O)$R^{30}$—; —OP(O)O—; or —OP(O)$R^{30}$O—;
vii) and mixtures thereof.

W Pendant Units

W units of the present invention provide a first pendant unit attached to the conformationally restricted ring. In general, the W unit has the formula:

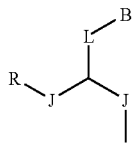

wherein J is the same as defined herein above. The W units of the present invention have several aspects, which relate to, inter alia, the choice of B unit, the selection of units which comprise the backbone of the W unit and the choice of R unit.

R Units

R is selected from the group consisting of:
a) substituted or unsubstituted non-aromatic carbocyclic rings;
b) substituted or unsubstituted aromatic carbocyclic rings;
c) substituted or unsubstituted non-aromatic heterocyclic rings;
d) substituted or unsubstituted aromatic heterocyclic rings;

wherein said rings comprises from 3 to 12 atoms. Non-limiting examples of aromatic and non-aromatic carbocyclic rings include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthrenyl, anthracenyl, fluorenyl, acenaphthylenyl, 1,2,3,4-tetrahydronaphthalenyl, and the like. Non-limiting examples of aromatic and non-aromatic heterocyclic rings include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, pyrrolyl, furanyl, thiophenyl, benzimidazolyl, and the like. Each of these rings can be suitably substituted by one or more -SUB units.

In one embodiment of the present invention R units are phenyl and substituted phenyl rings, inter alia, 3-fluorophenyl, 4-fluorophenyl, 3,5-difluorophenyl, 4-chlorophenyl, and 4-hydroxyphenyl.

In another embodiment of the present invention R units encompass rings which are selected from the group consisting of substituted or unsubstituted phenyl, α-naphthyl, β-naphthyl, 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-pyridinyl, 2-pyridinyl, 3-pyridinyl, or 4-pyridinyl.

Another embodiment comprises R units, which are phenyl, α-naphthyl, or β-naphthyl.

L Units

L is a linking group, which serves to connect two or more units of the conformationally restricted receptor ligands. The following definition of L units applies to linking groups throughout the present invention. The linking groups of the present invention may comprise any atoms or groups of atoms, which suitably connect two or more units. One example of a suitable L unit class relates to the "peptide bond, carbonyl, and modified carbonyl unit" class of linking units. In one or more embodiments of the present invention, L units may be absent.

Non-limiting examples of L units from this class of peptide bond, carbonyl, and modified carbonyl units are units selected from the group consisting of:
i) —[C($R^{11}$)$_2$]$_p$—, wherein p is from 0 to 12;
ii) —[C($R^{11}$)$_2$]$_p$(CH=CH)$_q$—; wherein p is from 0 to 12; q is from 1 to 6;
ii) —($R^{12}$)$_t$C(X)($R^{12}$)$_t$—;
iii) —C(X)$NR^{11}$—;
iv) —C(X)$R^{12}$C(X)—;
v) —C(X)$NR^{11}$C(X)—;
vi) —C(X)$NR^{11}R^{12}NR^{11}$C(X)—;
vii) —$NR^{11}$C(X)—;
viii) —$NR^{11}$C(X)$NR^{11}$—;
ix) —$NR^{11}$C(X)$R^{12}NR^{11}$—;
x) —$NR^{11}R^{12}$C(X)$NR^{11}$—;

xi) —NR¹¹C(X)R¹²C(X)O—;
xii) —OC(X)R¹²C(X)NR¹¹—;
xiii) —NR¹¹C(X)NR¹¹R¹²—;
xiv) —R¹²NR¹¹C(X)NR¹¹—;
xv) —R¹²NR¹¹C(X)NR¹¹R¹²—;
xvi) —NR¹¹—;
xvii) —R¹²NR¹¹—;
xix) —NR¹¹R¹²—;
xx) —NR¹¹N=N—;
xxi) —NR¹¹NR¹¹—
xxii) —OR¹²—;
xxiii) —R¹²O—;
xxii) —(R¹²)$_t$OC(O)(R¹²)$_t$—;
xxiii) —(R¹²)$_t$C(O)O(R¹²)$_t$—;
xxiv) —(R¹²)$_t$OC(O)O(R¹²)$_t$—;
xxv) —S—;
xxvi) —(R¹²)$_t$S(R¹²)$_t$—;
xxvii) —(R¹²)$_t$S(X)(R¹²)$_t$—;
xxviii) —(R¹²)$_t$S(X)$_2$(R¹²)$_t$—;
xxix) —(R¹²)$_t$NR¹¹S(X)(R¹²)$_t$—;
xxx) —(R¹²)$_t$S(X)NR¹¹(R¹²)$_t$—;
xxxi) —(R¹²)$_t$NR¹¹S(X)$_2$(R¹²)$_t$—;
xxxii) —(R¹²)$_t$S(X)$_2$NR¹¹(R¹²)$_t$—;

wherein $R^{11}$ is hydrogen, linear or branched $C_1$–$C_{10}$ alkyl, hydroxyl, -SUB, or mixtures thereof; $R^{12}$ is $C_1$–$C_{16}$ linear or branched, substituted or unsubstituted alkylene, substituted or unsubstituted phenylene, or mixtures thereof; or an $R^{11}$ and $R^{12}$ unit can be taken together to form a ring; X is oxygen, sulfur, =NR¹¹, and mixtures thereof; t is 0 or 1.

The following relate to one embodiment of L units:
 i) —C(O)NH—;
 ii) —C(O)NHC(O)—;
 iii) —NHC(O)—;
 iv) —NH—;
 v) —(CH$_2$)$_b$NH—; wherein b is from 1 to 3;
 vi) —NH(CH$_2$)$_b$—; wherein b is from 1 to 3.

The following relate to another embodiment of L units:
 i) —(CH$_2$)$_p$—, wherein p is from 0 to 12;
 ii) —C(O)—;
 iii) —(CH$_2$)$_b$NH—; wherein b is from 1 to 3.

Other embodiments of the present invention may utilize only the —NH— moiety as a linking units while still further embodiments utilize both —C(O)NH— and —NHC(O)—. Yet further embodiments select equally from the following L units:
 i) —C(O)NH—;
 ii) —NHC(O)—;
 iii) —NH—.

Other embodiments may comprise a combination of carbonyl and modified carbonyl L units, for example, units having the formula:
 i) —C(O)—;
 ii) —C(=NH)—;
 iii) —C(O)NH—;
 iv) —C(=NH)NH—;
 v) —NHC(O)—;
 vi) —NHC(=NH)—;
 vii) —NHC(=NH)NH—;

or only modified carbonyl units having the formula:
 i) —C(=NH)—;
 ii) —C(=NH)NH—;
 iii) —NHC(=NH)—;
 iv) —NHC(=NH)NH—.

Examples of L units wherein $R^{11}$ and $R^{12}$, two $R^{11}$ units or two $R^{12}$ units are taken together to form a ring include the conformationally restricted L units:

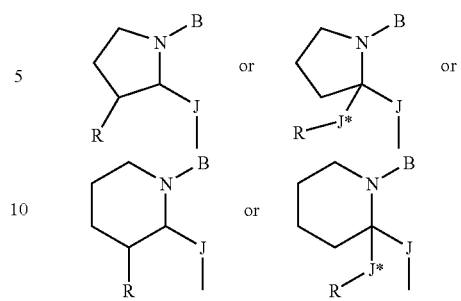

however, the rings formed by the $R^{11}$ and $R^{12}$ can also comprise one or more heteroatoms, for example a linking unit having the formula:

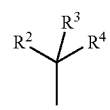

B Units

The B units of the present invention encompass several distinct aspects, each aspect having multiple embodiments depending upon the requirements which the formulator sets forth for the receptor ligand.

B units do not require a chiral center, but many embodiments of B described herein comprise a chiral center. Several non-limiting embodiments of B, having chiral and non-chiral centers, are listed herein below.

Formulators of MC-4, MC-3, and MC-4 and MC-3 receptor ligands will recognize that when any two of $R^2$, $R^3$, and $R^4$ are the same, B will not have a chiral center unless one of the units $R^2$, $R^3$, and $R^4$ comprises a chiral center or two of $R^2$, $R^3$, or $R^4$ are taken together to form a ring which has a chiral center. B units are represented by the formula:

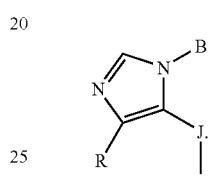

wherein $R^2$, $R^3$, and $R^4$ are described herein below.

A first aspect of B relates to units wherein $R^2$, $R^3$, and $R^4$ units are independently selected from the group:
 A) rings comprising:
  a) substituted or unsubstituted aromatic carbocyclic rings;
  b) substituted or unsubstituted aromatic heterocyclic rings;
  c) and mixtures thereof;
 B) hydrogen;
 C) SUB units; and
 D) mixtures thereof.

Non-limiting examples of substituted or unsubstituted rings according to (A) above include: benzyl, 4-hydroxybenzyl, 3-chlorobenzyl, 4-chlorobenzyl, 3,5-dichlorbenzyl, 4-fluorobenzyl, (imidazol-2-yl)methyl, (imidazol-4-yl)methyl, 2-phenylethyl, 2-(4-hydroxyphenyl)ethyl, 3-(4-hydroxyphenyl)propyl, and the like.

In one particular embodiment of this first aspect of B units, said B units comprise a chiral unit having the formula:

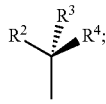

wherein $R^2$ and $R^3$ are each independently hydrogen, —C(X)N($R^{13}$)$_2$; —N($R^{13}$)$_2$; —N$^+$($R^{13}$)$_3$D$^-$; —C(X)N$^+$($R^{13}$)$_3$D$^-$; —NR$^{13}$C(X)R$^{14}$; and mixtures thereof; provided $R^2$ and $R^3$ are not the same; $R^{13}$ is hydrogen, $C_1$–$C_{10}$ alkyl, or mixtures thereof; $R^{14}$ is $C_1$–$C_{16}$ linear or branched, substituted or unsubstituted alkyl, $C_7$–$C_{16}$ linear or branched, substituted or unsubstituted alkylenearyl; X is oxygen, sulfur, =NR$^{13}$, and mixtures thereof; D is a salt forming anion; $R^4$ is $C_7$–$C_{16}$ substituted or unsubstituted alkylarylene, inter alia, benzyl and substituted benzyl. Specific examples of $R^2$ and $R^3$ include —CH$_2$C(O)CH$_3$, —NHC(O)CH$_3$, —NHC(O)CH$_2$CH$_3$, and —NHC(O)CH$_2$CH$_2$CH$_3$.

One aspect of W comprises units having the formula:

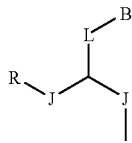

wherein J has the formula —(CH$_2$)—, —C(O)—, and mixtures thereof;

L units are selected form the group consisting of:
i) —C(O)NH—;
ii) —C(O)NHC(O)—;
iii) —NHC(O)—;
iv) —NH—;
v) —(CH$_2$)$_b$NH—; wherein b is from 1 to 3; and
vi) —NH(CH$_2$)$_b$—; wherein b is from 1 to 3;
R is substituted or unsubstituted aryl;
B is hydrogen or a unit having the formula:

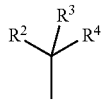

wherein $R^2$, $R^3$, and $R^4$ units are independently selected from the group:
a) rings comprising:
  i) substituted or unsubstituted aromatic carbocyclic rings;
  ii) substituted or unsubstituted aromatic heterocyclic rings;
  iii) and mixtures thereof;
b) hydrogen;
c) a unit selected from the group consisting of —CH$_2$C(O)CH$_3$, —NHC(O)CH$_3$, —NHC(O)CH$_2$CH$_3$, and —NHC(O)CH$_2$CH$_2$CH$_3$;

d) at least two of $R^2$, $R^3$, or $R^4$ can be taken together to form a ring; and
e) mixtures thereof.

One particular embodiment of this aspect of B comprises $R^3$ units that are hydrogen and $R^2$ units that have the formula —NR$^{13}$C(X)R$^{14}$, wherein $R^{14}$ is $C_1$–$C_4$ linear alkyl. In one particular series of embodiments $R^2$ is —NHC(O)CH$_3$ and $R^3$ is hydrogen while $R^4$ is one or more units selected from the group consisting of benzyl, 4-hydroxybenzyl, 4-chlorobenzyl, 4-methoxybenzyl, 3-nitrobenzyl, and mixtures thereof. Another embodiment combines $R^2$ and $R^3$ both as hydrogen with $R^4$ units selected from the group consisting of phenyl, 2-imidazolyl, 4-imidazolyl, 4-fluorophenyl, 4-hydroxyphenyl, and 4-acetoxyphenyl. These embodiments of this aspect are further exemplified in the analog tables herein below.

Other iterations of this aspect utilize L-amino acids and derivatives thereof as a source of B units, for example, N-acetyl-L-tyrosine as in the examples herein below.

One embodiment of this iteration which encompasses the use of chiral amino acids for elements of W units, relates to coupling a B unit which is derived from a L-amino acid with an R unit which is derived from a D-amino acid. For example, a W unit comprising the diamino acid residue N-acetyltyrosinyl-D-phenylalanine (N-acetyl-Yf), having the formula:

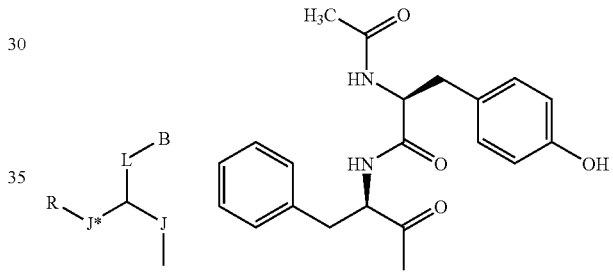

wherein J is —C(O)—, J* is —CH$_2$—, R is phenyl, L is —NHC(O)—, $R^2$, $R^3$ and $R^4$ derive from tyrosine.

Another embodiment of this aspect of the present invention relates to B units, which can be conveniently obtained from D-amino acids as a source of a chiral carbon atom, for example, B units having the formula:

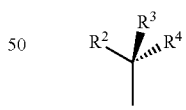

wherein $R^3$ is hydrogen, $R^2$ is one or more units selected from the group consisting of benzyl, 4-hydroxybenzyl, 4-chlorobenzyl, 4-methoxybenzyl, 3-nitrobenzyl, and mixtures thereof; $R^4$ is a units selected from —C(O)N(H)$_2$, —N(H)$_2$—N$^+$(H)$_3$D$^-$, —C(O)N$^+$($R^{14}$)$_3$D$^-$, —NHC(O)R$^{14}$, and mixtures thereof; $R^{14}$ is a $C_7$–$C_{16}$ substituted or unsubstituted alkylarylene unit, non-limiting examples of which are benzyl, 4-hydroxybenzyl, 2-phenylethyl, 3-phenyl ethyl, 2-(4-hydroxyphenyl)ethyl, and the like; D is a salt forming anion.

One embodiment of W units relates to compounds comprising a primary amino unit, for example, a W unit having the formula:

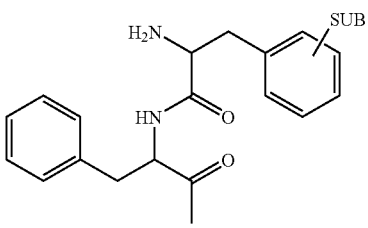

wherein the SUB unit represents one or more replacements for hydrogen atoms as defined herein above. Other non-limiting examples of this embodiment include:

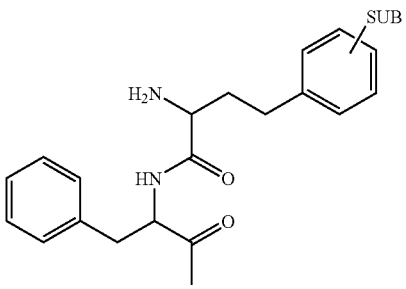

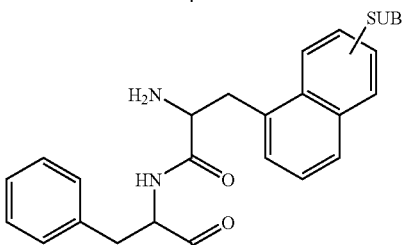

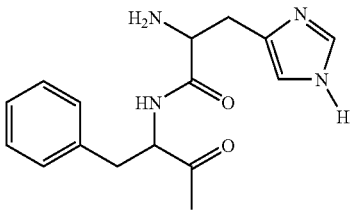

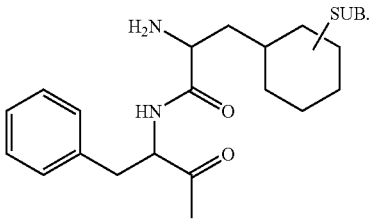

Another aspect of the present invention relates to B units taken together with a sulfonamide linking unit to provide receptor ligands having W units of the formula:

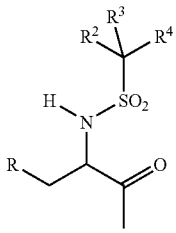

wherein $R^2$, $R^3$, and $R^4$ are defined hereinabove. One embodiment of this aspect relates to receptor ligands wherein at least two of $R^2$, $R^3$, or $R^4$ are taken together to form a ring or wherein $R^4$ comprises an aryl or heteroaryl group, said units selected from the group consisting of phenyl, benzyl, 2-phenethyl, naphthyl, naphthalen-2-ylmethyl, naphthalen-2-ylethyl, and 6-hydroxynaphtalen-2ylmethyl, an non-limiting example of which comprises a scaffold having the formula:

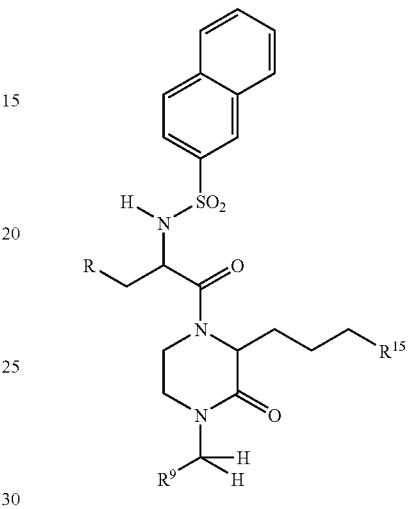

wherein R, $R^9$, and $R^{15}$ represents any moiety described herein.

Another aspect of the present invention relates to B units wherein at least one, preferably at least two, of $R^2$, $R^3$, or $R^4$ units comprise a hydrogen bonding unit selected from the group:

A) $C_1$–$C_{12}$ linear or branched alkyl units substituted by one or more hydrogen bonding SUB' units;
B) $C_2$–$C_{12}$ linear or branched alkenyl units substituted by one or more hydrogen bonding SUB' units;
C) hydrogen;
D) SUB' units; and
E) mixtures thereof;

wherein SUB' units are "substitutions for hydrogen which comprise units which are hydrogen bonding units."

Non-limiting examples of -SUB' units are selected from the group consisting of:
i) —NHCOR$^{30}$;
ii) —OH;
iii) —COOH;
iv) —C(=NH)NH$_2$;
v) —NH$_2$;
vi) —NHC$_6$H$_5$;
vii) —CONH$_2$;
viii) —CONHNH$_2$;
ix) —NHCN;
x) —=O;
xi) —NHCHO;
xii) —NHNH$_2$;
xiii) =NH;
xiv) =NOH;
xv) —NHOH;
xvi) —CNO;
xvii) —SO$_3$M;
xviii) —OSO$_3$M;

xix) —P(O)(OH)R$^{30}$;
xx) —P(O)(R$^{30}$)R$^{30}$;
xxi) —P(O)(OH)$_2$;
xxii) —SO$_2$NH$_2$;
xxiii) —NO$_2$;
xxiv) and mixtures thereof;

Non-limiting examples of W units which comprise a B unit having at least two hydrogen bonding units have the formula:

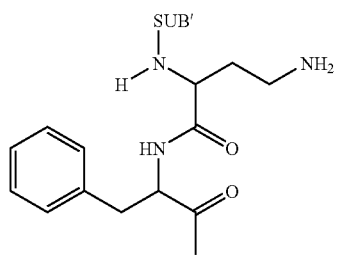

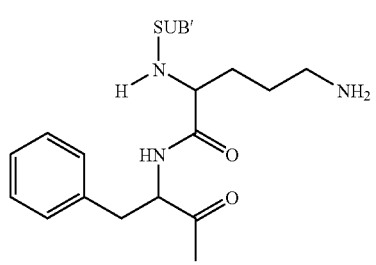

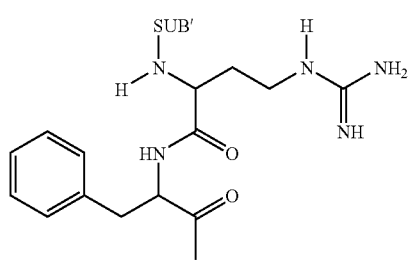

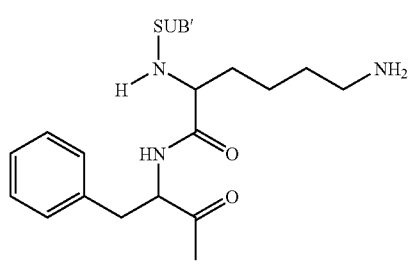

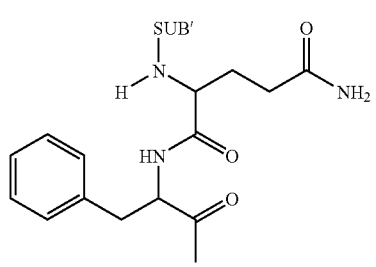

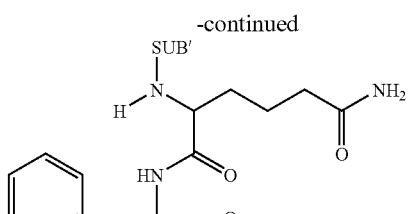

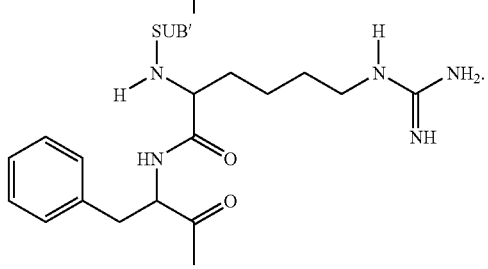

Another aspect of B units relates to $R^2$, $R^3$, and $R^4$ units one of which comprises a hydrogen bonding unit attached to a ring, or two or three of $R^2$, $R^3$, and $R^4$ units are taken together to form a ring, an example of which has the formula:

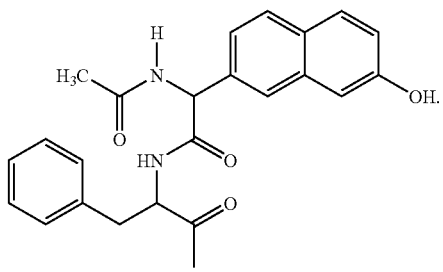

Further examples of this aspect of W units have the formula:

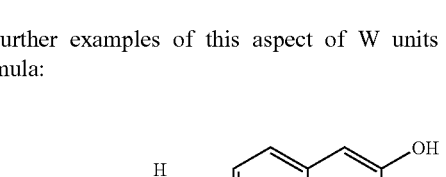

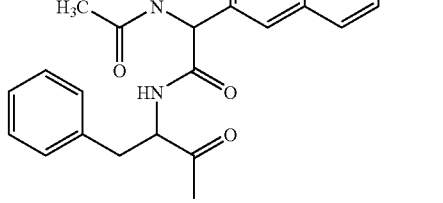

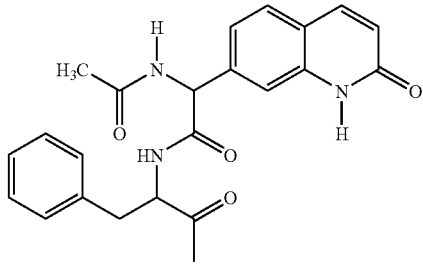

-continued

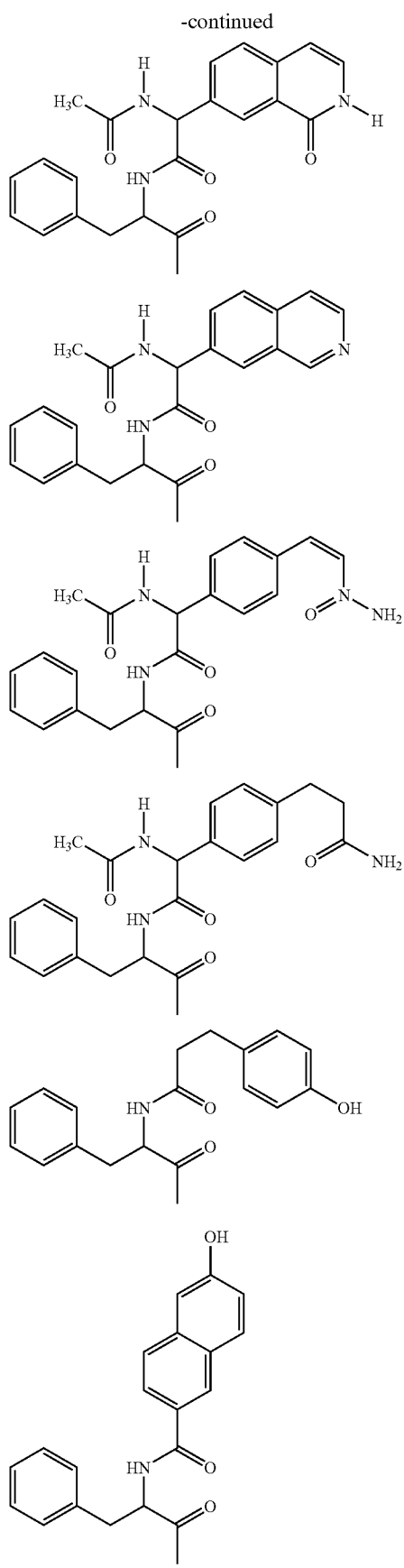

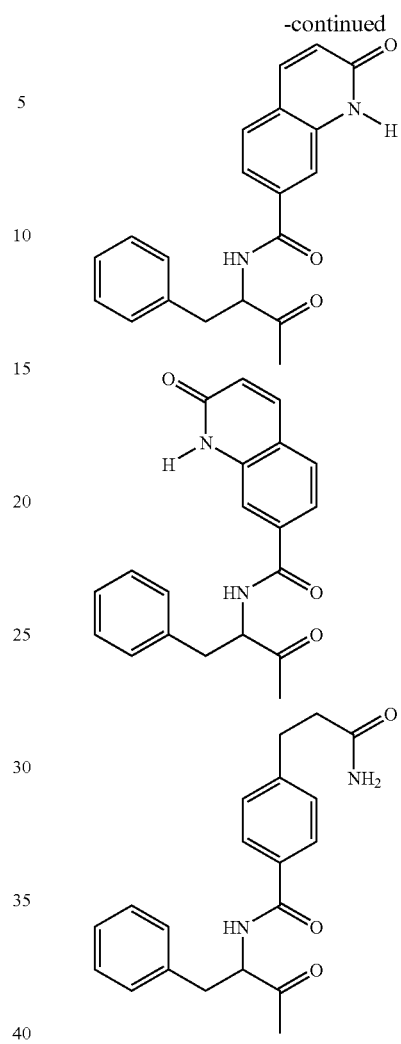

Y units have the formula:

—L—R[15]

wherein R[15] is a heteroatom-containing group.

The first aspect of Y units relates to short chain alkyl or alkenyl (lower hydrocarbyl) esters having the formula:

—(CH$_2$)$_b$—R[15]

wherein the index b is from 1 to 4; R[15] is a linear ester or amide, non-limiting examples of which include: —C(O)OCH$_3$; —C(O)OCH$_2$CH$_3$; —C(O)OCH$_2$CH$_2$CH$_3$; —C(O)OCH$_2$CH$_2$CH$_2$CH$_3$; —C(O)OCH(CH$_3$)$_2$; —C(O)OCH$_2$CH(CH$_3$)$_2$; —C(O)OCH$_2$CH═CHCH$_3$; —C(O)OCH$_2$CH$_2$CH(CH$_3$)$_2$; —C(O)OCH$_2$C(CH$_3$)$_3$; —OC(O)CH$_3$; —OC(O)CH$_2$CH$_3$; —OC(O)CH$_2$CH$_2$CH$_3$; —OC(O)CH(CH$_3$)$_2$; —OC(O)CH$_2$CH$_2$CH$_2$CH$_3$; —OC(O)CH$_2$CH(CH$_3$)$_2$; —OC(O)CH$_2$CH═CHCH$_3$; —OC(O)CH$_2$C(CH$_3$)$_3$; —OC(O)CH$_2$CH$_2$CH(CH$_3$)$_2$; and the like; and short chain substituted or non-substituted amides, non-limiting examples of which are —C(O)NHCH$_3$; —C(O)NHCH$_2$CH$_3$; —C(O)NHCH(CH$_3$)$_2$; —C(O)NHCH$_2$CH$_2$CH$_3$; —C(O)NHCH$_2$CH$_2$CH$_2$CH$_3$; —C(O)NHCH$_2$CH(CH$_3$)$_2$; —C(O)NH$_2$; —C(O)NHCH$_2$CH═CHCH$_3$; —C(O)NHCH$_2$CH$_2$CH(CH$_3$)$_2$; —C(O)NHCH$_2$C(CH$_3$)$_3$; —C(O)NHCH$_2$CH$_2$SCH$_3$; —C(O)NHCH$_2$CH$_2$OH; —NHC(O)

CH₃; —NHC(O)CH₂CH₃; —NHC(O)CH₂CH₂CH₃; —NHC(O)CH₃; —NHC(O)CH₂CH₃; —NHC(O)CH(CH₃)₂; —NHC(O)CH₂CH₂CH₃; —NHC(O)CH₂CH₂CH₂CH₃; —NHC(O)CH₂CH(CH₃)₂; —NHC(O)₂; —NHC(O)CH₂CH=CHCH₃; —NHC(O)CH₂CH(CH₃)₂; —NHC(O)CH₂C(CH₃)₃; —NHC(O)CH₂CH₂SCH₃; —NHC(O)CH₂CH₂OH; —NHC(O)CH₃; —NHC(O)CH₂CH₃; —NHC(O)—CH₂CH₂CH₃; and the like.

The second aspect of Y units relates to moieties, which comprise guanidine and guanidine mimetics having the formula:

—(CH₂)_z—R¹⁵ wherein R¹⁵ is a unit selected from the group consisting of:
a) —C(X)N(R¹⁶)₂;
b) —C(X)NR¹⁶N(R¹⁶)₂;
c) —NR¹⁶C(X)N(R¹⁶)₂; and
d) —NHN(R¹⁶)₂;

wherein X is =O, =S, NR¹⁶, and mixtures thereof, R¹⁶ is hydrogen, methyl, cyano, hydroxy, nitro, and mixtures thereof, the index z is from 0 to 5.

Non-limiting examples of R¹⁵ units which comprise this second aspect of Y units include:

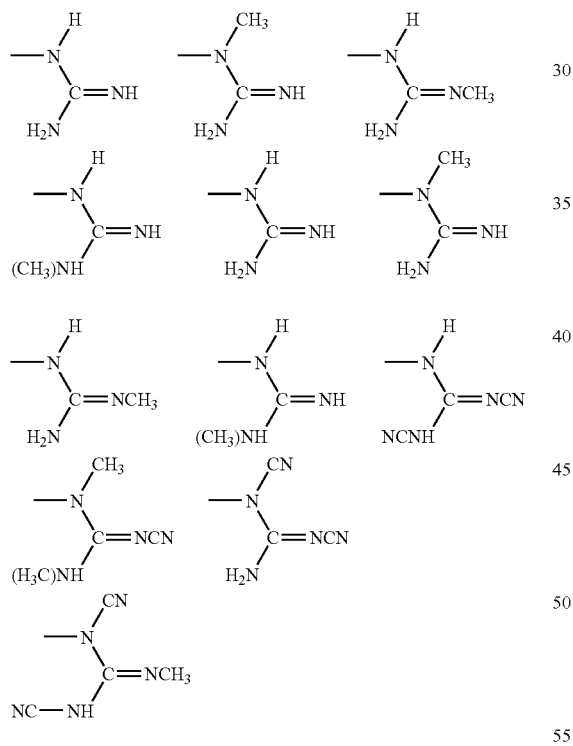

The third aspect of the present invention as it relates to Y units comprise 5-member heterocyclic rings wherein R⁵ is selected from the group consisting of:
i) triazolyl having the formula:

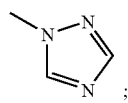

ii) tetrazolyl having the formula:

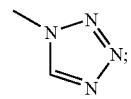

iii) thiazolyl, 2-methylthiazolyl, 4-mentylthiazolyl, 5-methylthiazolyl having the formula:

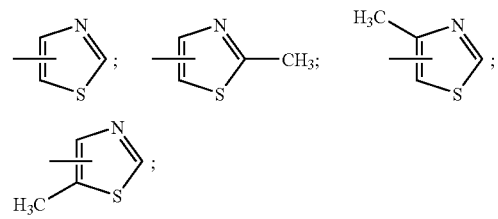

iv) 1,3,4-thiadiazolyl, 2-methyl-1,3,4-thiadiazolyl having the formula:

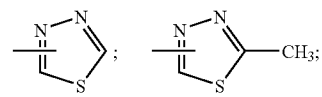

v) 1,2,5-thiadiazolyl, 3-methyl-1,2,5-thiadiazolyl having the formula:

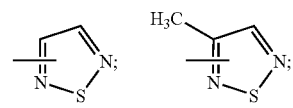

vi) oxazolyl, 2-methyloxazolyl, 4-methyloxazolyl, 5-methyloxazolyl having the formula:

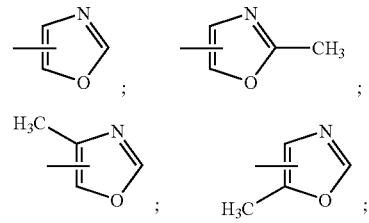

vii) imidazolyl, 2-methylimidazolyl, 5-methylimidazolyl having the formula:

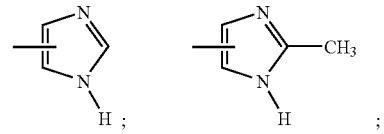

-continued

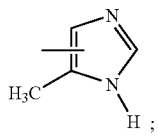

viii) 5-methyl-1,2,4-oxadiazolyl, 2-methyl-1,3,4-oxadiazolyl, 5-amino-1,2,4-oxadiazolyl, having the formula:

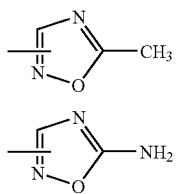

ix) 1,2-dihydro[1,2,4]triazol-3-one-1-yl, 2-methyl-1,2-dihydro[1,2,4]triazol-3-one-5-yl, having the formula:

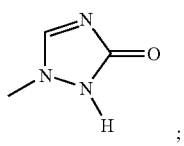

x) oxazolidin-2-one-3-yl; 4,4-dimethyloxazolidin-2-one-3-yl; imidazolidin-2-one-1-yl; 1-methylimidazolidin-2-one-1-yl, having the formula:

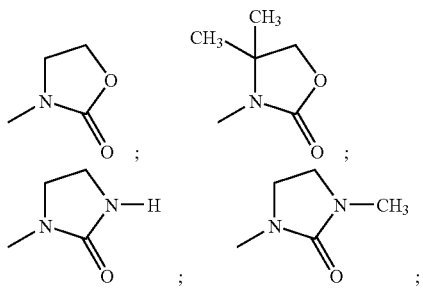

xi) 2-methyl-1,3,4-oxadiazolyl, 2-amino-1,3,4-oxadiazolyl, 2-(N,N-dimethylamino)-1,3,4-oxadiazolyl, having the formula:

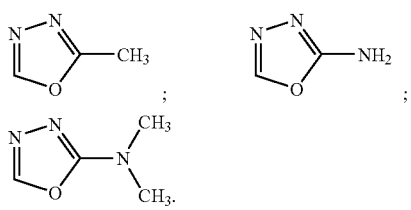

These $R^{15}$ units when taken together with L units selected from the group consisting of:

i) $-[C(R^{11})_2]_p-$, wherein p is from 0 to 12; and
ii) $-R^{12}NR^{11}-$;

afford heterocyclic Y units, non-limiting examples of which include units having the formula:

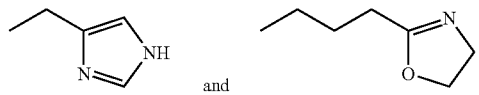

A fourth aspect of Y units relates to moieties wherein $R^{15}$ comprises a six membered heterocyclic ring, non-limiting examples of which include:

i) pyridinyl units having the formula:

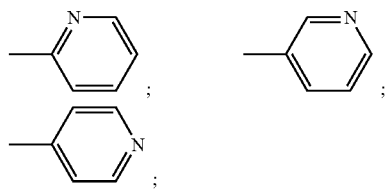

ii) pyrimidinyl units having the formula:

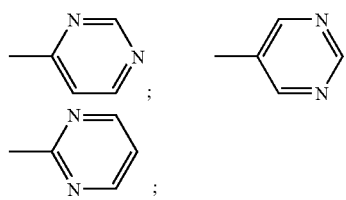

ii) piperidinyl units having the formula:

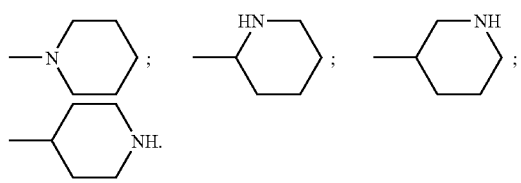

Another aspect of the present invention relates to $R^{15}$ units which are $-NH_2$, and $-OH$.

However, in the broadest sense, $R^{15}$ when taken together with a linking group having the $-(CH_2)_p-$ wherein p is from 0 to 12, $R^{15}$ can be any of the units selected from the group consisting of amino, guanidino, guanyl, amidino, pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,3-isoxazolyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl, 2H-indenyl, benzofuranyl, isobenzofuranyl, indolyl, 3H-indolyl, 1H-inolyl, benzoxazolyl, 2H-1-benzopyranyl, quinolinyl, isoquinolinyl, quinazolinyl, 2H-1,4-benzoxazinyl, pyrrolidinyl, pyrrolidonyl, pyrrolinyl, quinoxalinyl, pyrrolyl, benzimidazolyl, and mixtures thereof.

Z Units

Z units have the formula:

wherein $R^8$ and $R^9$ are each independently
i) hydrogen;
ii) substituted or unsubstituted phenyl;
iii) $C_7$–$C_{16}$ substituted or unsubstituted alkylarylene;
iv) naphthyl;
v) quinolinyl,
vi) imidazolyl,
vii) indolyl;
viii) pyridinyl;
ix) $C_3$–$C_{10}$ substituted or unsubstituted non-aromatic carbocyclic ring;
x) $C_2$–$C_{10}$ substituted or unsubstituted non-aromatic heterocyclic ring;
xi) and mixtures thereof;

$R^{10}$ is hydrogen, —C(X)N($R^{16}$)$_2$, —N($R^{16}$)$_2$—N$^+$($R^{16}$)$_3$D$^-$, —C(X)N$^+$($R^{16}$)$_3$D$^-$, —NR$^{16}$C(X)R$^{17}$, and mixtures thereof; $R^{16}$ is hydrogen, $C_1$–$C_{10}$ alkyl, or mixtures thereof; $R^{17}$ is $C_1$–$C_{16}$ linear or branched, substituted or unsubstituted alkyl, $C_7$–$C_{16}$ linear or branched, substituted or unsubstituted alkylenearyl; X is oxygen, sulfur, =NR$^{16}$, and mixtures thereof; D is a salt forming anion.

In one embodiment of the present invention, $R^8$ is hydrogen; $R^9$ is indolyl or naphthyl; and $R^{10}$ is —NHC(O)CH$_3$.

However, Z units may comprise a chiral center represented by the formula:

wherein $R^8$, $R^9$, and $R^{10}$ are the same as defined herein above.

Another embodiment of the present invention comprises Z units, which are tethered to the conformationally restricted ring component by a T unit comprising —O—, —NH—, —S—, and the like, having the formula:

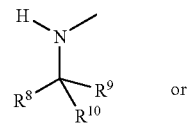

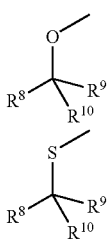

wherein $R^8$, $R^9$, and $R^{10}$ are each independently
i) hydrogen;
ii) substituted or unsubstituted phenyl;
iii) $C_7$–$C_{16}$ substituted or unsubstituted alkylarylene;
iv) naphthyl;
v) quinolinyl,
vi) imidazolyl,
vii) indolyl;
viii) pyridinyl;
ix) and mixtures thereof;

In one embodiment of this T unit comprising tether, $R^8$ and $R^9$ are each a hydrogen and $R^{10}$ is selected from:
i) substituted or unsubstituted phenyl;
ii) $C_7$–$C_{16}$ substituted or unsubstituted alkylarylene;
iii) naphthyl, either α or β linked (1-naphthyl, 2-naphthyl);
iv) quinolinyl,
v) imidazolyl,
vi) indolyl;
vii) pyridinyl;
viii) and mixtures thereof;

Receptor Ligands and Embodiments

One aspect of the present invention relates to a combination of the different aspects of W pendant units with a variety of conformationally restricted A rings and various Y and Z pendant units. Several aspects of W units comprise a di-peptide backbone, di-peptides, or di-peptide mimetics. These variations of W can be combined with any size conformationally restricted ring, for example, the 5, 6, and 7 atom rings which provide receptor ligand scaffolds having the formula:

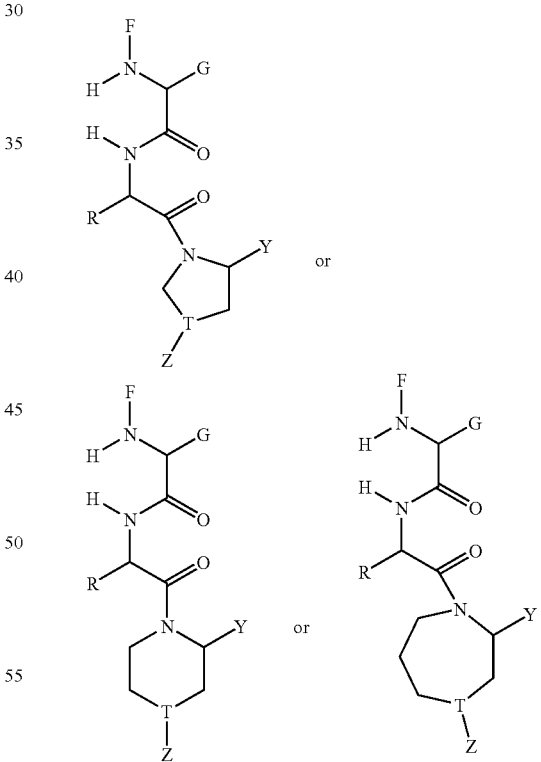

wherein R is a unit comprising at least one aromatic ring. This embodiment of the present invention illustrates the wide range of independent substitutions which the formulator can make at positions F and G relative to the size of the A ring and the Y and Z pendant units. In the examples above, G units can be the side chain of an amino acid while F units can be hydrogen of a suitable capping group.

In a first embodiment of this aspect, R is an aryl unit, W is a di-peptide mimetic comprising G and F units as defined herein below.

F units comprise:
a) hydrogen;
b) SUB units; non-limiting examples of which include
   i) —NHC(X)R$^{30}$;
   ii) —C(X)R$^{30}$;
   iii) —C(X)N(R$^{30}$)$_2$;
   iv) —R$^{30}$;
   wherein R$^{30}$ is C$_1$–C$_{22}$ linear or branched, substituted or unsubstituted alkyl; C$_3$–C$_{22}$ linear or branched, substituted or unsubstituted cycloalkyl; C$_2$–C$_{22}$ linear or branched, substituted or unsubstituted alkenyl; C$_3$–C$_{22}$ linear or branched, substituted or unsubstituted cycloalkenyl; C$_1$–C$_{22}$ linear or branched, substituted or unsubstituted heteroalkyl; C$_1$–C$_{22}$ linear or branched, substituted or unsubstituted cycloheteroalkyl; C$_2$–C$_{22}$ linear or branched, substituted or unsubstituted heteroalkenyl; C$_2$–C$_{22}$ linear or branched, substituted or unsubstituted cycloheteroalkenyl; and mixtures thereof.

G units comprise:
a) C$_6$–C$_{12}$ substituted or unsubstituted aryl; for example, phenyl, 4-hydroxyphenyl, 4-methylphenyl, naphthyl;
b) C$_6$–C$_{12}$ substituted or unsubstituted heteroaryl C$_6$–C$_{12}$ substituted or unsubstituted heteroaryl; for example, indolyl;
c) C$_7$–C$_{17}$ substituted or unsubstituted alkylenearyl; for example, benzyl, 4-hydroxybenzyl;
d) C$_3$–C$_{17}$ substituted or unsubstituted alkyleneheteroaryl; and
e) mixtures thereof.

However, one aspect of the di-peptide mimetic embodiment relates to non-peptide backbones, for example, receptor ligand scaffolds having the formula:

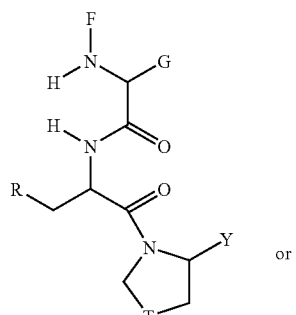

or

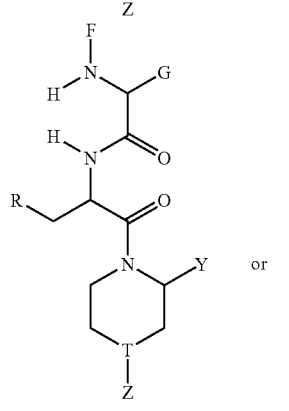

-continued

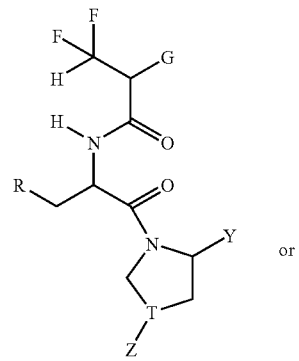

or

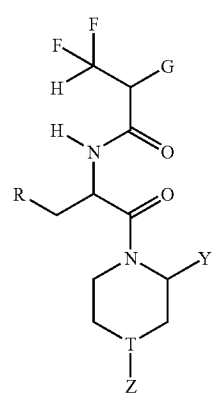 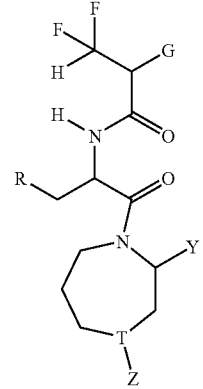

or

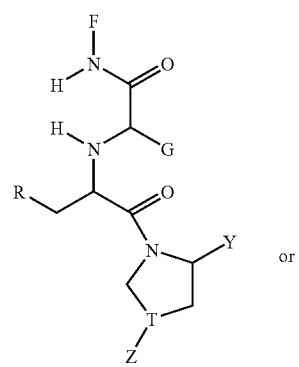

or

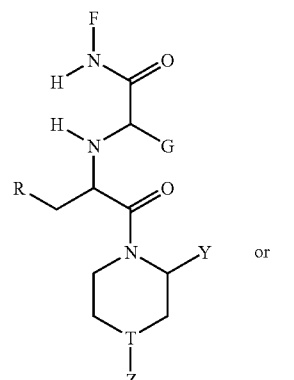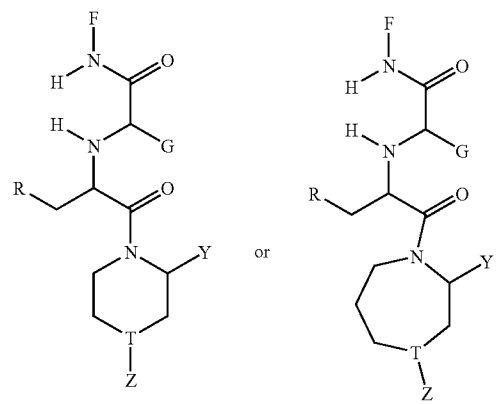

-continued

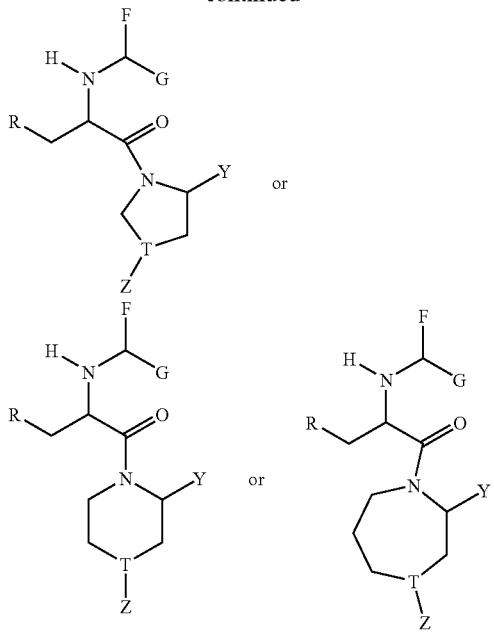

The present invention also comprises several aspects which relate to the presence of a 4-carbon atom conformationally restricted segment linking a di-peptide W unit or di-peptide mimetic W unit and a Z unit.

One embodiment of the present invention, relating to analogs having a four-atom segment connecting a W unit and a Z unit, has general formula:

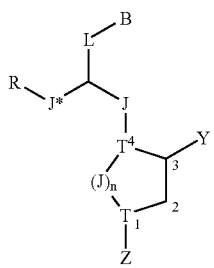

wherein T is —CH—, —N—, and mixtures thereof, R, J, L, Y, B, and Z are the same as defined herein above; the index n is from 1 to 4.

For this embodiment of the 4-carbon atom segment, —J*R units are taken together to form units selected from the group consisting of $C_1$–$C_{12}$ linear or branched alkyl; $C_6$–$C_{12}$ substituted or unsubstituted aryl; $C_6$–$C_{12}$ substituted or unsubstituted heteroaryl; $C_7$–$C_{17}$ substituted or unsubstituted alkylenearyl; $C_3$–$C_{17}$ substituted or unsubstituted alkyleneheteroaryl; and mixtures thereof.

Another example of this aspect has the formula:

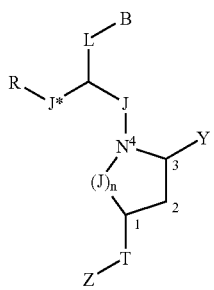

wherein R, J, L, J*, T, Y, B, and Z are the same as defined herein above; the index n is from 1 to 4.

One aspect of the receptor ligands of the present invention relates to conformationally restricted 4-amino acid containing peptides or peptide mimetics having Y-f-R-W as the core amino acid constituents, [tyrosinyl-D-phenylalanylargininyltryptophanamide (Tyr-D-Phe-Arg-Trp-NH$_2$)], having a primary template with the general formula:

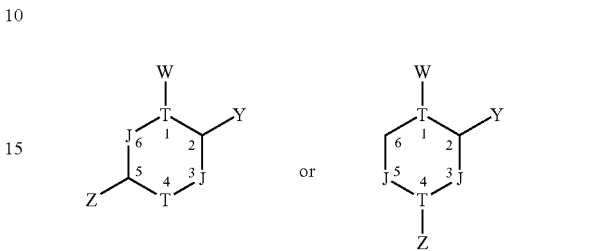

which provide conformationally restricted rings having the formula:

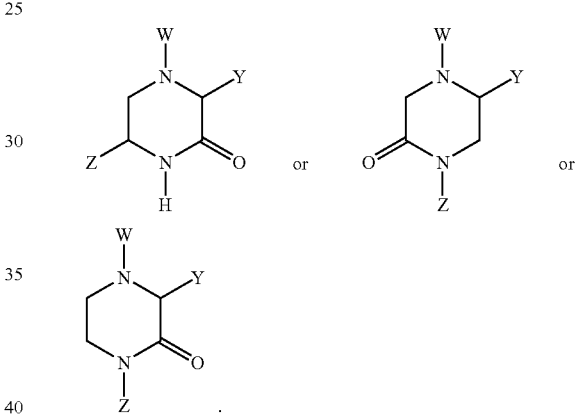

Another embodiment of the tyrosinyl-D-phenylalanyl moiety comprising W unit relates to compounds, an example of which is the receptor ligand having the formula:

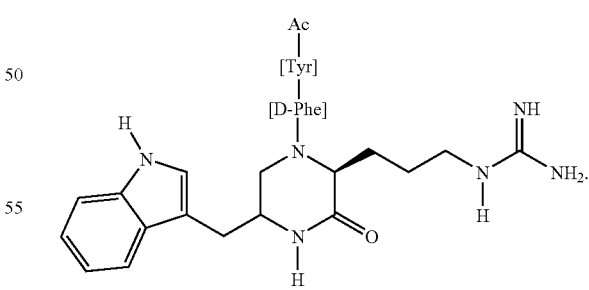

Another variation of the conformational restriction of a tetra-peptide relates to the 4 residue peptide having H-f-R-W as the core amino acid constituents, histidinyl-D-phenylalanylargininyltryptophanamide (His-D-Phe-Arg-Trp-NH$_2$), is conformationally restricted, and further optionally modified, to form one or more primary templates having the general formula:

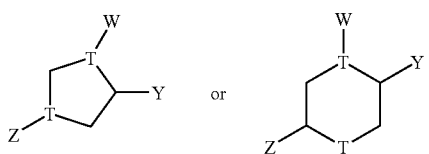

wherein W is a His-D-Phe-moiety. Due to the presence of the histidine amino acid unit as part of the W unit, this embodiment comprises a B unit having a heterocyclic $R^4$ unit, which encompasses a the aspect of B units which relates to conformationally restricted hydrogen bonding B units. Variations of this ring structure wherein Y and Z units are modified as well as J units, comprise an embodiment of the present invention which is reflected in the enumerated examples herein below.

The following are non-limiting examples of one embodiment of this conformationally restricted template:

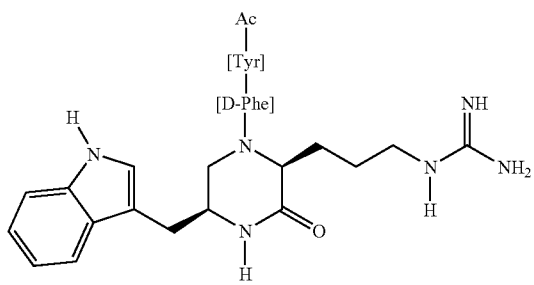

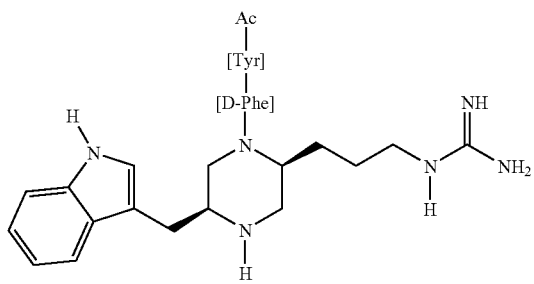

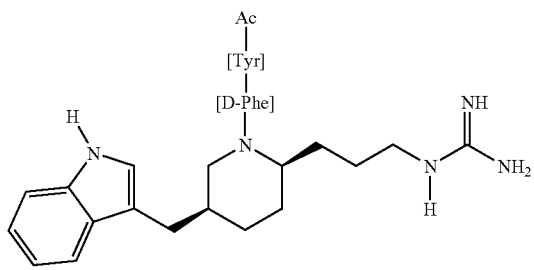

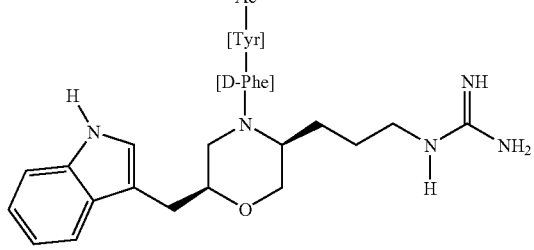

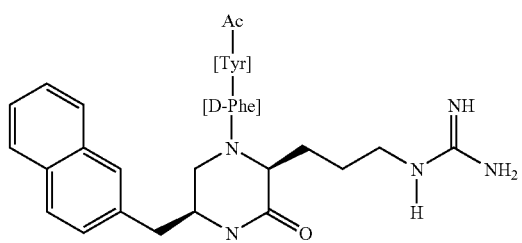

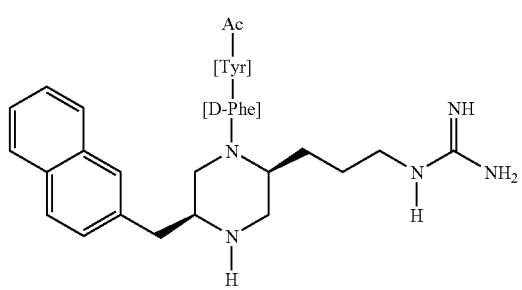

Another embodiment of the present invention relates to 5-member ring MC4 and MC4 an/or MC3 receptor ligands, for example ligands having a conformationally restricted template having the formula:

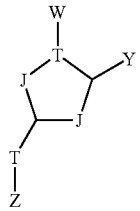

with modifications made thereto to provide the following non-limiting examples of receptor ligand:

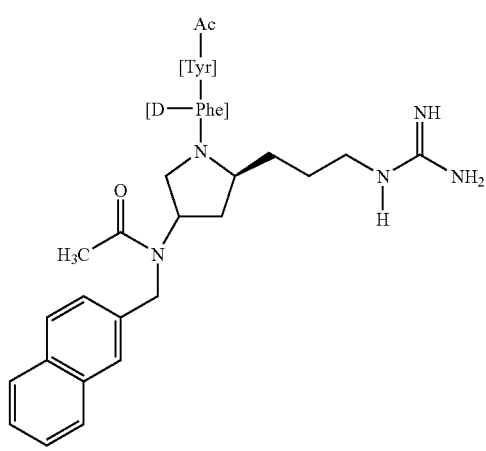

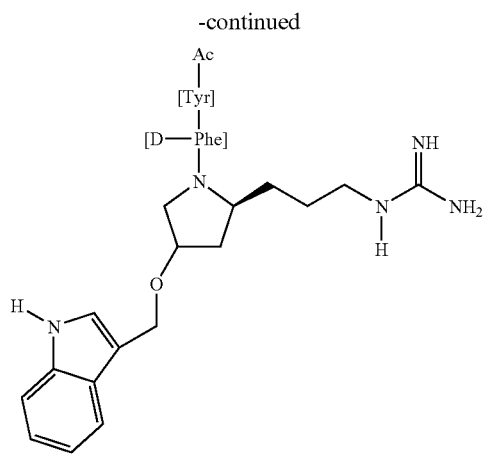
The following is a non-limiting description of several embodiments of the present invention. The following is a key to the succeeding tables of conformationally restricted MC-4, MC-3, and MC-4 and MC-3 receptor ligands.
The following are non-limiting examples of conformationally restricted rings indicating the position of the W, Y, and Z units.
A
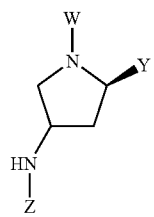
B
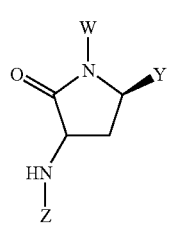
C
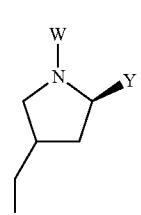
D
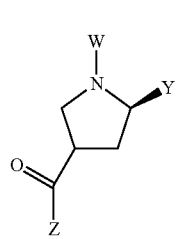
E
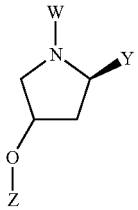
F
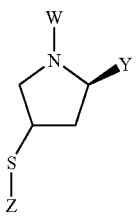
G
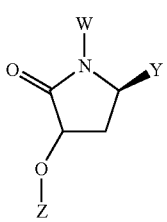
H
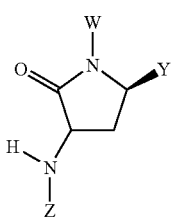
I
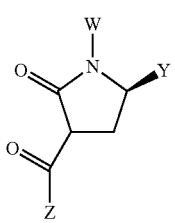
J
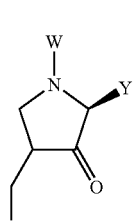
K
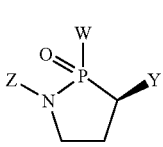

-continued

L 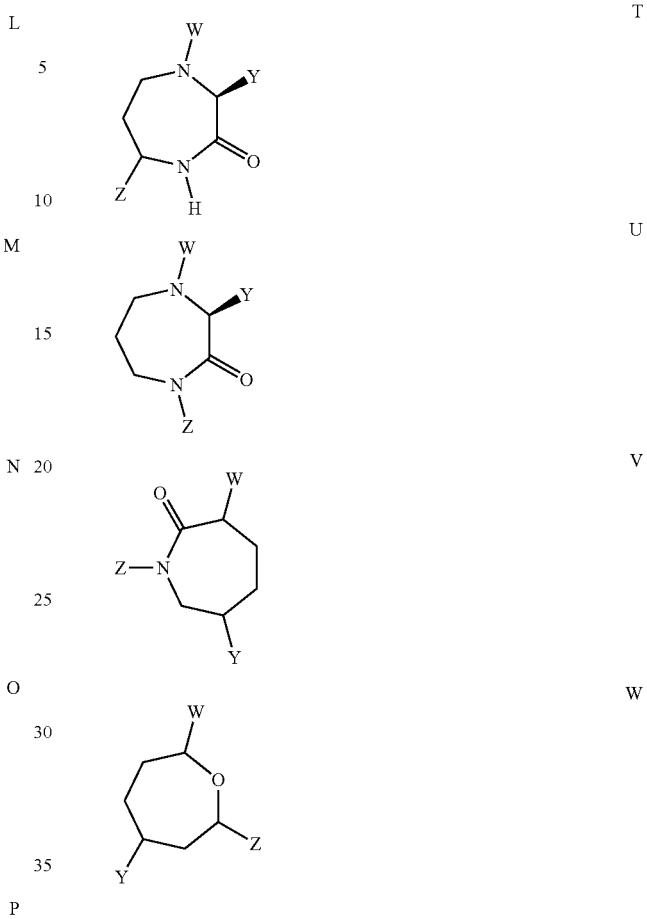

M

N

O

P

One embodiment of the present invention comprises 3-guanidinopropyl Y units attached to rings A-W, however, another aspect of the present invention substitutes the following Y units for 3-guanidinopropyl. Y units are selected from the group consisting of:

i) —$(CH_2)_3NHC(=NH)NH_2$;
ii) —$(CH_2)_4NHC(=NH)NH_2$;
iii) —$(CH_2)_5NHC(=NH)NH_2$;
iv) —$(CH_2)_3C(=NH)NH_2$;
v) —$(CH_2)_4C(=NH)NH_2$;
vi) —$(CH_2)_5C(=NH)NH_2$;
vii) —$(CH_2)_3NH_2$;
viii) —$(CH_2)_4NH_2$;
ix) —$(CH_2)_5NH_2$;
x) —$(CH_2)_6NH_2$.

The first category of receptor ligand analogs according to the present invention relates to conformationally restricted rings comprising a pyrrolidine scaffold having the formula:

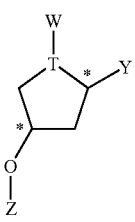

-continued

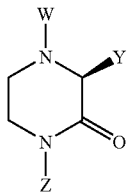
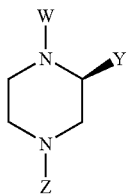
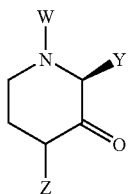
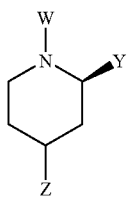
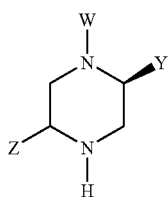
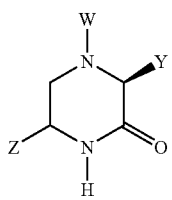
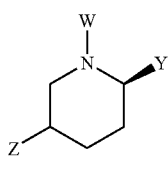
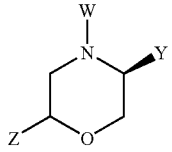

wherein each carbon indicated with an asterisk can have any configuration. Table I relates to non-limiting examples of analogs comprising a first aspect of this category, said analogs having the formula:

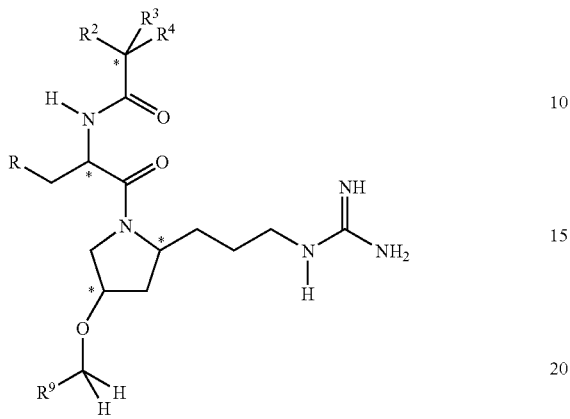

wherein R, $R^2$, $R^3$, $R^4$, and $R^9$ are defined in Table I, however, the 3-aminopropyl intermediates as described in Example 1 are also suitable receptor ligand analogs and represent an iteration of this aspect of the present invention.

TABLE I

| No. | R | $R^2$ | $R^3$ | $R^4$ | $R^9$ |
|---|---|---|---|---|---|
| 1 | phenyl | —NHC(O)CH$_3$ | H | benzyl | phenyl |
| 2 | benzyl | —NHC(O)CH$_3$ | H | benzyl | phenyl |
| 3 | 3-fluorophenyl | —NHC(O)CH$_3$ | H | benzyl | phenyl |
| 4 | 4-fluorophenyl | —NHC(O)CH$_3$ | H | benzyl | phenyl |
| 5 | 3,5-difluorophenyl | —NHC(O)CH$_3$ | H | benzyl | phenyl |
| 6 | 4-chlorophenyl | —NHC(O)CH$_3$ | H | benzyl | phenyl |
| 7 | 4-hydroxyphenyl | —NHC(O)CH$_3$ | H | benzyl | phenyl |
| 8 | phenyl | —NHC(O)CH$_3$ | H | 4-imidazolylmethyl | phenyl |
| 9 | benzyl | —NHC(O)CH$_3$ | H | 4-imidazolylmethyl | phenyl |
| 10 | 3-fluorophenyl | —NHC(O)CH$_3$ | H | 4-imidazolylmethyl | phenyl |
| 11 | 4-fluorophenyl | —NHC(O)CH$_3$ | H | 4-imidazolylmethyl | phenyl |
| 12 | 3,5-difluorophenyl | —NHC(O)CH$_3$ | H | 4-imidazolylmethyl | phenyl |
| 13 | 4-chlorophenyl | —NHC(O)CH$_3$ | H | 4-imidazolylmethyl | phenyl |
| 14 | 4-hydroxyphenyl | —NHC(O)CH$_3$ | H | 4-imidazolylmethyl | phenyl |
| 15 | phenyl | —NHC(O)CH$_3$ | H | 4-chlorobenzyl | phenyl |
| 16 | benzyl | —NHC(O)CH$_3$ | H | 4-chlorobenzyl | phenyl |
| 17 | 3-fluorophenyl | —NHC(O)CH$_3$ | H | 4-chlorobenzyl | phenyl |
| 18 | 4-fluorophenyl | —NHC(O)CH$_3$ | H | 4-chlorobenzyl | phenyl |
| 19 | 3,5-difluorophenyl | —NHC(O)CH$_3$ | H | 4-chlorobenzyl | phenyl |
| 20 | 4-chlorophenyl | —NHC(O)CH$_3$ | H | 4-chlorobenzyl | phenyl |
| 21 | 4-hydroxyphenyl | —NHC(O)CH$_3$ | H | 4-chlorobenzyl | phenyl |
| 22 | phenyl | —NHC(O)CH$_3$ | H | 4-hydroxybenzyl | phenyl |
| 23 | benzyl | —NHC(O)CH$_3$ | H | 4-hydroxybenzyl | phenyl |
| 24 | 3-fluorophenyl | —NHC(O)CH$_3$ | H | 4-hydroxybenzyl | phenyl |
| 25 | 4-fluorophenyl | —NHC(O)CH$_3$ | H | 4-hydroxybenzyl | phenyl |
| 26 | 3,5-difluorophenyl | —NHC(O)CH$_3$ | H | 4-hydroxybenzyl | phenyl |
| 27 | 4-chlorophenyl | —NHC(O)CH$_3$ | H | 4-hydroxybenzyl | phenyl |
| 28 | 4-hydroxyphenyl | —NHC(O)CH$_3$ | H | 4-hydroxybenzyl | phenyl |
| 29 | phenyl | —NHC(O)CH$_3$ | H | benzyl | 2-naphthyl |
| 30 | benzyl | —NHC(O)CH$_3$ | H | benzyl | 2-naphthyl |
| 31 | 3-fluorophenyl | —NHC(O)CH$_3$ | H | benzyl | 2-naphthyl |
| 32 | 4-fluorophenyl | —NHC(O)CH$_3$ | H | benzyl | 2-naphthyl |
| 33 | 3,5-difluorophenyl | —NHC(O)CH$_3$ | H | benzyl | 2-naphthyl |
| 34 | 4-chlorophenyl | —NHC(O)CH$_3$ | H | benzyl | 2-naphthyl |
| 35 | 4-hydroxyphenyl | —NHC(O)CH$_3$ | H | benzyl | 2-naphthyl |
| 36 | phenyl | —NHC(O)CH$_3$ | H | 4-imidazolylmethyl | 2-naphthyl |
| 37 | benzyl | —NHC(O)CH$_3$ | H | 4-imidazolylmethyl | 2-naphthyl |
| 38 | 3-fluorophenyl | —NHC(O)CH$_3$ | H | 4-imidazolylmethyl | 2-naphthyl |
| 39 | 4-fluorophenyl | —NHC(O)CH$_3$ | H | 4-imidazolylmethyl | 2-naphthyl |
| 40 | 3,5-difluorophenyl | —NHC(O)CH$_3$ | H | 4-imidazolylmethyl | 2-naphthyl |
| 41 | 4-chlorophenyl | —NHC(O)CH$_3$ | H | 4-imidazolylmethyl | 2-naphthyl |
| 42 | 4-hydroxyphenyl | —NHC(O)CH$_3$ | H | 4-imidazolylmethyl | 2-naphthyl |

TABLE I-continued

| No. | R | $R^2$ | $R^3$ | $R^4$ | $R^9$ |
|---|---|---|---|---|---|
| 43 | phenyl | —NHC(O)CH$_3$ | H | 4-chlorobenzyl | 2-naphthyl |
| 44 | benzyl | —NHC(O)CH$_3$ | H | 4-chlorobenzyl | 2-naphthyl |
| 45 | 3-fluorophenyl | —NHC(O)CH$_3$ | H | 4-chlorobenzyl | 2-naphthyl |
| 46 | 4-fluorophenyl | —NHC(O)CH$_3$ | H | 4-chlorobenzyl | 2-naphthyl |
| 47 | 3,5-difluorophenyl | —NHC(O)CH$_3$ | H | 4-chlorobenzyl | 2-naphthyl |
| 48 | 4-chlorophenyl | —NHC(O)CH$_3$ | H | 4-chlorobenzyl | 2-naphthyl |
| 49 | 4-hydroxyphenyl | —NHC(O)CH$_3$ | H | 4-chlorobenzyl | 2-naphthyl |
| 50 | phenyl | —NHC(O)CH$_3$ | H | 4-hydroxybenzyl | 2-naphthyl |
| 51 | benzyl | —NHC(O)CH$_3$ | H | 4-hydroxybenzyl | 2-naphthyl |
| 52 | 3-fluorophenyl | —NHC(O)CH$_3$ | H | 4-hydroxybenzyl | 2-naphthyl |
| 53 | 4-fluorophenyl | —NHC(O)CH$_3$ | H | 4-hydroxybenzyl | 2-naphthyl |
| 54 | 3,5-difluorophenyl | —NHC(O)CH$_3$ | H | 4-hydroxybenzyl | 2-naphthyl |
| 55 | 4-chlorophenyl | —NHC(O)CH$_3$ | H | 4-hydroxybenzyl | 2-naphthyl |
| 56 | 4-hydroxyphenyl | —NHC(O)CH$_3$ | H | 4-hydroxybenzyl | 2-naphthyl |
| 57 | 4-fluorophenyl | H | H | benzyl | 2-naphthyl |
| 58 | phenyl | H | H | benzyl | 2-naphthyl |
| 59 | 4-fluorophenyl | H | H | 4-hydroxybenzyl | 2-naphthyl |
| 60 | phenyl | —NHC(O)CH$_3$ | H | 2-naphthylmethyl | 2-naphthyl |

The following is an outline of a synthetic pathway for preparing analogs 1–60, however other embodiments of the pyrrolidone scaffold can be prepared using modifications to this general scheme.

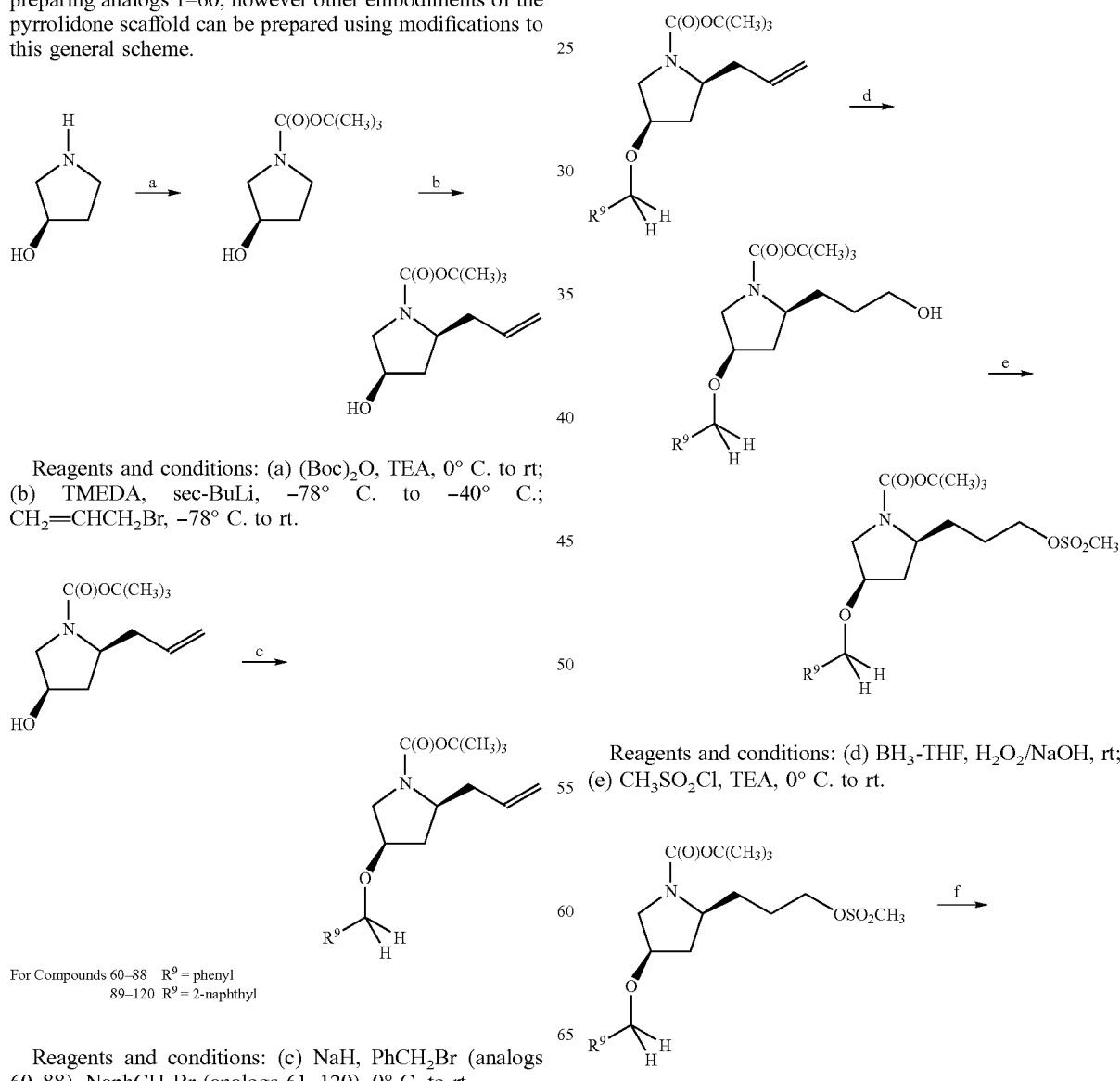

Reagents and conditions: (a) (Boc)$_2$O, TEA, 0° C. to rt; (b) TMEDA, sec-BuLi, −78° C. to −40° C.; CH$_2$=CHCH$_2$Br, −78° C. to rt.

For Compounds 60–88   $R^9$ = phenyl
89–120   $R^9$ = 2-naphthyl

Reagents and conditions: (c) NaH, PhCH$_2$Br (analogs 60–88), NaphCH$_2$Br (analogs 61–120), 0° C. to rt.

Reagents and conditions: (d) BH$_3$-THF, H$_2$O$_2$/NaOH, rt; (e) CH$_3$SO$_2$Cl, TEA, 0° C. to rt.

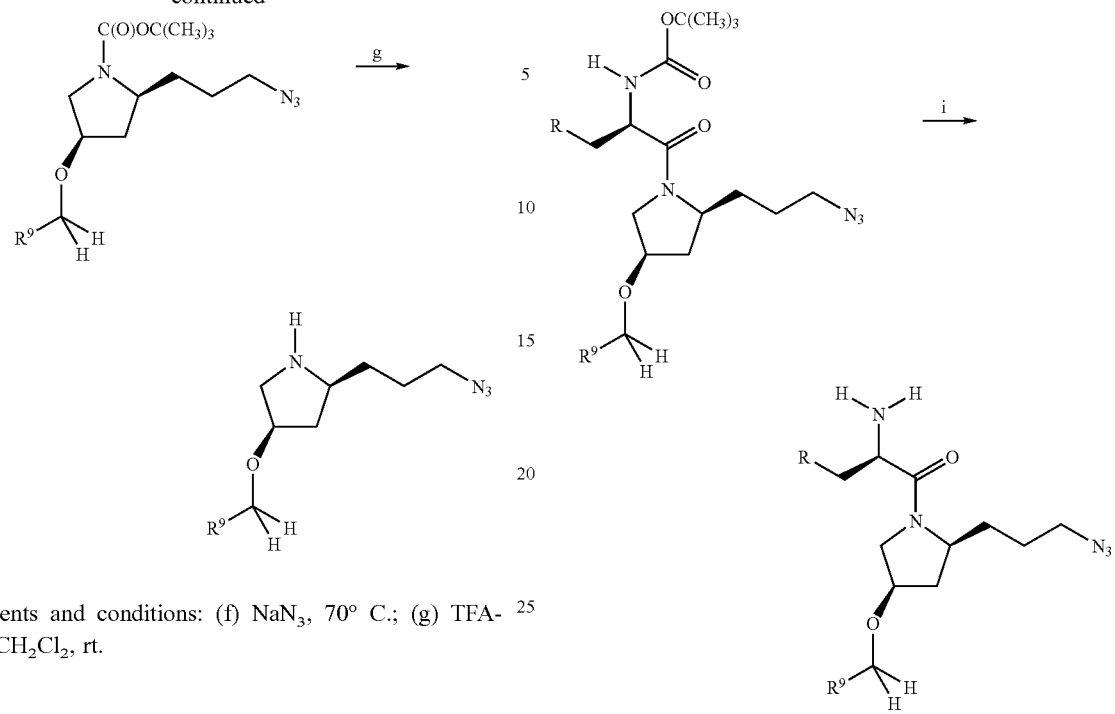

Reagents and conditions: (f) NaN₃, 70° C.; (g) TFA-H₂O—CH₂Cl₂, rt.

Reagents and conditions: (h) Boc-D-Phe (analogs 1, 8, 15, 22, 29, 36, 43, 50, 58, and 60), Boc-homo-D-Phe (analogs 2, 9, 16, 23, 30, 37, 44, and 51), Boc-D-Phe(3-F) (analogs 3, 10, 17, 24, 31, 38, 45, and 52), Boc-D-Phe(4-F) (analogs 4, 11, 18, 25, 32, 39, 46, 53, 57, and 59), Boc-D-Phe(3,5-F) (analogs 5, 12, 19, 26, 33, 40, 47, and 54), Boc-D-Phe(4-Cl) (analogs 6, 13, 20, 27, 34, 41, 48, and 55), Boc-D-Phe(4-OH) (analogs 7, 14, 21, 28, 35, 42, 49, and 56); 1-hydroxybenzotriazole, N-methylmorpholine, 1-(3-dimethylaminopropyl)-3-ethylcarbodiimide, rt.

Reagents and conditions: (i) TFA-H₂O—CH₂Cl₂, rt.

Reagents and conditions: (j) AcNHCH(CH₂Phe)CO₂H (analogs 1–7, 29–35, 57, and 58); N-Ac-histidine (analogs 8–14, and 36–42; AcNHCH[CH₂Phe(4-Cl)]CO₂H (analogs 15–21, 43–49), N-Ac-tyrosine (analogs 22–28, 50–56, and 59); AcNHCH(CH₂Naph)CO₂H (analog 60); 1-hydroxybenzotriazole, N-methylmorpholine, 1-(3-dimethylaminopropyl)-3-ethylcarbodiimide, rt.

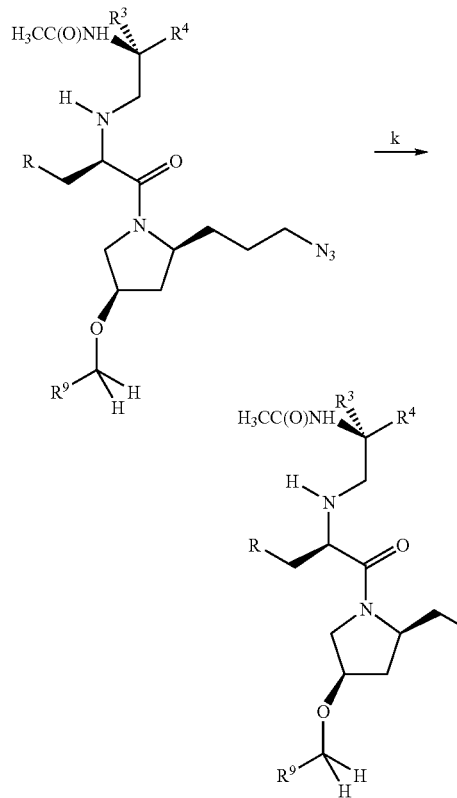

Reagents and conditions: (k) H₂, Pd/C.

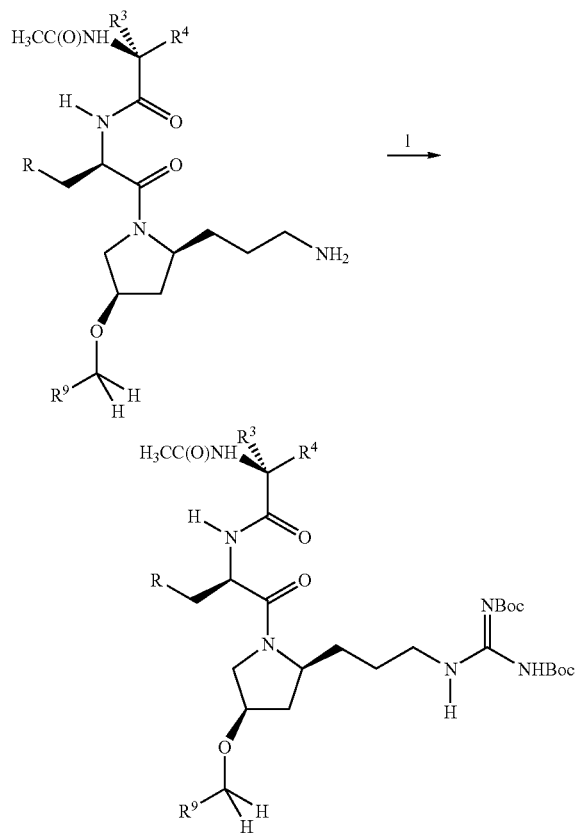

Reagents and conditions: (l) BocNHC(SCH₃)=NBoc, HgCl₂, rt.

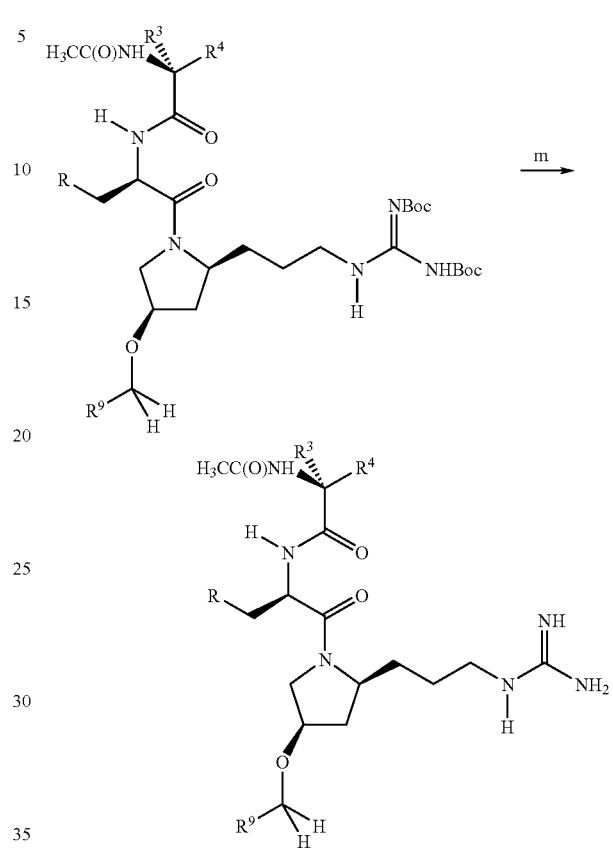

Reagents and conditions: (m) TFA:CH₂Cl₂:anisole, rt.

Preparation of Pyrrolidine Synthetic Intermediate

The following is a procedure for preparing the pyrrolidine scaffold intermediate having the formula:

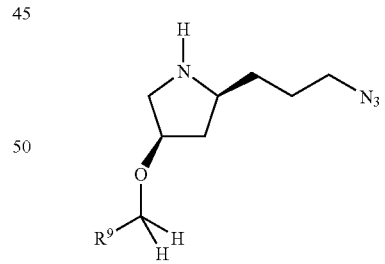

wherein for this example R⁹ is a 2-naphthyl moiety.

2-S-(3-Azidopropyl)-4-R-(naphthalen-2-ylmethoxy)-pyrrolidine

Preparation of N-Boc-3-R-hydroxypyrrolidine, (1): Di-tert-butyl dicarbonate (14.0 g, 63.1 mmol) is added to a stirred solution of 3-R-hydroxypyrrolidine (5.0 g, 57.4 mol) and triethylamine (16 mL, 114.8 mmol) dissolved in dichloromethane (58 ml) at 0° C. The resulting solution is allowed to warm to room temperature and stirred for 4 hours. The solution is then diluted with dichloromethane (50 mL), washed twice with 1 N HCl and twice with aq. NaHCO$_3$ solution. The organic layer is then dried over Na$_2$SO$_4$, filtered and concentrated in vacuo to give the desired product (9.9 g, 92%) as a white solid which is sufficiently pure for use without further purification.

Preparation of N-Boc-2-S-allyl-4-R-hydroxypyrrolidine, (2): A solution of N-Boc-3-R-hydroxypyrrolidine, 1, (3.0 g, 16.0 mmol), and TMEDA (6.4 mL, 40.1 mmol) is dissolved in THF (50 mL) and cooled to −78° C. To this reaction mixture is added a solution of 1.3 M sec-butyl lithium (50 mL) in cyclohexanes with stirring. The resulting orange-colored mixture is allowed to warm to −40° C. and stirred for 2.75 hours. The mixture is again cooled to −78° C. and allyl bromide (3.1 mL, 35.3 mmol) is added. This mixture is slowly warmed to room temperature with stirring over 4.5 hours. The reaction is quenched with aq. NH$_4$Cl solution and extracted with ethyl acetate (150 mL). The organic layer is then dried over Na$_2$SO$_4$, filtered and concentrated in vacuo. The oily residue is purified over silica gel (CH$_2$Cl$_2$/acetone, 3:1) to afford the desired product (2.0 g, 56%) as a clear oil.

Preparation of N-Boc-2-S-allyl-4-R-(naphthalen-2-ylmethoxy)pyrrolidine, (3): Sodium hydride (408 mg, 11.5 mmol) is added in portions to a stirred solution of N-Boc-2-S-allyl-4-R-hydroxypyrrolidine, 2, (2.0 g, 8.8 mmol) in DMF at 0° C. and the reaction mixture is stirred for 20 min. 2-(Bromomethyl)naphthalene (2.9 g, 13.2 mmol) in DMF (5 mL) is then added and the resulting solution is stirred for 5 hours at room temperature. The reaction is quenched with aq. NH$_4$Cl solution and extracted twice with ethyl acetate. The combined organic layers are dried over Na$_2$SO$_4$, filtered and concentrated in vacuo to a yellow oil. The oil residue is purified over silica gel (hexanes/EtOAc, 6:1) to afford the desired product (2.7 g, 84%) as a clear oil.

Preparation of N-Boc-2-S-(3-hydroxypropyl)-4-R-(naphthalen-2-ylmethoxy)pyrrolidine (4): A 1.0 M solution of borane-tetrahydrofuran complex in THF (11 mL, 11 mmol) is slowly added to a solution of N-Boc-2-S-allyl-4-R-(naphthalen-2-ylmethoxy)pyrrolidine, 3, (2.7 g, 7.3 mmol) in THF (15 mL) and the reaction mixture is stirred for 0.5 hour, after which H$_2$O (4.1 ml) is carefully added followed by the addition of 3.0 M NaOH (7.3 mL) and 33% H$_2$O$_2$ (5.0 mL). This mixture is stirred for 2 hours and then is extracted with EtOAc (50 ml). The organic layer is dried over Na$_2$SO$_4$, filtered and concentrated in vacuo to a yellow oil. The oily residue is purified over silica gel (hexanes/EtOAc, 1:1) to afford the desired product (712 mg) as an oil.

Preparation of N-Boc-2-S-(3-methanesulfonyloxypropyl)-4-R-(naphthalen-2-ylmethoxy)pyrrolidine (5): Methane sulfonyl chloride (0.215 mL, 2.8 mmol) is added to a stirred solution of N-Boc-2-S-(3-hydroxypropyl)-4-R-(naphthalen-2-ylmethoxy)pyrrolidine, 4, (712 mg, and triethylamine (0.39 mL, 2.8 mmol) in dichloromethane (6 mL) at 0° C., and the reaction mixture is then stirred at room temperature for 0.75 hour. The reaction is quenched with saturated aq. NaHCO$_3$ solution and extracted twice with dichloromethane (25 mL). The combined organic layers are dried over Na$_2$SO$_4$, filtered and concentrated in vacuo to afford the desired product (856 mg, 100%) as an oil which is sufficiently pure for use without further purification.

Preparation of N-Boc-2-S-(3-azidopropyl)-4-R-(naphthalen-2-ylmethoxy)pyrrolidine (6): Sodium azide (361 mg, 5.50 mmol) is added to a solution of N-Boc-2-S-(3-methanesulfonyloxypropyl)-4-R-(naphthalen-2-ylmethoxy)pyrrolidine, 5, (856 mg, 1.85 mmol) in DMSO (7 mL) and the reaction mixture is stirred at 70° C. for 3 hours. The reaction is quenched with H$_2$O and extracted with EtOAc (30 mL). The extract is dried over Na$_2$SO$_4$, filtered and concentrated in vacuo to an orange-colored oil. The oily residue is purified over silica gel (hexanes/EtOAc, 3:1) to afford the desired product (584 mg, 78%) as a colorless oil.

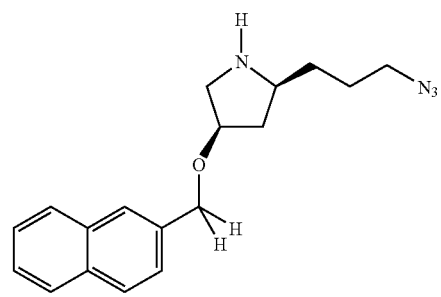

7

Preparation of 2-S-(3-azidopropyl)-4-R-(naphthalen-2-ylmethoxy)pyrrolidine (7): A prepared solution of TFA:H$_2$O:CH$_2$Cl$_2$ (1:0.1:1, 20 mL) is added to a round-bottomed flask charged with N-Boc-2-S-(3-azidopropyl)-4-R-(naphthalen-2-ylmethoxy)pyrrolidine, 6, (2.85 g, 6.95 mmol) and the reaction mixture is stirred for 1 hour. The mixture is concentrated in vacuo to give the desired product (3.0 g, 100%) as a TFA salt. The crude oil is carried forward as an intermediate in the synthesis of embodiments of the present invention without further purification.

The pyrrolidine synthetic intermediate having the formula:

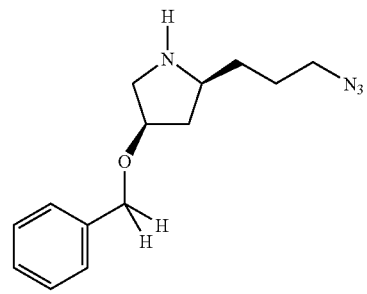

can be prepared by substituting benzyl bromide for 2-(bromomethyl)naphthalene under the conditions described herein above for the preparation of compound 3.

EXAMPLE 1

2-S-Acetylamino-N-{2-[2-S-(3-aminopropyl)-4-R-(naphthalen-2-ylmethoxy)pyrrolidin-1-yl]-1-R-benzyl-2-oxo-ethyl}-3-(4-hydroxyphenyl) propionamide (11)

Preparation of 2-S-N-(tert-butoxycarbonyl)amino-1-[2-(3-azidopropyl)-4-R-(naphthalen-2-ylmethoxy)-pyrrolidin-1-yl]-3-phenylpropan-1-one (8): To a solution of 2-S-(3-azidopropyl)-4-R-(naphthalen-2-ylmethoxy)pyrrolidine (1.0 g, 2.36 mmol), N-(tert-butoxycarbonyl)-D-phenylalanine (625 mg, 2.36 mmol), 1-hydroxybenzotriazole (641 mg, 4.72 mmol) and N-methylmorpholine (0.8 mL, 7.07 mmol) in DMF (9.4 mL) is added 1-(3-dimethylaminopropyl)-3-ethylcarbodiimide hydrochloride (506 mg, 2.83 mmol) and this mixture is stirred at room temperature for 1.25 hours.

The reaction is quenched with saturated aq. NH₄Cl solution and extracted with EtOAc (75 mL). The organic layer is washed with H₂O (100 mL), brine (100 mL), dried over Na₂SO₄, filtered and concentrated in vacuo to a brown-colored oil. The crude oil residue is purified by over silica gel (hexanes/EtOAc, 3:2) to give the desired product (986 mg, 75%) as a white solid.

Preparation of 2-S-amino-1-[2-(3-azidopropyl)-4-R-(naphthalen-2-ylmethoxy)pyrrolidin-1-yl]-3-phenylpropan-1-one (9): A solution of TFA:CH₂Cl₂:H₂O (1:1:0.1, 10 ml) is added to a round-bottomed flask charged with 2-S-N-(tert-butoxycarbonyl)-amino-1-[2-(3-azidopropyl)-4-R-(naphthalen-2-ylmethoxy)-pyrrolidin-1-yl]-3-phenylpropan-1-one, 8, (986 mg, 1.77 mmol), and reaction mixture is stirred at room temperature for 1.0 hour. The solution is concentrated to give the trifluoroacetic acid salt of the desired compound (1.0 g, 99%) as a clear oil, which is sufficiently pure to next reaction without purification.

Preparation of 2-S-acetylamino-N-{2-[2-S-(3-azidopropyl)-4-R-(naphthalen-2-ylmethoxy)pyrrolidin-1-yl]-1-R-benzyl-2-oxo-ethyl}-3-(4-hydroxyphenyl)propionamide (10): To a solution of 2-S-amino-1-[2-(3-azidopropyl)-4-R-(naphthalen-2-ylmethoxy)-pyrrolidin-1-yl]-3-phenylpropan-1-one, 9, (1.5 g, 2.63 mmol), N-acetyl-L-tyrosine (586 mg, 2.63 mmol), 1-hydroxybenzotriazole (709 mg, 5.25 mmol) and N-methylmorpholine (0.9 mL, 7.88 mmol) in DMF (8.8 mL) is added 1-(3-dimethylaminopropyl)-3-ethylcarbodiimide hydrochloride (564 mg, 3.15 mmol) and the reaction mixture is stirred at room temperature for 1 hour. The reaction is quenched with saturated aq. NH₄Cl and extracted twice with EtOAc (75 mL). The combined organic layers are washed with H₂O (80 mL), brine (80 mL), dried over Na₂SO₄, filtered and concentrated in vacuo to an oil. The crude oil is purified over silica gel (acetone/CH₂Cl₂, 3:2) to afford the desired compound (1.03 mg, 60%) as a white solid.

Preparation of 2-S-acetylamino-N-{2-[2-S-(3-aminopropyl)-4-R-(naphthalen-2-ylmethoxy)-pyrrolidin-1-yl]-1-R-benzyl-2-oxo-ethyl}-3-(4-hydroxyphenyl)propionamide (11): A solution of 2-S-acetylamino-N-{2-[2-S-(3-azidopropyl)-4-R-(naphthalen-2-ylmethoxy)-pyrrolidin-1-yl]-1-R-benzyl-2-oxo-ethyl}-3-(4-hydroxy-phenyl)-propionamide, 10, (1.03 g, 1.56 mmol) and pyridine (0.07 mL, 0.78 mmol) in methanol (5.0 mL) is purged with argon and 10% by weight palladium on carbon (500 mg) is then added. This reaction mixture is stirred in a hydrogen atmosphere for 5 hours. The reaction is then filtered through a pad of Celite to remove the catalyst and the filtrate is concentrated in vacuo to yield an embodiment of the present invention (871 mg, 88%) as a white solid.

This procedure can be used to make the 3-aminopropyl analogs which represent one iteration of the pyrrolidinyl scaffolds. The materials obtained at this point are sufficiently pure to be used directly for the preparation of guanidino-pyrrolidine analogs of the present invention.

EXAMPLE 2

2-S-Acetylamino-N-{2-[2-S-(3-guanidinopropyl)-4-R-(naphthalen-2-ylmethoxy)-pyrrolidin-1-yl]-1-R-benzyl-2-oxo-ethyl}-3-(4-hydroxyphenyl)propionamide (13)

Preparation of 2-S-acetylamino-N-{1-R-benzyl-2-[2-S-(3-N,N'-bis(tert-butoxycarbonyl)guanidinopropyl)-4-R-(naphthalen-2-ylmethoxy)-pyrrolidin-1-yl]-2-oxo-ethyl}-3-(4-hydroxyphenyl)-propionamide (12): Mercury(II) chloride (113 mg, 0.24 mmol) is added to a solution of 2-S-acetylamino-N-{2-[2-S-(3-aminopropyl)-4-R-(naphthalen-2-ylmethoxy)pyrrolidin-1-yl]-1-R-benzyl-2-oxo-ethyl}-3-(4-hydroxyphenyl)propionamide, 11, (125 mg, 0.20 mmol), 1,3-bis(tert-butoxycarbonyl)-2-methyl-2-thiopseudo urea (57 mg, 0.2 mmol) and triethylamine (0.1 mL, 0.59 mmol) in dry DMF (2 mL) and the reaction mixture is stirred at 0° C. for 1 hour. The reaction mixture is then diluted with EtOAc, filtered through a pad of Celite, and the filtrate is concentrated in vacuo to afford the crude product as an oil. The crude isolate is purified over silica gel (CH₂Cl₂/methanol, 14:1) to afford the desired product (170 mg, 98%) as a white solid.

Preparation of 2-S-acetylamino-N-{1-benzyl-2-[2-S-(3-guanidinopropyl)-4-R-(naphthalen-2-ylmethoxy)pyrrolidin-1-yl]-2-oxo-ethyl}-3-(4-hydroxyphenyl)propionamide (13): A solution of TFA:CH₂Cl₂:anisole (40:55:5, 3.0 mL) is added to a round-bottomed flask charged with 2-S-Acetylamino-N-{1-R-benzyl-2-[2-S-(3-N,N'-bis(tert-butoxycarbonyl)guanidinopropyl)-4-R-(naphthalen-2-ylmethoxy)pyrrolidin-1-yl]-2-oxo-ethyl}-3-(4-hydroxyphenyl) propionamide, 12, (170 mg, 0.19 mmol) and the reaction mixture is stirred for 3.25 hours. The reaction mixture is then diluted with dichloroethane and concentrated in vacuo. The crude product is purified by reverse phase prep HPLC to give embodiment No. 50 from TABLE I (57 mg, 44%) as a white powder.

Another category of receptor ligand analogs according to the present invention relates to conformationally restricted rings comprising a piperidine scaffold having the formula:

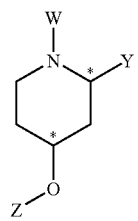

wherein each carbon indicated with an asterisk can have any configuration. Table II relates to non-limiting examples of analogs comprising a first aspect of this category, said analogs having the formula:

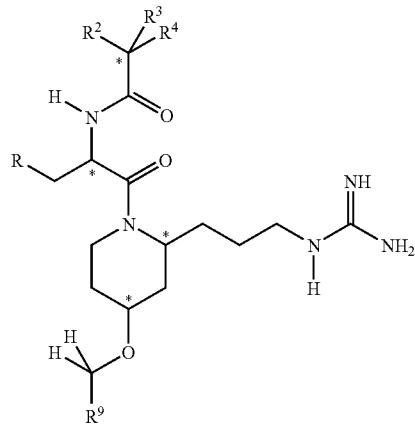

wherein R, R², R³, and R⁹ are defined in Table II.

TABLE II

| No. | R | $R^2$ | $R^3$ | $R^4$ | $R^9$ |
|---|---|---|---|---|---|
| 61 | phenyl | —NHC(O)CH$_3$ | H | benzyl | phenyl |
| 62 | 4-chlorophenyl | —NHC(O)CH$_3$ | H | benzyl | phenyl |
| 63 | 4-fluorophenyl | —NHC(O)CH$_3$ | H | benzyl | phenyl |
| 64 | 3,4-difluorophenyl | —NHC(O)CH$_3$ | H | benzyl | phenyl |
| 65 | phenyl | —NHC(O)CH$_3$ | H | 2-imidazolylmethyl | phenyl |
| 66 | 4-chlorophenyl | —NHC(O)CH$_3$ | H | 2-imidazolylmethyl | phenyl |
| 67 | 4-fluorophenyl | —NHC(O)CH$_3$ | H | 2-imidazolylmethyl | phenyl |
| 68 | 3,4-difluorophenyl | —NHC(O)CH$_3$ | H | 2-imidazolylmethyl | phenyl |
| 69 | phenyl | —NHC(O)CH$_3$ | H | 4-imidazolylmethyl | phenyl |
| 70 | 4-chlorophenyl | —NHC(O)CH$_3$ | H | 4-imidazolylmethyl | phenyl |
| 71 | 4-fluorophenyl | —NHC(O)CH$_3$ | H | 4-imidazolylmethyl | phenyl |
| 72 | 3,4-difluorophenyl | —NHC(O)CH$_3$ | H | 4-imidazolylmethyl | phenyl |
| 73 | phenyl | —NHC(O)CH$_3$ | H | 4-fluorobenzyl | phenyl |
| 74 | 4-chlorophenyl | —NHC(O)CH$_3$ | H | 4-fluorobenzyl | phenyl |
| 75 | 4-fluorophenyl | —NHC(O)CH$_3$ | H | 4-fluorobenzyl | phenyl |
| 76 | 3,4-difluorophenyl | —NHC(O)CH$_3$ | H | 4-fluorobenzyl | phenyl |
| 77 | phenyl | —NHC(O)CH$_3$ | H | 4-hydroxybenzyl | phenyl |
| 78 | 4-chlorophenyl | —NHC(O)CH$_3$ | H | 4-hydroxybenzyl | phenyl |
| 79 | 4-fluorophenyl | —NHC(O)CH$_3$ | H | 4-hydroxybenzyl | phenyl |
| 80 | 3,4-difluorophenyl | —NHC(O)CH$_3$ | H | 4-hydroxybenzyl | phenyl |
| 81 | phenyl | —NHC(O)CH$_3$ | H | 4-chlorobenzyl | phenyl |
| 82 | 4-chlorophenyl | —NHC(O)CH$_3$ | H | 4-chlorobenzyl | phenyl |
| 83 | 4-fluorophenyl | —NHC(O)CH$_3$ | H | 4-chlorobenzyl | phenyl |
| 84 | 3,4-difluorophenyl | —NHC(O)CH$_3$ | H | 4-chlorobenzyl | phenyl |
| 85 | phenyl | —NHC(O)CH$_3$ | H | 4-acetoxybenzyl | phenyl |
| 86 | 4-chlorophenyl | —NHC(O)CH$_3$ | H | 4-acetoxybenzyl | phenyl |
| 87 | 4-fluorophenyl | —NHC(O)CH$_3$ | H | 4-acetoxybenzyl | phenyl |
| 88 | 3,4-difluorophenyl | —NHC(O)CH$_3$ | H | 4-acetoxybenzyl | phenyl |
| 89 | phenyl | —NHC(O)CH$_3$ | H | benzyl | 2-naphthyl |
| 90 | 4-chlorophenyl | —NHC(O)CH$_3$ | H | benzyl | 2-naphthyl |
| 91 | 4-fluorophenyl | —NHC(O)CH$_3$ | H | benzyl | 2-naphthyl |
| 92 | 3,4-difluorophenyl | —NHC(O)CH$_3$ | H | benzyl | 2-naphthyl |
| 93 | phenyl | —NHC(O)CH$_3$ | H | 2-imidazolylmethyl | 2-naphthyl |
| 94 | 4-chlorophenyl | —NHC(O)CH$_3$ | H | 2-imidazolylmethyl | 2-naphthyl |
| 95 | 4-fluorophenyl | —NHC(O)CH$_3$ | H | 2-imidazolylmethyl | 2-naphthyl |
| 96 | 3,4-difluorophenyl | —NHC(O)CH$_3$ | H | 2-imidazolylmethyl | 2-naphthyl |
| 97 | phenyl | —NHC(O)CH$_3$ | H | 4-imidazolylmethyl | 2-naphthyl |
| 98 | 4-chlorophenyl | —NHC(O)CH$_3$ | H | 4-imidazolylmethyl | 2-naphthyl |
| 99 | 4-fluorophenyl | —NHC(O)CH$_3$ | H | 4-imidazolylmethyl | 2-naphthyl |
| 100 | 3,4-difluorophenyl | —NHC(O)CH$_3$ | H | 4-imidazolylmethyl | 2-naphthyl |
| 101 | phenyl | —NHC(O)CH$_3$ | H | 4-fluorobenzyl | 2-naphthyl |
| 102 | 4-chlorophenyl | —NHC(O)CH$_3$ | H | 4-fluorobenzyl | 2-naphthyl |
| 102 | 4-fluorophenyl | —NHC(O)CH$_3$ | H | 4-fluorobenzyl | 2-naphthyl |
| 104 | 3,4-difluorophenyl | —NHC(O)CH$_3$ | H | 4-fluorobenzyl | 2-naphthyl |
| 105 | phenyl | —NHC(O)CH$_3$ | H | 4-hydroxybenzyl | 2-naphthyl |
| 106 | 4-chlorophenyl | —NHC(O)CH$_3$ | H | 4-hydroxybenzyl | 2-naphthyl |
| 107 | 4-fluorophenyl | —NHC(O)CH$_3$ | H | 4-hydroxybenzyl | 2-naphthyl |
| 108 | 3,4-difluorophenyl | —NHC(O)CH$_3$ | H | 4-hydroxybenzyl | 2-naphthyl |
| 109 | phenyl | —NHC(O)CH$_3$ | H | 4-chlorobenzyl | 2-naphthyl |
| 110 | 4-chlorophenyl | —NHC(O)CH$_3$ | H | 4-chlorobenzyl | 2-naphthyl |
| 111 | 4-fluorophenyl | —NHC(O)CH$_3$ | H | 4-chlorobenzyl | 2-naphthyl |
| 112 | 3,4-difluorophenyl | —NHC(O)CH$_3$ | H | 4-chlorobenzyl | 2-naphthyl |
| 113 | phenyl | —NHC(O)CH$_3$ | H | 4-acetoxybenzyl | 2-naphthyl |
| 114 | 4-chlorophenyl | —NHC(O)CH$_3$ | H | 4-acetoxybenzyl | 2-naphthyl |
| 115 | 4-fluorophenyl | —NHC(O)CH$_3$ | H | 4-acetoxybenzyl | 2-naphthyl |
| 116 | 3,4-difluorophenyl | —NHC(O)CH$_3$ | H | 4-acetoxybenzyl | 2-naphthyl |
| 117 | phenyl | H | H | benzyl | 2-naphthyl |
| 118 | 4-chlorophenyl | H | H | benzyl | 2-naphthyl |
| 119 | 4-fluorophenyl | H | H | benzyl | 2-naphthyl |
| 120 | 3,4-difluorophenyl | H | H | benzyl | 2-naphthyl |

The following is an outline of a synthetic pathway for preparing analogs 61–120, however, other embodiments of the piperidine scaffold can be prepared using modifications to this general scheme.

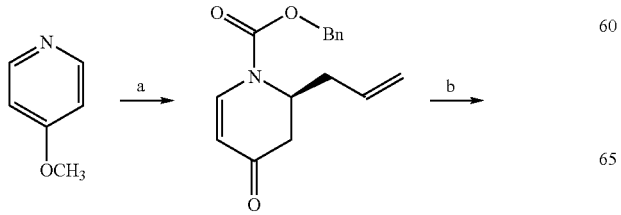

-continued

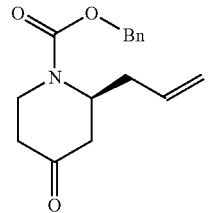

Reagents and conditions: (a) CbzCl, 0° C.; CH$_2$=CHCH$_2$MgCl, −78° C. to 0° C.; (b) Zn/HOAc.

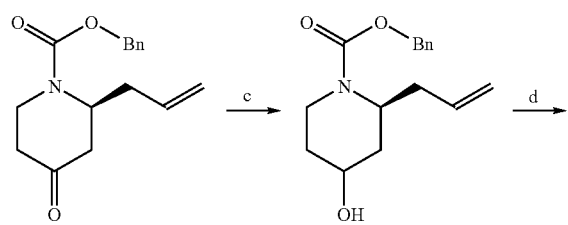

For Compounds 1–28 R$^9$=phenyl 29–60 R$^9$=2-naphthyl
Reagents and conditions: (c) K-selectride, 10° C.; (d) NaH, PhCH$_2$Br (cpds 1–28), NaphCH$_2$Br (analogs 89–120), 0° C. to rt.

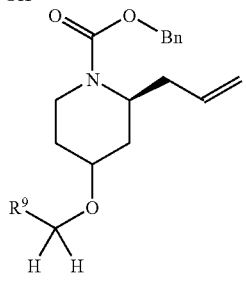

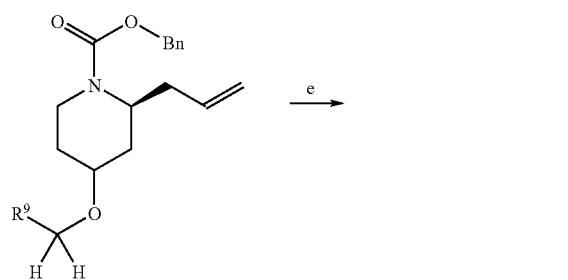

Reagents and conditions: (e) BH$_3$-THF, H$_2$O$_2$/NaOH, 0° C. to rt.

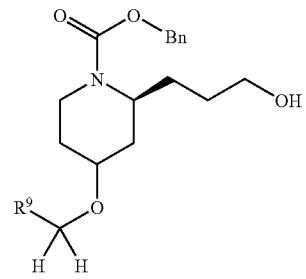

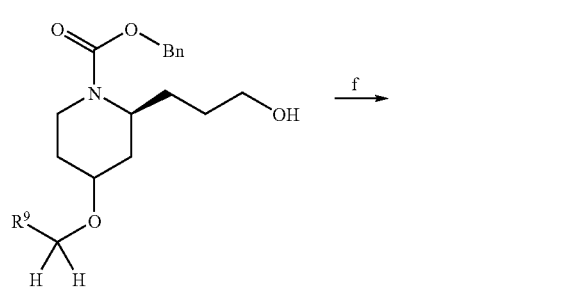

-continued

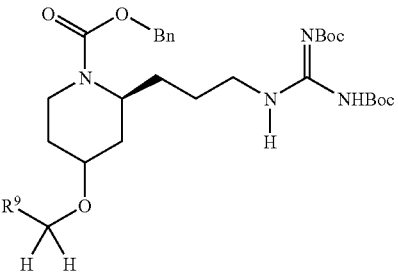

Reagents and conditions: (f) (BocNH)$_2$C=NH, diisopropyl azodicarboxylate Ph$_3$P, 0° C. to rt.

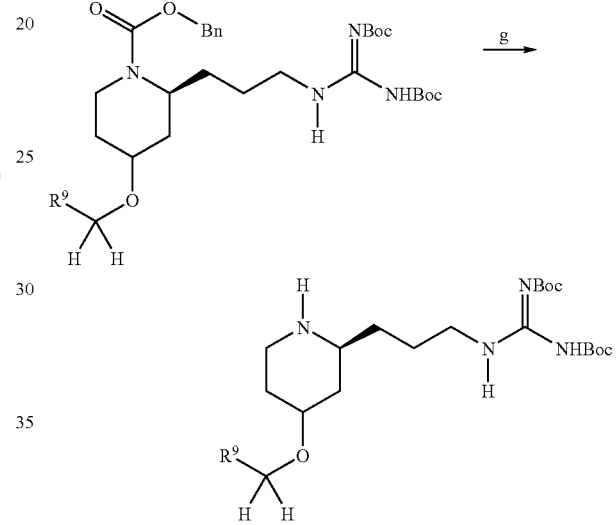

Reagents and conditions: (g) H$_2$, Pd/C, pyridine, rt.

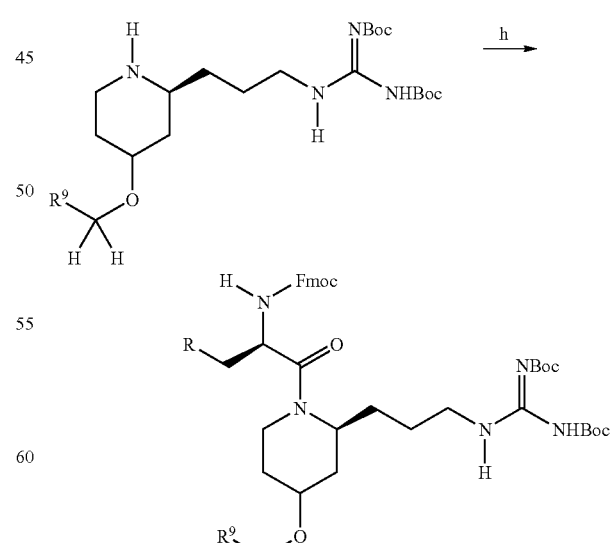

Reagents and conditions: (h) Fmoc-D-phenylalanine (analogs 61, 65, 69, 73, 77, 71, 85, 89, 93, 97, 101, 105, 109, 113, and 57), Fmoc-D-(4-chloro)phenylalanine (analogs 62, 66, 70, 74, 78, 82, 86, 90, 94, 98, 102, 106, 110, 114, and 118), Fmoc-D-(4-fluoro)phenylalanine (analogs 63, 67, 71, 75, 79, 83, 87, 91, 95, 99, 103, 107, 111, 115, and 119), Fmoc-D-(3,4-difluoro)phenylalanine (analogs 64, 68, 72, 76, 80, 84, 88, 92, 96, 100, 104, 108, 112, 116, and 120), (i-propyl)$_2$NEt, PyBroP, −20° C.

Reagents and conditions: (j) EDCI, HOBt, N-acetyl-L-Phenylalanine (analogs 61–64, 89–92, and 117–120), N-acetyl-(2-imidazolinyl)-L-histidine (analogs 65–68 and 93–96), N-acetyl-L-histidine (analogs 69–72 and 97–100), N-acetyl-L-(4-fluoro)phenylalanine (analogs 73–76 and 101–104), N-acetyl-L-tyrosine (analogs 77–80 and 105–108), N-acetyl-L-(4-chloro)phenylalanine (cpds 81–84 and 109–112), N-acetyl-L-(4-acetyl)tyrosine (analogs 85–88 and 113–116).

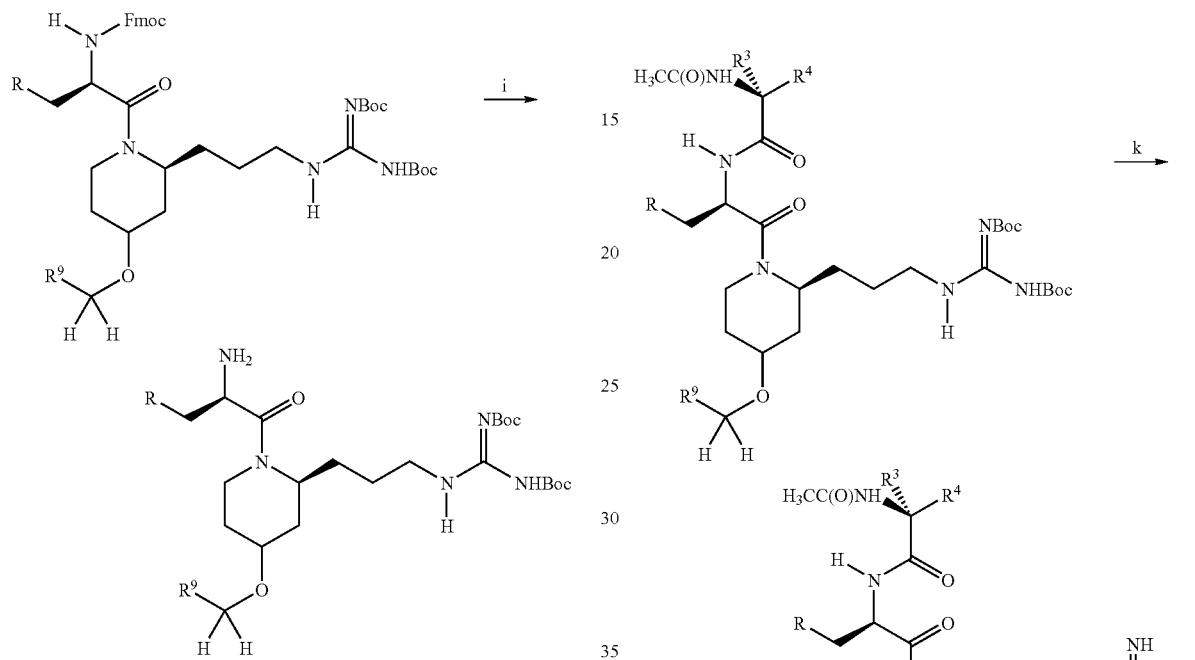

Reagents and conditions: (i) piperidine, rt.

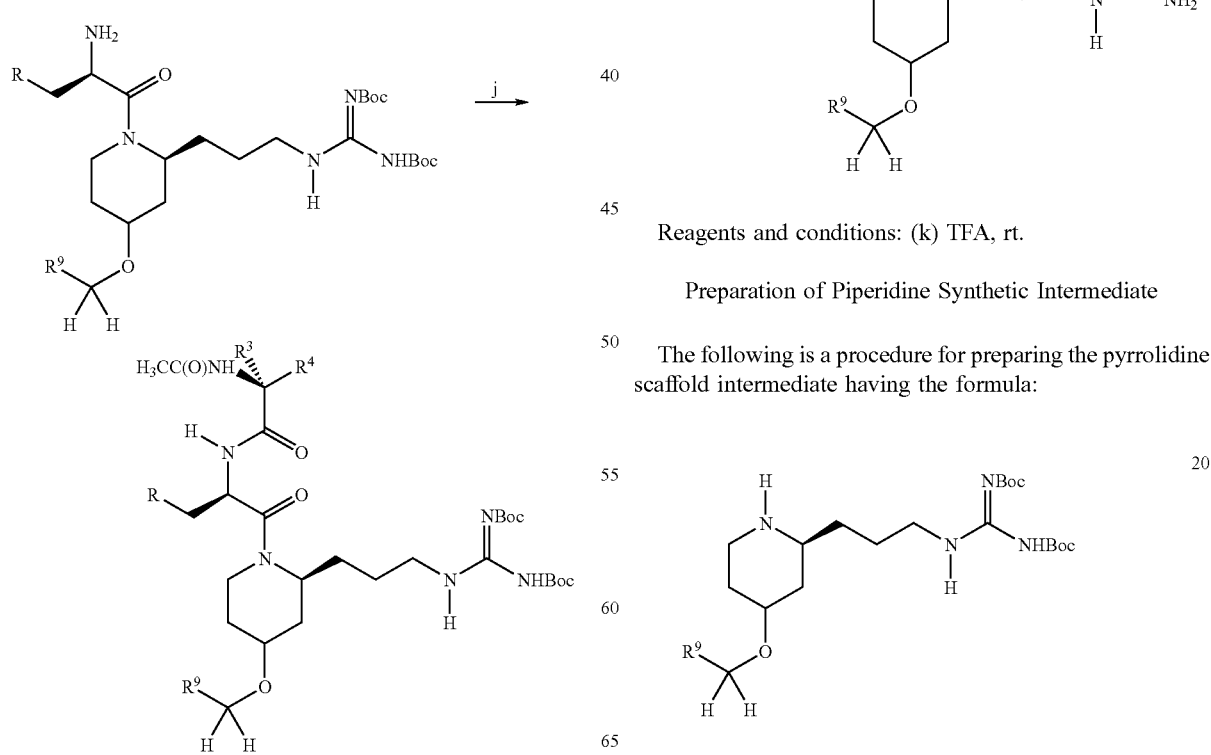

Reagents and conditions: (k) TFA, rt.

Preparation of Piperidine Synthetic Intermediate

The following is a procedure for preparing the pyrrolidine scaffold intermediate having the formula:

wherein for this example $R^9$ is a 2-naphthyl moiety.

N,N'-Di-tert-butoxycarbonyl-N"-[3-S-[4-R-(naphthalene-2-ylmethoxy)piperidin-2-yl]propyl}guanidine (20)

Preparation of N-Cbz-6-allyl-2,3-dihydro-1H-pyridin-4-one (14): To a solution of 4-methoxypyridine (50 mL, 0.492 mol) in toluene (1 L) is added benzyl chloroformate (70.3 mL, 0.492 mol) at 0° C. The resulting mixture is stirred at 0° C. for 30 minutes then cooled to −75° C. and allyl magnesium chloride (295.5 mL, 0.591 mol) is added. The solution is held at −75° C. for 4 hours and allowed to warm to 0° C. at which point a solution of 20% HCl is added to quench the reaction. The organic layer is isolated and purified over silica gel to yield the desired product.

Preparation of N-Cbz-2-S-allylpiperidin-4-one (15): To a solution of N-Cbz-6-allyl-2,3-dihydro-1H-pyridin-4-one, 14, (34.2 g, 0.126 mole) in HOAc (238 mL) at room temperature, is added zinc dust. The solution is refluxed for 30 minutes, cooled to room temperature, and the solids are removed by filtration through Celite. The product is isolated by work-up for neutral product.

Preparation of N-Cbz-2-S-allyl-4-R-hydroxypiperidine (16): To a solution of N-Cbz-2-S-allylpiperidin-4-one, 15, (34.2 g, 0.125 mol) in THF (700 mL) at 10° C. is added K-selectride (135 mL, 0.150 mol). After 5 minutes the reaction is quenched with water (60 mL). Work-up for neutral product yields the desired material which is purified over silica gel.

Preparation of N-Cbz-2-S-allyl-4-R-(naphthalene-2-ylmethoxy)piperidine (17): To a solution of N-Cbz-2-S-allyl-4-R-hydroxypiperidine, 16, (22.11 g, 0.08 mol) in DMF (300 mL) at 0° C. is added 60% NaH (4.2 g, 0.103 mol). After stirring 30 minutes, 2-(bromomethyl)naphthalene (21.3 g, 0.096 mol) is added and the reaction is stirred 24 hours at room temperature after which the reaction is cooled to 0° C. and quenched by the addition of water. Work up for neutral followed by purification over silica gel yields the desired product.

Preparation of N-Cbz-2-S-(3-hydroxy)propyl-4-R-(naphthalene-2-ylmethoxy)piperidine (18): To a solution of N-Cbz-2-S-allyl-4-R-(naphthalen-2-ylmethoxy)piperidine, 17, (1.59 g, 3.83 mmol) in THF (39 mL) at 0° C. is added borane/THF (4.2 mL, 4.221 mmol) and the reaction is allowed to warm to room temperature over 30 minutes. The reaction is quenched with water then 3M NaOH (2.4 mL), and 30% hydrogen peroxide (2.4 mL). Work up for neutral followed by purification over silica gel yields the desired product.

Preparation of N,N'-Di-tert-butoxycarbonyl-N"-[3-S-[4-R-(naphthalen-2-ylmethoxy)-N-Cbz-piperidin-2-yl]propyl}guanidine (19): To a solution of N-Boc-2-S-(3-hydroxy)propyl-4-R-(naphthalene-2-ylmethoxy)-piperidine (4.96 g, 11.89 mmol), triphenylphosphine (3.74 g, 14.26 mmol), and 1,3-bis(tert-butoxycarbonyl)guanidine (3.7 g, 14.27 mmol) in THF is added diisopropyl azodicarboxylate (2.81 mL, 14.27 mmol) at a temperature of less than 3° C. The solution is allowed to warm to room temperature, quenched by the addition of water, worked up for neutral product then purified over silica gel to yield the desired product.

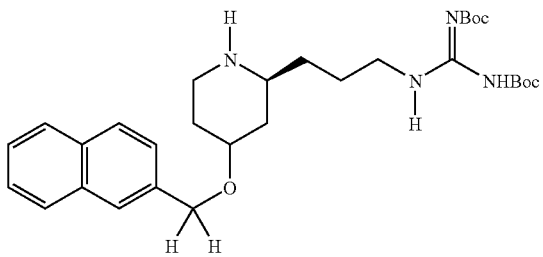

Preparation of N,N'-Di-tert-butoxycarbonyl-N"-[3-S-[4-R-(naphthalene-2-ylmethoxy)piperidin-2-yl]propyl}guanidine (20): A suspension of N,N'-Di-tert-butoxycarbonyl-N"-[3-S-[4-R-(naphthalene-2-yl-methoxy)-N-Cbz-piperidin-2-yl]propyl}guanidine, 19, (9.05 g, 13.43 mmol), pyridine (1.06 gm,13.42 mmol) and 10% Pd/C (4.5 g) in methanol (120 mL) is hydrogenated at room temperature. The solids are removed by filtration and the resulting residue after concentration is purified over silica gel to yield the desired product.

The piperidine synthetic intermediate having the formula:

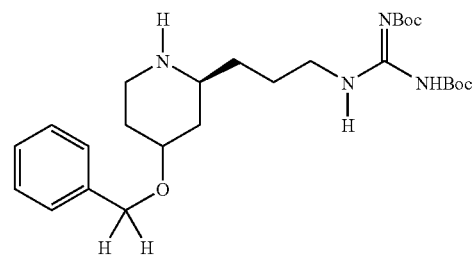

can be prepared by substituting benzyl bromide for 2-(bromomethyl)naphthylene under the conditions described herein above for the preparation of compound 17.

EXAMPLE 3

2-Acetylamino-N-{1-(4-fluorobenzyl)-2-[2-(3-guanidinopropyl)-4-(naphthalene-2-ylmethoxy)piperidin-1-yl]-2-oxo-ethyl}-3-(4-hydroxyphenyl)propionamide (24)

Preparation of [2-[2-[3-(N',N"-di-tert-butoxycarbonylguanidino)propyl]-4-naphthylen-2-ylmethoxy)piperidin-1-yl]-1-(4-fluorobenzyl)-2-oxo-ethyl]carbamic acid 9H-fluoren-9-ylmethyl ester (21): To a solution of N,N'-di-tert-butoxycarbonyl-N"-[3-S-[4-R-(naphthalene-2-yl-methoxy)piperidin-2-yl]propyl}guanidine, 20, (0.41 g, 0.759 mmol), N-Fmoc-(4-fluoro)phenylalanine (0.339 g, 0.836 mmol), and diisopropylethylamine (0.529 mL, 3.036 mmol) in dichloromethane is added PyBroP (0.707 g, 1.517 mmol) at −20° C. The solution is held at −20° C. for 24 hours after which the solvent is removed in vacuo and the resulting residue purified over silica gel to yield the desired product.

Preparation of N,N'-di-tert-butoxycarbonyl-N"-{3-[1-[2-amino-3-(4-fluorophenyl)propionyl]-4-(naphthylen-2-yl-methoxy)piperidin-2-yl]propyl}guanidine (22): A solution of [2-[2-[3-(N',N"-di-tert-butoxycarbonylguanidino)propyl]-4-naphthylen-2-ylmethoxy)piperidin-1-yl]-1-(4-fluorobenzyl)-2-oxo-ethyl]carbamic acid 9H-fluoren-9-yl-methyl ester, 21, (0.122 g, 0.132 mmol) and piperidine (0.25 mL) in dichloromethane is stirred at room temperature for 30 minutes. Concentration in vacuo affords the crude product which is purified over silica gel.

Preparation of 2-acetylamino-N-[2-[2-[3-N',N"-di-tert-butoxycarbonylguanidino)propyl]-4-(naphthylen-2-yl-methoxy)-piperidin-1-yl]-1-(4-fluorobenzyl)-2-oxoethyl]-3-(4-hydroxyphenyl)propionamide (23): To a solution of N,N'-di-tert-butoxycarbonyl-N"-{3-[1-[2-amino-3-(4-fluorophenyl)propionyl]-4-(naphthylen-2-ylmethoxy)piperidin-2-yl]propyl}-guanidine, 22, (77 mg, 0.109 mmol), N-acetyl tyrosine (29.3 mg, 0.131 mmol) and 1-hydroxybenzotriazole (31 mg, 0.162 mmol) in DMF (2 mL) at 0° C. is added 1-(3-dimethylaminopropyl)-3-ethylcarbodiimide hydrochloride. The solution is stirred at 0° C. for 2 hours then partitioned between ether and aqueous bicarbonate, the organic phase is dried, concentrated in vacuo and purified over silica gel to yield the desired product.

Preparation of 2-Acetylamino-[1-(4-fluorobenzyl-2-[2-[3-guanidino)propyl]-4-(naphthylene-2-ylmethoxy)-piperidin-1-yl]-2-oxoethyl]}-3-(4-hydroxyphenyl)propionamide (24): To a solution of 2-acetylamino-N-[2-[2-[3-N',N"-di-tert-butoxycarbonylguanidino)propyl]-4-(naphthylen-2-yl-methoxy)-piperidin-1-yl]-1-(4-fluorobenzyl)-2-oxoethyl]-3-(4-hydroxyphenyl)propionamide, 23, (55 mg, 0.06 mmole) in dichloromethane (2 mL) is added trifluoroacetic acid (0.3 mL) and the solution is allowed to stir at room temperature for 7 hours. Concentration and purification over silica gel affords the desired product, Analog 107, from Table II.

Another category of receptor ligand analogs according to the present invention relates to conformationally restricted rings comprising the 5-ketopiperazine scaffold having the formula:

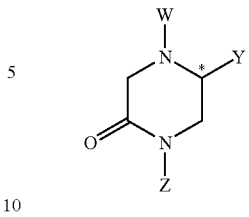

wherein the carbon indicated with an asterisk can have any configuration. Table III relates to non-limiting examples of analogs comprising a first aspect of this category, said analogs having the formula:

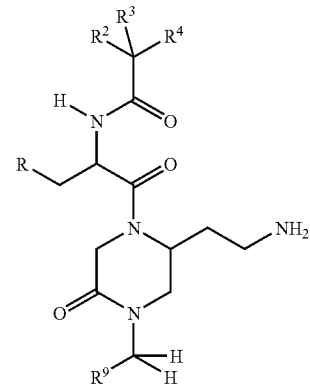

wherein R, $R^2$, $R^3$, $R^4$, and $R^9$ are defined in Table III.

TABLE III

| No. | R | $R^2$ | $R_3$ | $R^4$ | $R^9$ |
|---|---|---|---|---|---|
| 121 | phenyl | —NHCOCH$_3$ | H | benzyl | benzyl |
| 122 | 4-chlorophenyl | —NHCOCH$_3$ | H | benzyl | benzyl |
| 123 | 4-fluorophenyl | —NHCOCH$_3$ | H | benzyl | benzyl |
| 124 | 3,4-difluorophenyl | —NHCOCH$_3$ | H | benzyl | benzyl |
| 125 | phenyl | —NHCOCH$_3$ | H | 2-imidazolylmethyl | benzyl |
| 126 | 4-chlorophenyl | —NHCOCH$_3$ | H | 2-imidazolylmethyl | benzyl |
| 127 | 4-fluorophenyl | —NHCOCH$_3$ | H | 2-imidazolylmethyl | benzyl |
| 128 | 3,4-difluorophenyl | —NHCOCH$_3$ | H | 2-imidazolylmethyl | benzyl |
| 129 | phenyl | —NHCOCH$_3$ | H | 4-imidazolylmethyl | benzyl |
| 130 | 4-chlorophenyl | —NHCOCH$_3$ | H | 4-imidazolylmethyl | benzyl |
| 131 | 4-fluorophenyl | —NHCOCH$_3$ | H | 4-imidazolylmethyl | benzyl |
| 132 | 3,4-difluorophenyl | —NHCOCH$_3$ | H | 4-imidazolylmethyl | benzyl |
| 133 | phenyl | —NHCOCH$_3$ | H | 4-fluorobenzyl | benzyl |
| 134 | 4-chlorophenyl | —NHCOCH$_3$ | H | 4-fluorobenzyl | benzyl |
| 135 | 4-fluorophenyl | —NHCOCH$_3$ | H | 4-fluorobenzyl | benzyl |
| 136 | 3,4-difluorophenyl | —NHCOCH$_3$ | H | 4-fluorobenzyl | benzyl |
| 137 | phenyl | —NHCOCH$_3$ | H | 4-hydroxybenzyl | benzyl |
| 138 | 4-chlorophenyl | —NHCOCH$_3$ | H | 4-hydroxybenzyl | benzyl |
| 139 | 4-fluorophenyl | —NHCOCH$_3$ | H | 4-hydroxybenzyl | benzyl |
| 140 | 3,4-difluorophenyl | —NHCOCH$_3$ | H | 4-hydroxybenzyl | benzyl |
| 141 | phenyl | —NHCOCH$_3$ | H | 4-chlorobenzyl | benzyl |
| 142 | 4-chlorophenyl | —NHCOCH$_3$ | H | 4-chlorobenzyl | benzyl |
| 143 | 4-fluorophenyl | —NHCOCH$_3$ | H | 4-chlorobenzyl | benzyl |
| 144 | 3,4-difluorophenyl | —NHCOCH$_3$ | H | 4-chlorobenzyl | benzyl |
| 145 | phenyl | —NHCOCH$_3$ | H | 4-acetoxybenzyl | benzyl |
| 146 | 4-chlorophenyl | —NHCOCH$_3$ | H | 4-acetoxybenzyl | benzyl |
| 147 | 4-fluorophenyl | —NHCOCH$_3$ | H | 4-acetoxybenzyl | benzyl |
| 148 | 3,4-difluorophenyl | —NHCOCH$_3$ | H | 4-acetoxybenzyl | benzyl |
| 149 | phenyl | —NHCOCH$_3$ | H | benzyl | 2-naphthylmethyl |
| 150 | 4-chlorophenyl | —NHCOCH$_3$ | H | benzyl | 2-naphthylmethyl |
| 151 | 4-fluorophenyl | —NHCOCH$_3$ | H | benzyl | 2-naphthylmethyl |
| 152 | 3,4-difluorophenyl | —NHCOCH$_3$ | H | benzyl | 2-naphthylmethyl |
| 153 | phenyl | —NHCOCH$_3$ | H | 2-imidazolylmethyl | 2-naphthylmethyl |

TABLE III-continued

| No. | R | R² | R₃ | R⁴ | R⁹ |
|---|---|---|---|---|---|
| 154 | 4-chlorophenyl | —NHCOCH₃ | H | 2-imidazolylmethyl | 2-naphthylmethyl |
| 155 | 4-fluorophenyl | —NHCOCH₃ | H | 2-imidazolylmethyl | 2-naphthylmethyl |
| 156 | 3,4-difluorophenyl | —NHCOCH₃ | H | 2-imidazolylmethyl | 2-naphthylmethyl |
| 157 | phenyl | —NHCOCH₃ | H | 4-imidazolylmethyl | 2-naphthylmethyl |
| 158 | 4-chlorophenyl | —NHCOCH₃ | H | 4-imidazolylmethyl | 2-naphthylmethyl |
| 159 | 4-fluorophenyl | —NHCOCH₃ | H | 4-imidazolylmethyl | 2-naphthylmethyl |
| 160 | 3,4-difluorophenyl | —NHCOCH₃ | H | 4-imidazolylmethyl | 2-naphthylmethyl |
| 161 | phenyl | —NHCOCH₃ | H | 4-fluorobenzyl | 2-naphthylmethyl |
| 162 | 4-chlorophenyl | —NHCOCH₃ | H | 4-fluorobenzyl | 2-naphthylmethyl |
| 163 | 4-fluorophenyl | —NHCOCH₃ | H | 4-fluorobenzyl | 2-naphthylmethyl |
| 164 | 3,4-difluorophenyl | —NHCOCH₃ | H | 4-fluorobenzyl | 2-naphthylmethyl |
| 165 | phenyl | —NHCOCH₃ | H | 4-hydroxybenzyl | 2-naphthylmethyl |
| 166 | 4-chlorophenyl | —NHCOCH₃ | H | 4-hydroxybenzyl | 2-naphthylmethyl |
| 167 | 4-fluorophenyl | —NHCOCH₃ | H | 4-hydroxybenzyl | 2-naphthylmethyl |
| 168 | 3,4-difluorophenyl | —NHCOCH₃ | H | 4-hydroxybenzyl | 2-naphthylmethyl |
| 169 | phenyl | —NHCOCH₃ | H | 4-chlorobenzyl | 2-naphthylmethyl |
| 170 | 4-chlorophenyl | —NHCOCH₃ | H | 4-chlorobenzyl | 2-naphthylmethyl |
| 171 | 4-fluorophenyl | —NHCOCH₃ | H | 4-chlorobenzyl | 2-naphthylmethyl |
| 172 | 3,4-difluorophenyl | —NHCOCH₃ | H | 4-chlorobenzyl | 2-naphthylmethyl |
| 173 | phenyl | —NHCOCH₃ | H | 4-acetoxybenzyl | 2-naphthylmethyl |
| 174 | 4-chlorophenyl | —NHCOCH₃ | H | 4-acetoxybenzyl | 2-naphthylmethyl |
| 175 | 4-fluorophenyl | —NHCOCH₃ | H | 4-acetoxybenzyl | 2-naphthylmethyl |
| 176 | 3,4-difluorophenyl | —NHCOCH₃ | H | 4-acetoxybenzyl | 2-naphthylmethyl |
| 177 | phenyl | H | H | benzyl | 2-naphthylmethyl |
| 178 | 4-chlorophenyl | H | H | benzyl | 2-naphthylmethyl |
| 179 | 4-fluorophenyl | H | H | benzyl | 2-naphthylmethyl |
| 180 | 3,4-difluorophenyl | H | H | benzyl | 2-naphthylmethyl |

The following is an outline of a synthetic pathway for preparing analogs 121–180, however, other embodiments of the 5-ketopiperazine scaffold can be prepared using modifications to this general scheme.

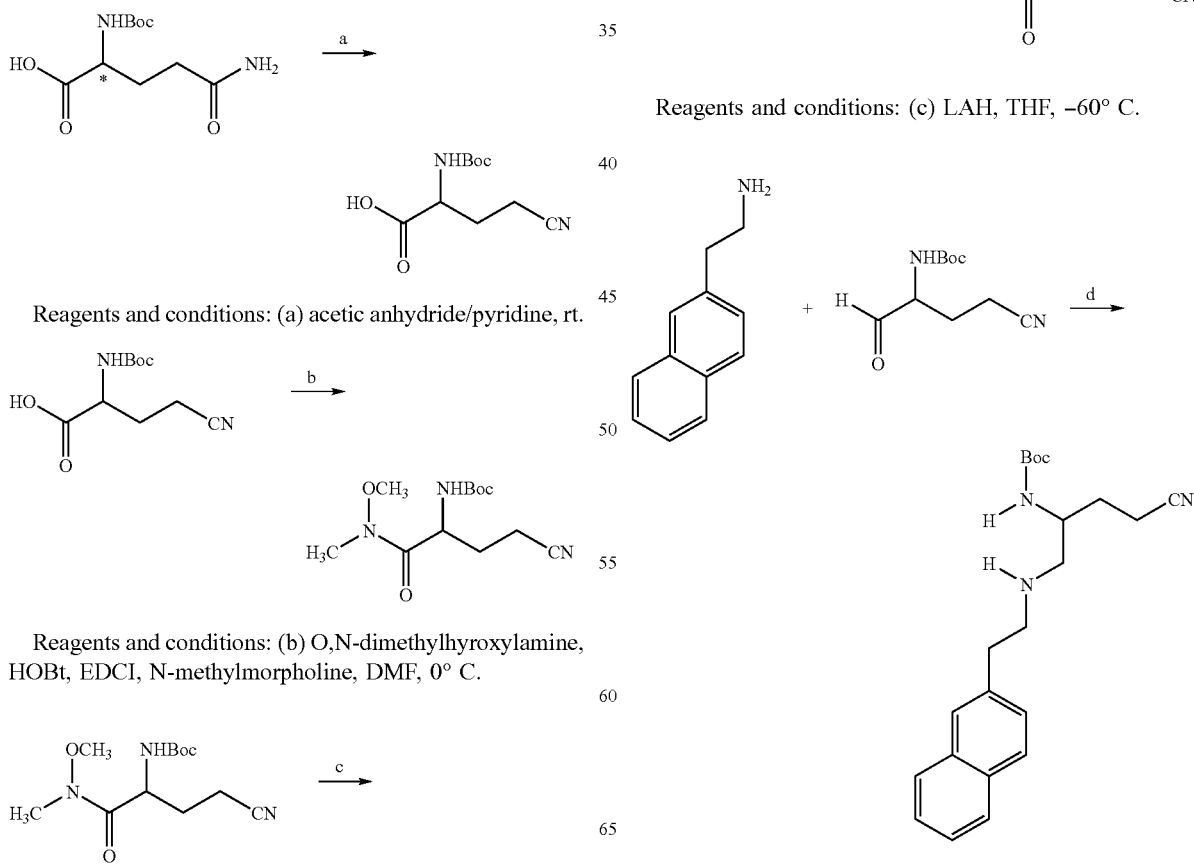

Reagents and conditions: (a) acetic anhydride/pyridine, rt.

Reagents and conditions: (b) O,N-dimethylhyroxylamine, HOBt, EDCI, N-methylmorpholine, DMF, 0° C.

Reagents and conditions: (c) LAH, THF, −60° C.

61
Reagents and conditions: (d) NaBH(OAc)₃, DMF, 0° C. to rt.
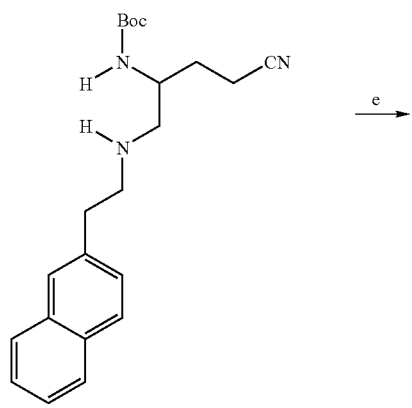
Reagents and conditions: (e) ClCH₂COCl, Et₃N, CH₂Cl₂, 0° C. to rt.
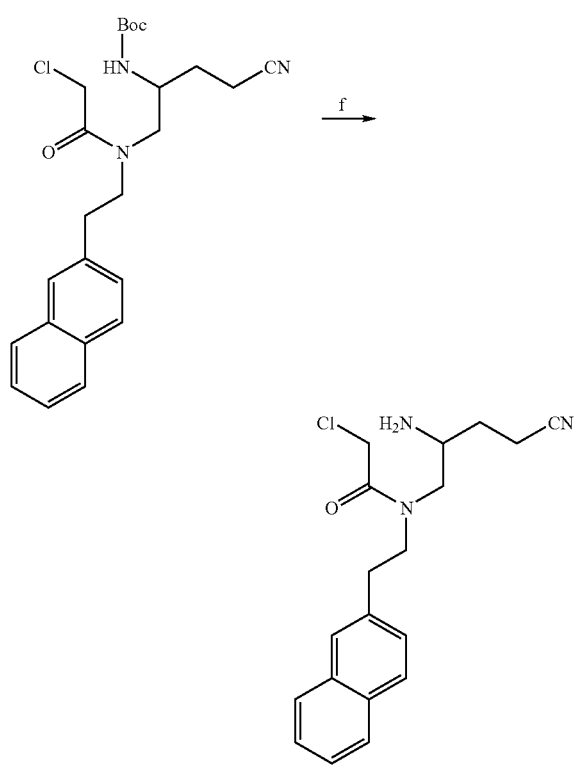
62
Reagents and conditions: (f) TFA/CH₂Cl₂, rt.
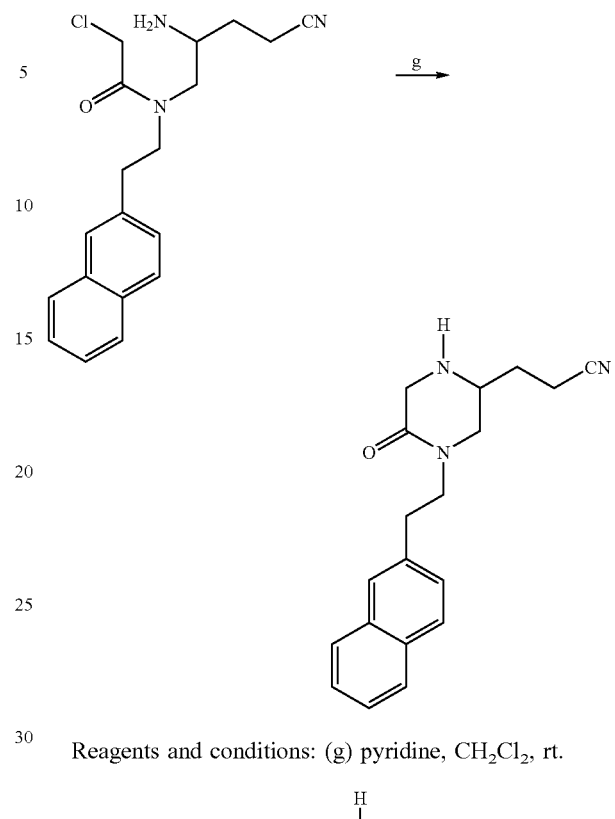
Reagents and conditions: (g) pyridine, CH₂Cl₂, rt.
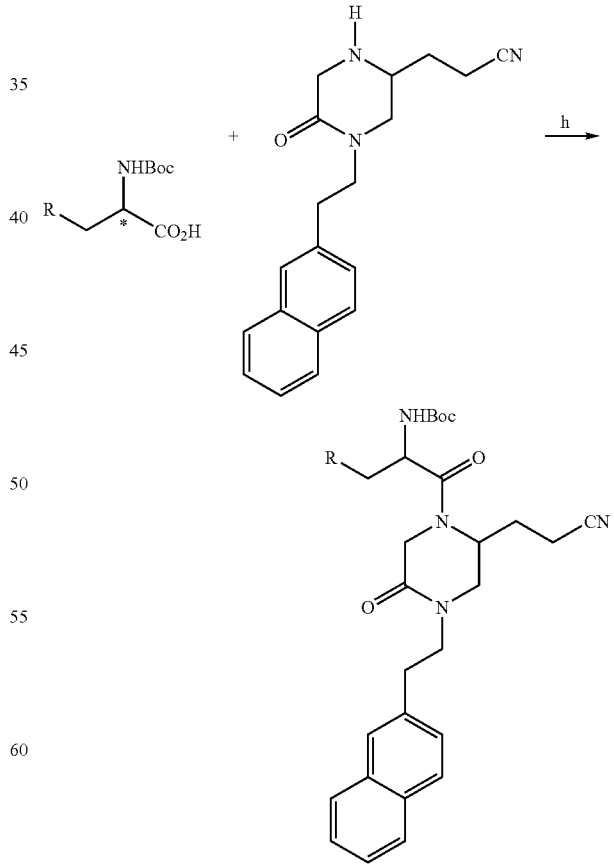
Reagents and conditions: (h) N-Boc-amino acid, EDCI, HOBt, DMF.

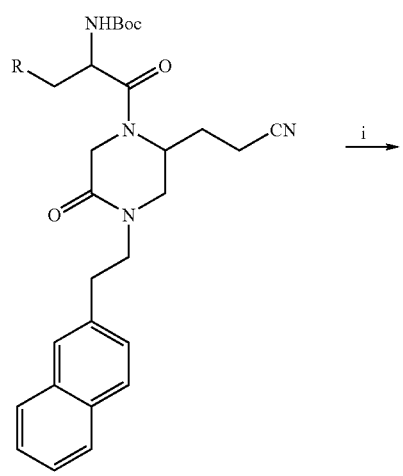
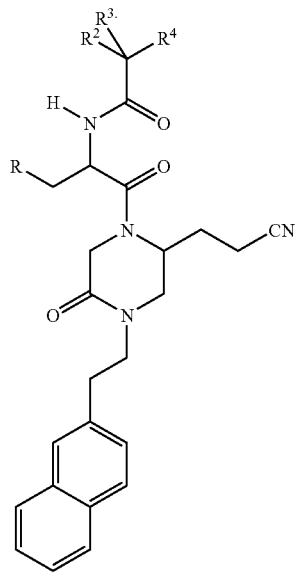
-continued
Reagents and conditions: (j) N-acetyl-amino acid, EDCI, HOBt, DMF.
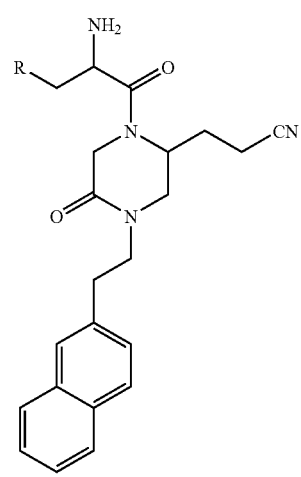
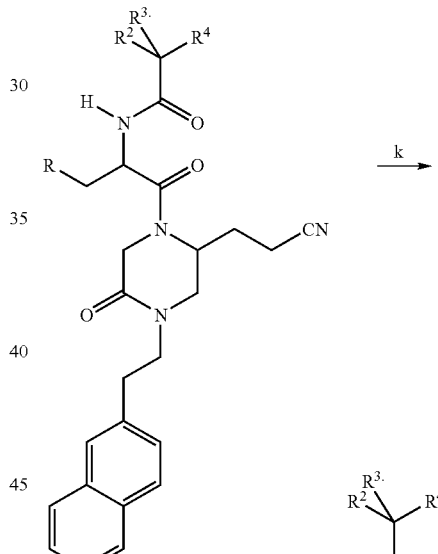
Reagents and conditions: (i) TFA/CH$_2$Cl$_2$, rt.
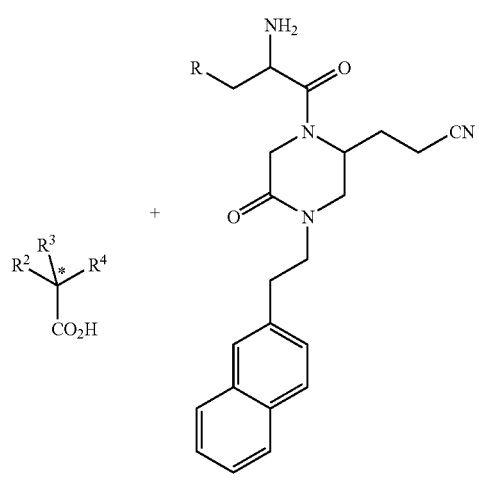
Reagents and conditions: (k) H2, PtO$_2$, MeOH.

Preparation of 5-Ketopiperazine Intermediate

The following is a procedure for preparing the 5-ketopiperazine intermediate having the formula:

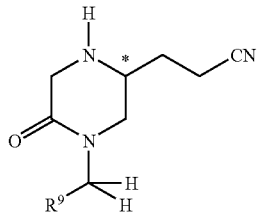

wherein for this example R⁹ is a 2-naphthylmethyl moiety.

3-S-[4-(2-Naphthalen-2-ylethyl)-5-oxo-piperazin-2-yl]propionitrile (31)

Preparation of 2-N-(tert-butoxycarbonyl)amino-4-cyanobutanoic acid (25): A flask is charged with N-tert-butoxycarbonyl glutamine (24.6 g, 100 mmol), acetic anhydride (112 g, 110 mmol) and pyridine (180 mL). The mixture is stirred for 18 hours then concentrated in vacuo. The residue is partition between EtOAc and water and the organic layer is washed several times with a citric acid solution, then with sat. NaCl. The organic phase is dried and concentrated in vacuo to afford the desired product which is used without further purification.

Preparation of 3-cyano-1-(methoxymethylcarbamoyl) propyl] carbamic acid tert-butyl ester (26): A solution of 2-N-(tert-butoxycarbonyl)amino-4-cyanobutanoic acid, 25, (22.8 g, 100 mmol), O,N-dimethoxy-hydroxylamine hydrochloride (10.6 g, 110 mmol), hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which is triturated with diethyl ether/hexane to afford a white solid which is collected by filtration. The product is sufficiently pure for use without further purification.

Preparation of 2-S-N-Boc-amino-4-cyanobutyraldehyde (27): To a solution of 3-cyano-1-(methoxymethylcarbamoyl)propyl]carbamic acid tert-butyl ester, 26, (27.1 g, 100 mmol) in 500 mL of THF at −30° C. to −25° C. is added LAH (100 mL of a 1M solution in THF) over about 10 minutes and the reaction is then cooled to −55° C. and the stirring is continued for 3 hours. After cooling to −60° C., the reaction is quenched by the addition of citric acid in methanol (1:1 by weight). During quenching the temperature is maintained at about −45° C. The mixture is then allowed to warm to room temperature and partitioned between EtOAc and water and the water phase extracted again with EtOAc. The organic phases are combined and washed with sat NaCl, dried and concentrated in vacuo to afford the crude aldehyde which is used without further purification.

Preparation of 3-S-N-Boc-amino-4-(2-naphthalen-2-ylethylamino)butylnitrile (28): The crude aldehyde 2-S-N-Boc-amino-4-cyanobutyraldehyde, 27, is dissolved in DMF (200 mL) and a solution of 2-naphthylethyl amine (17.1 g, 100 mmol) in 125 mL of DMF is added. The solution is cooled to 0° C. and sodium triacetoxyborohydride (42.4 g, 200 mmol) is added. The suspension as stirred at 0° C. and allowed to warm over 2 hours to room temperature. A saturated aqueous solution of sodium bicarbonate is added until the evolution of gas stops. The solution is extracted with diethyl ether, dried and concentrated to afford the crude product which is purified over silica gel.

Preparation of 3-S-N-Boc-amino-4-[(2-chloroacetyl-2-naphthalen-2-ylethyl)amino]-butylnitrile (29): To a solution of 3-S-N-Boc-amino-4-(2-naphthalen-2-ylethylamino)-butylnitrile, 28, (36.8 g, 100 mmol) and triethylamine (27.8 mL, 200 mmole) in dichloromethane (500 mL) held at 0° C. is added dropwise chloroacetyl chloride (14.7 g, 130 mmole). The resulting solution is held in an ice bath for an additional hour, the solution concentrated in vacuo and the crude material is purified over silica gel.

Preparation of 3-S-amino-4-[(2-chloroacetyl-2-naphthalen-2-ylethyl)amino]-butylnitrile (30): A solution of 3-S-N-Boc-amino-4-[(2-chloroacetyl-2-naphthalen-2-ylethyl) amino]butylnitrile, 29, (44.4 g, 100 mmol), trifluoroacetic acid (50 mL), and dichloromethane (500 mL) is stirred at room temperature for 30 minutes and then concentrated in vacuo. The crude product can be used without further purification.

Preparation of 3-S-[4-(2-naphthalen-2-ylethyl)-5-oxo-piperazin-2-yl]propionitrile (31): 3-S-amino-4-[(2-chloroacetyl-2-naphthalen-2-ylethyl)amino]-butylnitrile trifluoroacetic acid salt, 30, (45.8 g, 100 mmol) is taken up in dichloromethane 1000 mL and pyridine (50 mL) is added. The solution is stirred at room temperature for 24 hours and is then concentrated in vacuo. The resulting crude product is purified over silica gel to afford the desired product as the trifluoroacetate salt.

EXAMPLE 4

2-Acetylamino-N-{2-[2-(3-aminopropyl)-4-(2-napthalen-2-ylethyl)-5-oxo-piperazin-1-yl]-1-benzyl-2-oxo-ethyl}-3-(4-hydroxyphenyl) propionamide (34)

Preparation of [2-[2-2-cyanoethyl)-4-(2-naphthalen-2-ylethyl)-5-oxo-piperazin-1-yl]-1-(4-fluorobenzyl)-2-oxo-ethyl]carbamic acid tert-butyl ester (32): To a solution of 3-S-[4-(2-naphthalen-2-ylethyl)-5-oxo-piperazin-2-yl]propionitrile trifluoroacetic acid salt, 31, (42.1 g, 100 mmol), (R)-2-N-(tert-butoxycarbonyl)amino-3-(4-fluorophenyl) propanoic acid (34.0 g, 120 mmol), 1-hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a white foaming residue.

Preparation of 3-[1-[2-amino-3-(4-fluorophenyl)propionyl]-4-(2-naphthalen-2-ylethyl)-5-oxo-piperazin-2-yl]-propionitrile (33): A solution of [2-[2-2-cyanoethyl)-4-(2-naphthalen-2-ylethyl)-5-oxo-piperazin-1-yl]-1-(4-fluorobenzyl)-2-oxo-ethyl]carbamic acid tert-butyl ester, 32, (57.2 g, 100 mmol), trifluoroacetic acid (50 mL), and dichloromethane (500 mL) is stirred at room temperature for 2 hours and then concentrated in vacuo. The crude product is dissolved in dichloromethane and the organic layer washed with saturated sodium bicarbonate, dried, and concentrated in vacuo. The desired product is obtained in 94% yield.

Preparation of 2-acetylamino-N-[2-[2-(2-cyanoethyl)-4-(2-naphthalen-2-ylethyl)-5-oxo-piperazin-1-yl]-1-(4-fluorobenzyl)-2-oxo-ethyl]-3-(4-hydroxyphenyl)-propionamide (34): To a solution of 3-[1-[2-amino-3-(4-fluorophenyl)propionyl]-4-(2-naphthalen-2-ylethyl)-5-oxo-piperazin-2-yl]propionitrile, 33, (47.2 g, 100 mmol), N-acetyl-L-tyrosine (22.3 g, 120 mmol), 1-hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford the crude product which is purified over silica gel.

Preparation of 2-acetylamino-N-[2-[2-(3-aminoethyl)-4-(2-naphthalen-2-ylethyl)-5-oxo-piperazin-1-yl]-1-(4-fluorobenzyl)-2-oxo-ethyl]-3-(4-hydroxyphenyl)-propionamide (35): To a suspension of 2-acetylamino-N-[2-[2-(2-cyanoethyl)-4-(2-naphthalen-2-ylethyl)-5-oxo-piperazin-1-yl]-1-(4-fluorobenzyl)-2-oxo-ethyl]-3-(4-hydroxyphenyl)-propionamide, 34, (57 mg) and $PtO_2$ (11 mg of 20% by weight) in methanol (3 mL) is added one drop of conc. HCl. The solution is hydrogenated at 45 psi for 1.5 hours. The catalyst is removed by filtration and the filtrate is concentrated in vacuo to afford the final product which is purified by prep HPLC using acetonitrile:TFA:water to yield 26 mg. This corresponds to analog 167 from Table III.

Another aspect of this category of receptor ligand analogs relates to conformationally restricted rings comprising the 5-ketopiperazine scaffold having the formula:

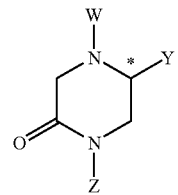

wherein the Y unit comprises a guanidino moiety. Table III relates to non-limiting examples of analogs comprising a first aspect of this category, said analogs having the formula:

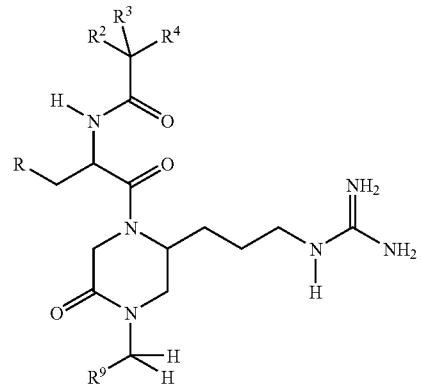

wherein R, $R^2$, $R^3$, $R^4$, and $R^9$ are defined in Table IV.

TABLE IV

| No. | R | $R^2$ | $R^3$ | $R^4$ | $R^9$ |
|---|---|---|---|---|---|
| 181 | phenyl | —NHCOCH$_3$ | H | benzyl | benzyl |
| 182 | 4-chlorophenyl | —NHCOCH$_3$ | H | benzyl | benzyl |
| 183 | 4-fluorophenyl | —NHCOCH$_3$ | H | benzyl | benzyl |
| 184 | 3,4-difluorophenyl | —NHCOCH$_3$ | H | benzyl | benzyl |
| 185 | phenyl | —NHCOCH$_3$ | H | 2-imidazolylmethyl | benzyl |
| 186 | 4-chlorophenyl | —NHCOCH$_3$ | H | 2-imidazolylmethyl | benzyl |
| 187 | 4-fluorophenyl | —NHCOCH$_3$ | H | 2-imidazolylmethyl | benzyl |
| 188 | 3,4-difluorophenyl | —NHCOCH$_3$ | H | 2-imidazolylmethyl | benzyl |
| 189 | phenyl | —NHCOCH$_3$ | H | 4-imidazolylmethyl | benzyl |
| 190 | 4-chlorophenyl | —NHCOCH$_3$ | H | 4-imidazolylmethyl | benzyl |
| 191 | 4-fluorophenyl | —NHCOCH$_3$ | H | 4-imidazolylmethyl | benzyl |
| 192 | 3,4-difluorophenyl | —NHCOCH$_3$ | H | 4-imidazolylmethyl | benzyl |
| 193 | phenyl | —NHCOCH$_3$ | H | 4-fluorobenzyl | benzyl |
| 194 | 4-chlorophenyl | —NHCOCH$_3$ | H | 4-fluorobenzyl | benzyl |
| 195 | 4-fluorophenyl | —NHCOCH$_3$ | H | 4-fluorobenzyl | benzyl |
| 196 | 3,4-difluorophenyl | —NHCOCH$_3$ | H | 4-fluorobenzyl | benzyl |
| 197 | phenyl | —NHCOCH$_3$ | H | 4-hydroxybenzyl | benzyl |
| 198 | 4-chlorophenyl | —NHCOCH$_3$ | H | 4-hydroxybenzyl | benzyl |
| 199 | 4-fluorophenyl | —NHCOCH$_3$ | H | 4-hydroxybenzyl | benzyl |
| 200 | 3,4-difluorophenyl | —NHCOCH$_3$ | H | 4-hydroxybenzyl | benzyl |
| 201 | phenyl | —NHCOCH$_3$ | H | 4-chlorobenzyl | benzyl |
| 202 | 4-chlorophenyl | —NHCOCH$_3$ | H | 4-chlorobenzyl | benzyl |
| 203 | 4-fluorophenyl | —NHCOCH$_3$ | H | 4-chlorobenzyl | benzyl |
| 204 | 3,4-difluorophenyl | —NHCOCH$_3$ | H | 4-chlorobenzyl | benzyl |
| 205 | phenyl | —NHCOCH$_3$ | H | 4-acetoxybenzyl | benzyl |

TABLE IV-continued

| No. | R | $R^2$ | $R^3$ | $R^4$ | $R^9$ |
|---|---|---|---|---|---|
| 206 | 4-chlorophenyl | —NHCOCH$_3$ | H | 4-acetoxybenzyl | benzyl |
| 207 | 4-fluorophenyl | —NHCOCH$_3$ | H | 4-acetoxybenzyl | benzyl |
| 208 | 3,4-difluorophenyl | —NHCOCH$_3$ | H | 4-acetoxybenzyl | benzyl |
| 209 | phenyl | —NHCOCH$_3$ | H | benzyl | 2-naphthylmethyl |
| 210 | 4-chlorophenyl | —NHCOCH$_3$ | H | benzyl | 2-naphthylmethyl |
| 211 | 4-fluorophenyl | —NHCOCH$_3$ | H | benzyl | 2-naphthylmethyl |
| 212 | 3,4-difluorophenyl | —NHCOCH$_3$ | H | benzyl | 2-naphthylmethyl |
| 213 | phenyl | —NHCOCH$_3$ | H | 2-imidazolylmethyl | 2-naphthylmethyl |
| 214 | 4-chlorophenyl | —NHCOCH$_3$ | H | 2-imidazolylmethyl | 2-naphthylmethyl |
| 215 | 4-fluorophenyl | —NHCOCH$_3$ | H | 2-imidazolylmethyl | 2-naphthylmethyl |
| 216 | 3,4-difluorophenyl | —NHCOCH$_3$ | H | 2-imidazolylmethyl | 2-naphthylmethyl |
| 217 | phenyl | —NHCOCH$_3$ | H | 4-imidazolylmethyl | 2-naphthylmethyl |
| 218 | 4-chlorophenyl | —NHCOCH$_3$ | H | 4-imidazolylmethyl | 2-naphthylmethyl |
| 219 | 4-fluorophenyl | —NHCOCH$_3$ | H | 4-imidazolylmethyl | 2-naphthylmethyl |
| 220 | 3,4-difluorophenyl | —NHCOCH$_3$ | H | 4-imidazolylmethyl | 2-naphthylmethyl |
| 221 | phenyl | —NHCOCH$_3$ | H | 4-fluorobenzyl | 2-naphthylmethyl |
| 222 | 4-chlorophenyl | —NHCOCH$_3$ | H | 4-fluorobenzyl | 2-naphthylmethyl |
| 223 | 4-fluorophenyl | —NHCOCH$_3$ | H | 4-fluorobenzyl | 2-naphthylmethyl |
| 224 | 3,4-difluorophenyl | —NHCOCH$_3$ | H | 4-fluorobenzyl | 2-naphthylmethyl |
| 225 | phenyl | —NHCOCH$_3$ | H | 4-hydroxybenzyl | 2-naphthylmethyl |
| 226 | 4-chlorophenyl | —NHCOCH$_3$ | H | 4-hydroxybenzyl | 2-naphthylmethyl |
| 227 | 4-fluorophenyl | —NHCOCH$_3$ | H | 4-hydroxybenzyl | 2-naphthylmethyl |
| 228 | 3,4-difluorophenyl | —NHCOCH$_3$ | H | 4-hydroxybenzyl | 2-naphthylmethyl |
| 229 | phenyl | —NHCOCH$_3$ | H | 4-chlorobenzyl | 2-naphthylmethyl |
| 230 | 4-chlorophenyl | —NHCOCH$_3$ | H | 4-chlorobenzyl | 2-naphthylmethyl |
| 231 | 4-fluorophenyl | —NHCOCH$_3$ | H | 4-chlorobenzyl | 2-naphthylmethyl |
| 232 | 3,4-difluorophenyl | —NHCOCH$_3$ | H | 4-chlorobenzyl | 2-naphthylmethyl |
| 233 | phenyl | —NHCOCH$_3$ | H | 4-acetoxybenzyl | 2-naphthylmethyl |
| 234 | 4-chlorophenyl | —NHCOCH$_3$ | H | 4-acetoxybenzyl | 2-naphthylmethyl |
| 235 | 4-fluorophenyl | —NHCOCH$_3$ | H | 4-acetoxybenzyl | 2-naphthylmethyl |
| 236 | 3,4-difluorophenyl | —NHCOCH$_3$ | H | 4-acetoxybenzyl | 2-naphthylmethyl |
| 237 | phenyl | H | H | benzyl | 2-naphthylmethyl |
| 238 | 4-chlorophenyl | H | H | benzyl | 2-naphthylmethyl |
| 239 | 4-fluorophenyl | H | H | benzyl | 2-naphthylmethyl |
| 240 | 3,4-difluorophenyl | H | H | benzyl | 2-naphthylmethyl |

The following is an outline of a synthetic pathway for preparing analogs 181–240 beginning with a synthetic intermediate which can be prepared in a manner similar to the compound described in Example 3, analog 167 above.

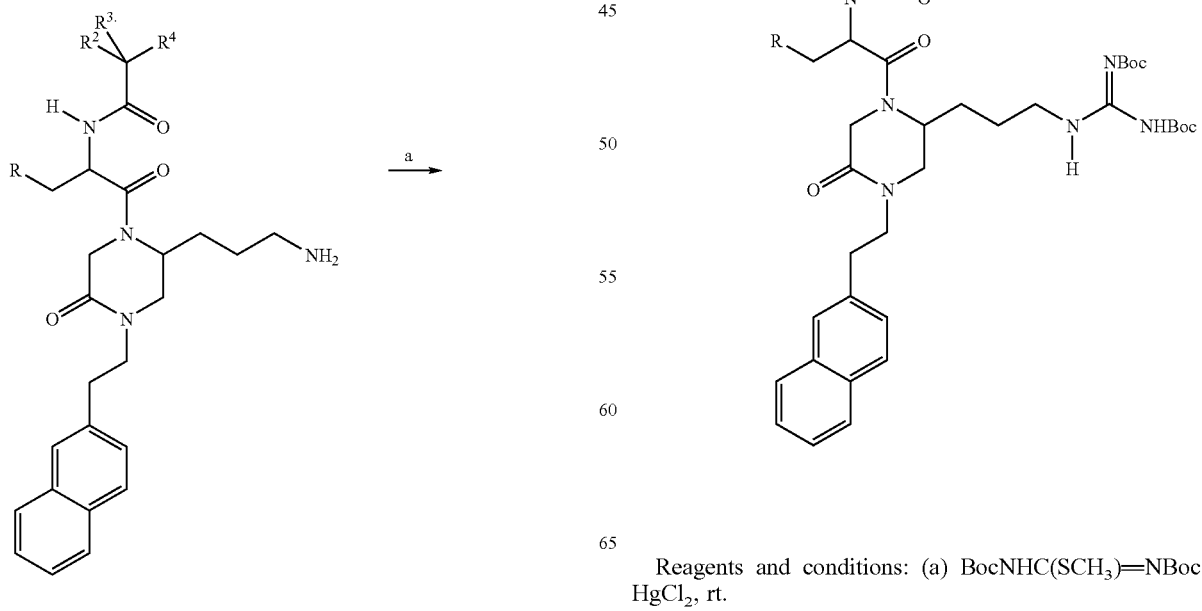

Reagents and conditions: (a) BocNHC(SCH$_3$)=NBoc, HgCl$_2$, rt.

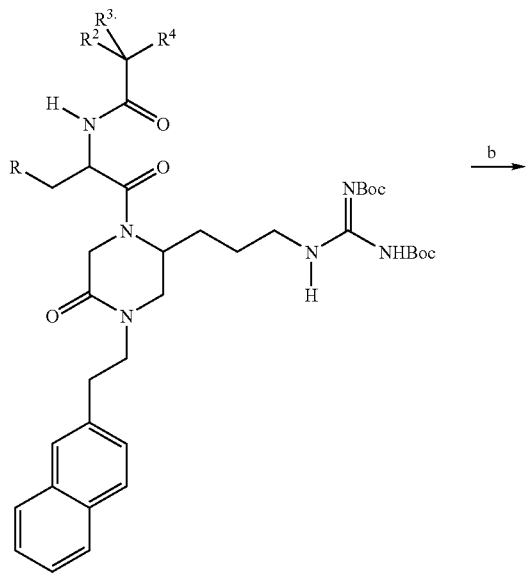

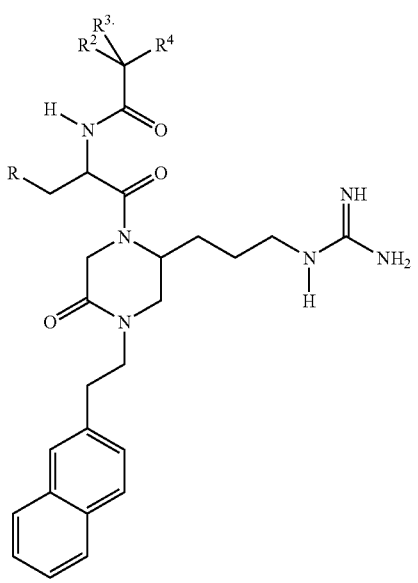

Reagents and conditions (b) TFA:CH$_2$Cl$_2$, rt.

EXAMPLE 5

2-Acetylamino-N-[2-[2-(3-guanidinopropyl)-4-(2-naphthalen-2-ylethyl)-5-oxo-piperazin-1-yl]-1-(fluorobenzyl)-2-oxo-ethyl]-3-(4-hydroxyphenyl)-propionamide (37)

Preparation of 2-acetylamino-N-[2-[2-[3-(N',N"-di-Boc-guanidino)propyl]-4-(2-naphthalen-2-ylethyl)-5-oxo-piperazin-1-yl]-1-(4-fluorobenzyl)-2-oxo-ethyl]-3-(4-hydroxyphenyl)propionamide (36): Mercury(II) chloride (10.3 mg, 0.038 mmol) is added to a solution of 2-acetylamino-N-[2-[2-(3-aminoethyl)-4-(2-naphthalen-2-ylethyl)-5-oxo-piperazin-1-yl]-1-(4-fluorobenzyl)-2-oxo-ethyl]-3-(4-hydroxyphenyl)propionamide, 35, (26 mg, 0.038 mmol), 1,3-bis(tert-butoxycarbonyl)-2-methyl-2-thiopseudo urea (11 mg, 0.038 mmol) and triethylamine (21 □L, 0.152 mmol) in dry DMF (2.0 mL) and the reaction mixture is stirred at 0° C. for 1 hour. The reaction mixture is then diluted with EtOAc, filtered through a pad of Celite, and the filtrate is concentrated in vacuo to afford the crude product as an oil. The crude isolate is purified over silica gel (CH$_2$Cl$_2$/methanol, 14:1) to afford 35 mg of the desired product as a white solid.

Preparation of 2-acetylamino-N-[2-[2-(3-guanidinopropyl)-4-(2-naphthalen-2-ylethyl)-5-oxo-piperazin-1-yl]-1-(4-fluorobenzyl)-2-oxo-ethyl]-3-(4-hydroxyphenyl)propionamide (37): A solution of 2-acetylamino-N-[2-[2-[3-(N',N"-di-Boc-guanidino)propyl]-4-(2-naphthalen-2-ylethyl)-5-oxo-piperazin-1-yl]-1-(4-fluorobenzyl)-2-oxo-ethyl]-3-(4-hydroxyphenyl)-propionamide, 36, (35 mg, 38 mmol), trifluoroacetic acid (1 mL) and dichloromethane (2 mL) is stirred at room temperature for 5 hours. The solution is concentrated in vacuo and the crude product purified over silica gel (acetonitrile:TFA:water) to afford 24 mg (86% yield) of the final product which corresponds to analog 227, Table IV.

Another category of receptor ligand analogs according to the present invention relates to conformationally restricted rings comprising the 3-keto-piperazine scaffold having the formula:

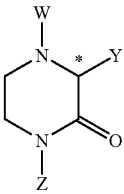

wherein the carbon indicated with an asterisk can have any configuration. Table V relates to non-limiting examples of analogs comprising a first aspect of this category, said analogs having the formula:

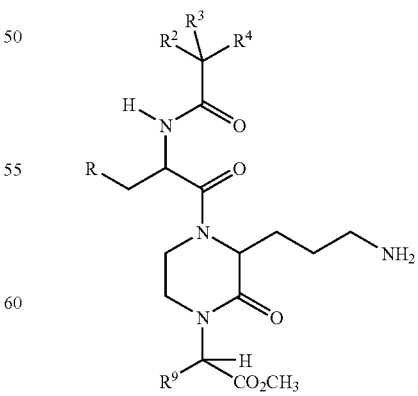

wherein R, R$^2$, R$^3$, R$^4$, and R$^9$ are defined in Table V.

TABLE V

| No. | R | $R^2$ | $R^3$ | $R^4$ | $R^9$ |
|---|---|---|---|---|---|
| 241 | phenyl | —NHCOCH$_3$ | H | benzyl | benzyl |
| 242 | 4-chlorophenyl | —NHCOCH$_3$ | H | benzyl | benzyl |
| 243 | 4-fluorophenyl | —NHCOCH$_3$ | H | benzyl | benzyl |
| 244 | 3,4-difluorophenyl | —NHCOCH$_3$ | H | benzyl | benzyl |
| 245 | phenyl | —NHCOCH$_3$ | H | 2-imidazolylmethyl | benzyl |
| 246 | 4-chlorophenyl | —NHCOCH$_3$ | H | 2-imidazolylmethyl | benzyl |
| 247 | 4-fluorophenyl | —NHCOCH$_3$ | H | 2-imidazolylmethyl | benzyl |
| 248 | 3,4-difluorophenyl | —NHCOCH$_3$ | H | 2-imidazolylmethyl | benzyl |
| 249 | phenyl | —NHCOCH$_3$ | H | 4-imidazolylmethyl | benzyl |
| 250 | 4-chlorophenyl | —NHCOCH$_3$ | H | 4-imidazolylmethyl | benzyl |
| 251 | 4-fluorophenyl | —NHCOCH$_3$ | H | 4-imidazolylmethyl | benzyl |
| 252 | 3,4-difluorophenyl | —NHCOCH$_3$ | H | 4-imidazolylmethyl | benzyl |
| 253 | phenyl | —NHCOCH$_3$ | H | 4-fluorobenzyl | benzyl |
| 254 | 4-chlorophenyl | —NHCOCH$_3$ | H | 4-fluorobenzyl | benzyl |
| 255 | 4-fluorophenyl | —NHCOCH$_3$ | H | 4-fluorobenzyl | benzyl |
| 256 | 3,4-difluorophenyl | —NHCOCH$_3$ | H | 4-fluorobenzyl | benzyl |
| 257 | phenyl | —NHCOCH$_3$ | H | 4-hydroxybenzyl | benzyl |
| 258 | 4-chlorophenyl | —NHCOCH$_3$ | H | 4-hydroxybenzyl | benzyl |
| 259 | 4-fluorophenyl | —NHCOCH$_3$ | H | 4-hydroxybenzyl | benzyl |
| 260 | 3,4-difluorophenyl | —NHCOCH$_3$ | H | 4-hydroxybenzyl | benzyl |
| 261 | phenyl | —NHCOCH$_3$ | H | 4-chlorobenzyl | benzyl |
| 262 | 4-chlorophenyl | —NHCOCH$_3$ | H | 4-chlorobenzyl | benzyl |
| 263 | 4-fluorophenyl | —NHCOCH$_3$ | H | 4-chlorobenzyl | benzyl |
| 264 | 3,4-difluorophenyl | —NHCOCH$_3$ | H | 4-chlorobenzyl | benzyl |
| 265 | phenyl | —NHCOCH$_3$ | H | 4-acetoxybenzyl | benzyl |
| 266 | 4-chlorophenyl | —NHCOCH$_3$ | H | 4-acetoxybenzyl | benzyl |
| 267 | 4-fluorophenyl | —NHCOCH$_3$ | H | 4-acetoxybenzyl | benzyl |
| 268 | 3,4-difluorophenyl | —NHCOCH$_3$ | H | 4-acetoxybenzyl | benzyl |
| 269 | phenyl | —NHCOCH$_3$ | H | benzyl | 2-naphthylmethyl |
| 270 | 4-chlorophenyl | —NHCOCH$_3$ | H | benzyl | 2-naphthylmethyl |
| 271 | 4-fluorophenyl | —NHCOCH$_3$ | H | benzyl | 2-naphthylmethyl |
| 272 | 3,4-difluorophenyl | —NHCOCH$_3$ | H | benzyl | 2-naphthylmethyl |
| 273 | phenyl | —NHCOCH$_3$ | H | 2-imidazolylmethyl | 2-naphthylmethyl |
| 274 | 4-chlorophenyl | —NHCOCH$_3$ | H | 2-imidazolylmethyl | 2-naphthylmethyl |
| 275 | 4-fluorophenyl | —NHCOCH$_3$ | H | 2-imidazolylmethyl | 2-naphthylmethyl |
| 276 | 3,4-difluorophenyl | —NHCOCH$_3$ | H | 2-imidazolylmethyl | 2-naphthylmethyl |
| 277 | phenyl | —NHCOCH$_3$ | H | 4-imidazolylmethyl | 2-naphthylmethyl |
| 278 | 4-chlorophenyl | —NHCOCH$_3$ | H | 4-imidazolylmethyl | 2-naphthylmethyl |
| 279 | 4-fluorophenyl | —NHCOCH$_3$ | H | 4-imidazolylmethyl | 2-naphthylmethyl |
| 280 | 3,4-difluorophenyl | —NHCOCH$_3$ | H | 4-imidazolylmethyl | 2-naphthylmethyl |
| 281 | phenyl | —NHCOCH$_3$ | H | 4-fluorobenzyl | 2-naphthylmethyl |
| 282 | 4-chlorophenyl | —NHCOCH$_3$ | H | 4-fluorobenzyl | 2-naphthylmethyl |
| 283 | 4-fluorophenyl | —NHCOCH$_3$ | H | 4-fluorobenzyl | 2-naphthylmethyl |
| 284 | 3,4-difluorophenyl | —NHCOCH$_3$ | H | 4-fluorobenzyl | 2-naphthylmethyl |
| 285 | phenyl | —NHCOCH$_3$ | H | 4-hydroxybenzyl | 2-naphthylmethyl |
| 286 | 4-chlorophenyl | —NHCOCH$_3$ | H | 4-hydroxybenzyl | 2-naphthylmethyl |
| 287 | 4-fluorophenyl | —NHCOCH$_3$ | H | 4-hydroxybenzyl | 2-naphthylmethyl |
| 288 | 3,4-difluorophenyl | —NHCOCH$_3$ | H | 4-hydroxybenzyl | 2-naphthylmethyl |
| 289 | phenyl | —NHCOCH$_3$ | H | 4-chlorobenzyl | 2-naphthylmethyl |
| 290 | 4-chlorophenyl | —NHCOCH$_3$ | H | 4-chlorobenzyl | 2-naphthylmethyl |
| 291 | 4-fluorophenyl | —NHCOCH$_3$ | H | 4-chlorobenzyl | 2-naphthylmethyl |
| 292 | 3,4-difluorophenyl | —NHCOCH$_3$ | H | 4-chlorobenzyl | 2-naphthylmethyl |
| 293 | phenyl | —NHCOCH$_3$ | H | 4-acetoxybenzyl | 2-naphthylmethyl |
| 294 | 4-chlorophenyl | —NHCOCH$_3$ | H | 4-acetoxybenzyl | 2-naphthylmethyl |
| 295 | 4-fluorophenyl | —NHCOCH$_3$ | H | 4-acetoxybenzyl | 2-naphthylmethyl |
| 296 | 3,4-difluorophenyl | —NHCOCH$_3$ | H | 4-acetoxybenzyl | 2-naphthylmethyl |
| 297 | phenyl | H | H | benzyl | 2-naphthylmethyl |
| 298 | 4-chlorophenyl | H | H | benzyl | 2-naphthylmethyl |
| 299 | 4-fluorophenyl | H | H | benzyl | 2-naphthylmethyl |
| 300 | 3,4-difluorophenyl | H | H | benzyl | 2-naphthylmethyl |

The following is an outline of a synthetic pathway for preparing analogs 241–300, however, other embodiments of the piperazine scaffold can be prepared using modifications to this general scheme.

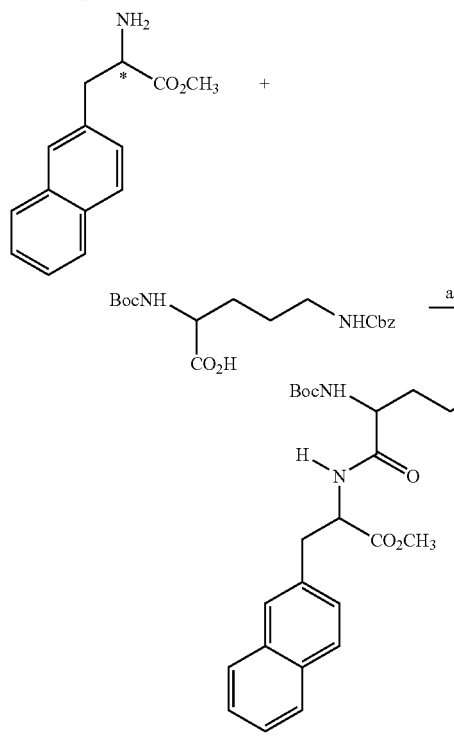

Reagents and conditions: (a) EDCI, HOBt, DMF.

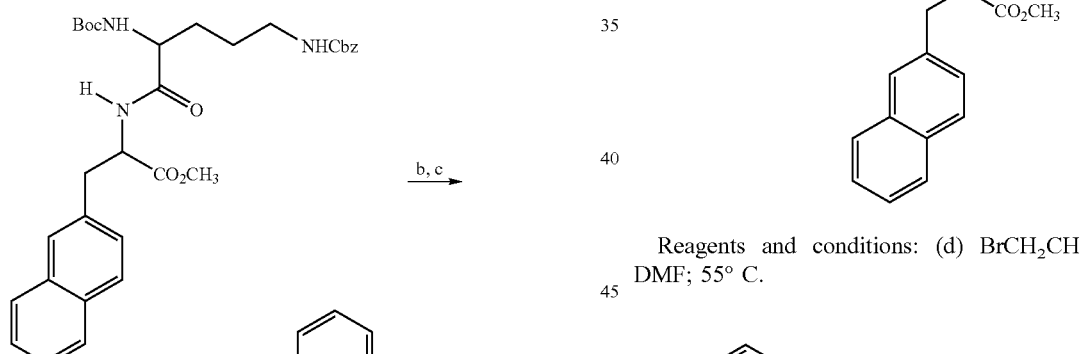

Reagents and conditions: (b) TFA:CH$_2$Cl$_2$:H$_2$O, rt; (c) 2-nitrosulfonyl chloride, TEA, CH$_2$Cl$_2$, 0° C. to rt.

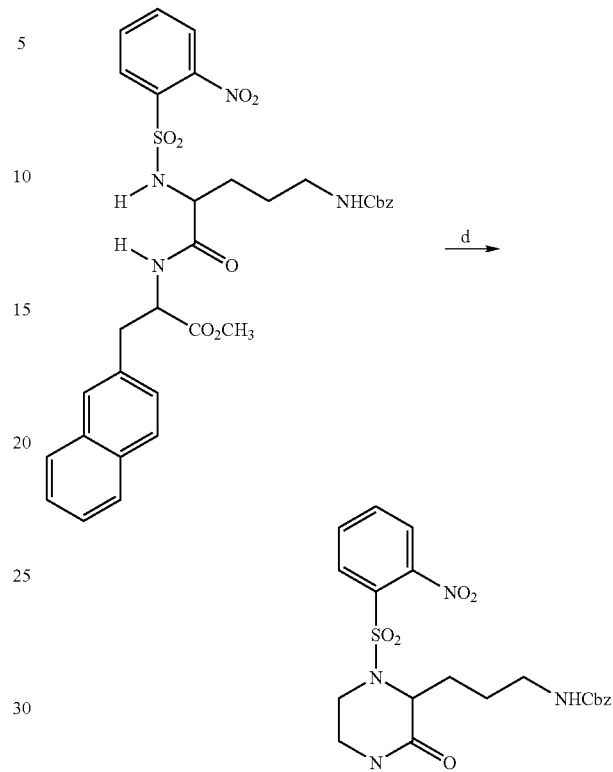

Reagents and conditions: (d) BrCH$_2$CH$_2$Br, K$_2$CO$_3$, DMF; 55° C.

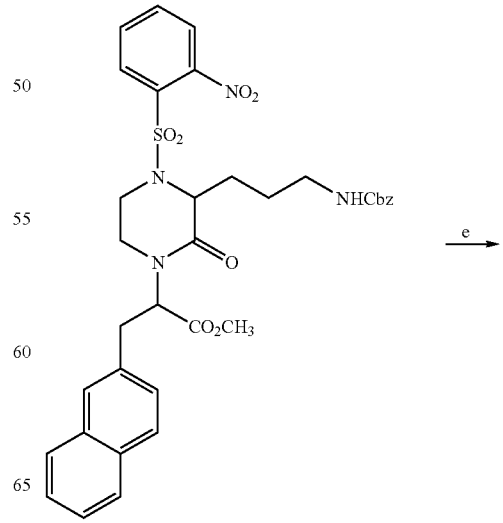

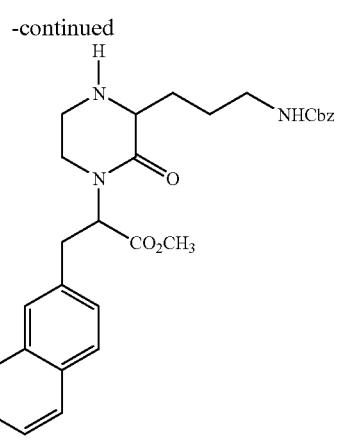
Reagents and conditions: (e) p-thiophenol, K$_2$CO$_3$, acetonitrile; rt.
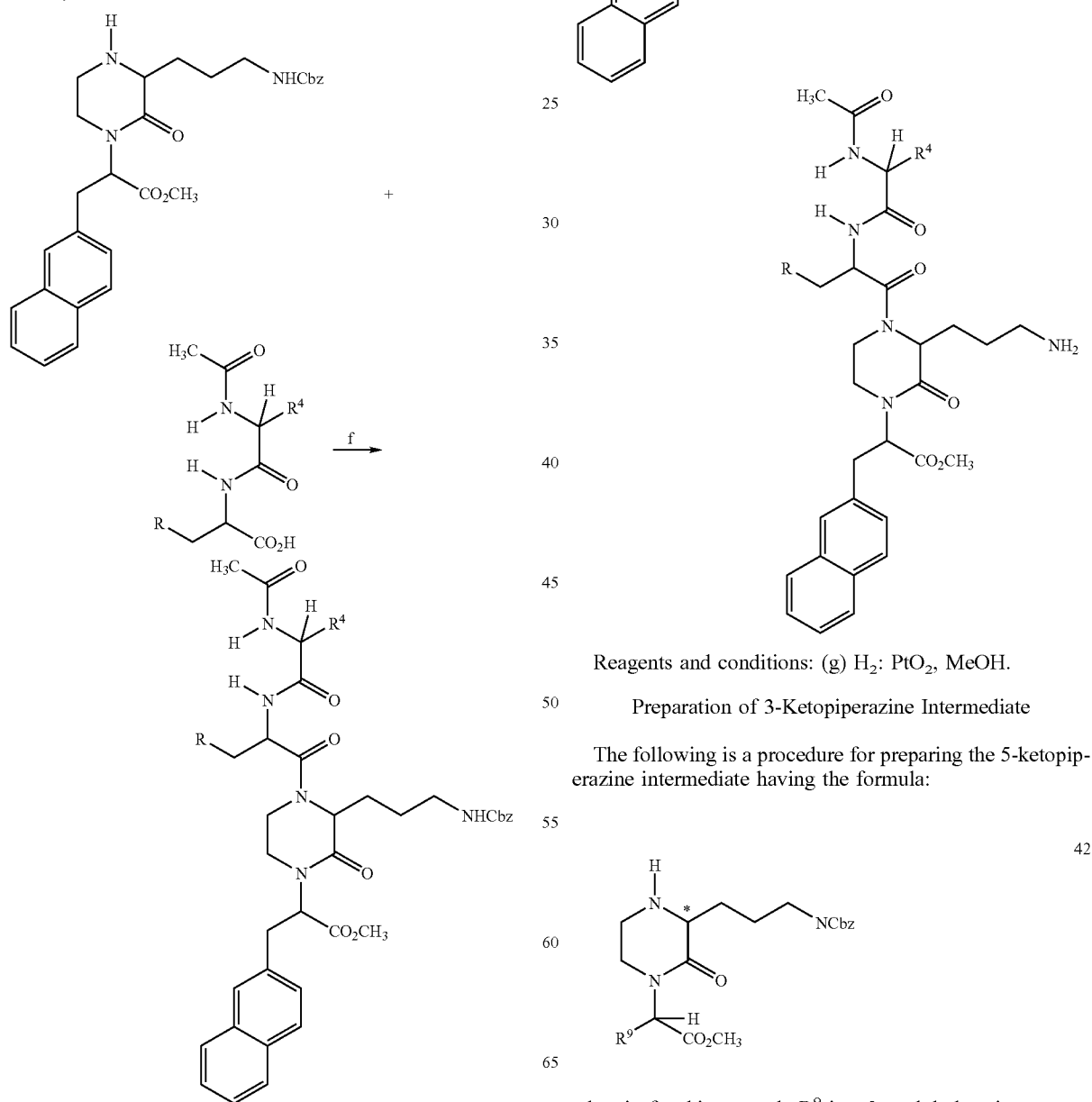
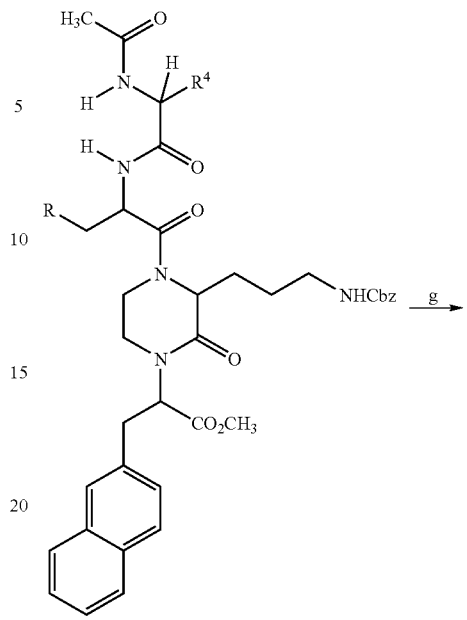
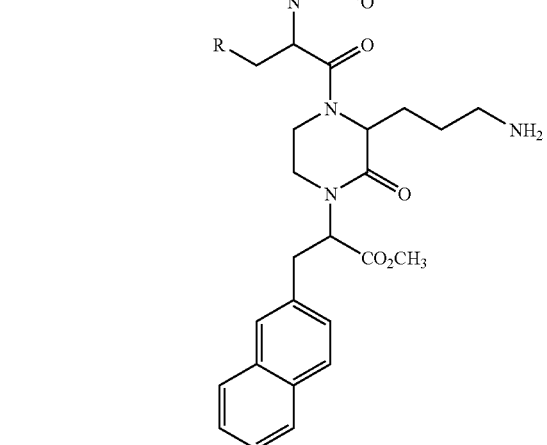
Reagents and conditions: (g) H$_2$: PtO$_2$, MeOH.
Preparation of 3-Ketopiperazine Intermediate
The following is a procedure for preparing the 5-ketopiperazine intermediate having the formula:
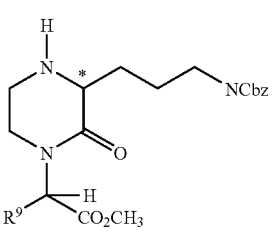
wherein for this example R$^9$ is a 2-naphthyl moiety.

2-[3-(3-Benzyloxycarbonylaminopropyl)-2-oxo-piperazin-1-yl]-3-naphthalen-2-yl-propionic acid methyl ester (42)

Preparation of 2-(5-N-Cbz-amino-2-N-Boc-amino-pentanoylamino)-3-naphthalen-2-yl-propionic acid methyl ester (38): A solution of 1-amino-3-naphthalen-2-yl propionic acid methyl ester (22.9 g, 100 mmol), 5-benzyloxycarbonylamino-2-tert-butoxycarbonylaminopentanoic acid (33.6 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which purified over silica gel.

Preparation of 2-(2-amino-5-N-Cbz-amino-pentanoylamino)-3-naphthalen-2-yl-propionic acid methyl ester (39): 2-(5-N-Cbz-amino-2-N-Boc-amino-pentanoylamino)-3-naphthalen-2-yl-propionic acid methyl ester, 38, (6.0 g, 10.3 mmol) is dissolved in 32 ml of a solution prepared from 2:1:0.1 parts of dichloromethane TFA and water. The reaction mixture is stirred for 3 hours. The solvent is removed in vacuo and the residue treated with 1,2-dichloromethane which is also removed in vacuo. This is repeated several times and affords 9.84 g of the crude rude residue which is used for the next step without further purification.

Preparation of 2-[5-N-Cbz-amino-2-(2-nitro-benzene-sulfonylamino)-pentanoylamino]-3-naphthalen-2-yl-propionic acid methyl ester (40): 2-(2-amino-5-N-Cbz-amino-pentanoylamino)-3-naphthalen-2-yl-propionic acid methyl ester, 39, is dissolved in dichloromethane (200 ml), triethylamine (0.5 ml) and the solution cooled in an ice-bath. o-Nitrosulfonyl chloride (4.5 g, 20.6 mmol) is added and stirring is continued with cooling for 1 hour and then at room temperature for 6 hours. The reaction mixture is treated with 1 M citric acid and the solution is extracted with ethyl acetate. The organic layer is washed with a saturated aqueous solution of sodium carbonate and water. The crude material is purified over silica (1:1 hexanes/ethyl acetate) to afford the desired product (3.6 g).

Preparation of 2-[3-(3-Benzyloxycarbonylamino-propyl)-4-(2-nitro-benzene-sulfonyl)-2-oxo-piperazin-1-yl]-3-naphthalen-2-yl-propionic acid methyl ester (41): A mixture of 2-[5-benzyloxycarbonylamino-2-(2-nitro-benzenesulfonylamino)-pentanoylamino]-3-naphthalen-2-yl-propionic acid methyl ester, 40, (2.4 g, 3.63 mmol), dibromoethane (3.8 mL, 4.36 mmol), potassium carbonate (5.0 g, 36.3 mmol) in DMF (50 mL) is stirred at 55° C. for 18 hours. The reaction mixture is cooled to room temperature, treated with 1M KHSO$_4$ and the resulting solution is extracted with ethyl acetate. The crude product is purified over silica (sequential elution with EtOAc/hexanes mixtures 1:2, 1:1, 100% EtOAc, then EtOAc with 5% MeOH) to afford 2.76 g of the desired product.

Preparation of 2-[3-(3-N-benzyloxycarbonylaminopropyl)-2-oxo-piperazin-1-yl]-3-naphthalen-2-yl-propionic acid methyl ester (42): A mixture of 2-[3-(3-benzyloxycarbonylamino-propyl)-4-(2-nitro-benzenesulfonyl)-2-oxo-piperazin-1-yl]-3-naphthalen-2-yl-propionic acid methyl ester, 41, (1.9 g, 2.8 mmol), p-thiophenol (1.6 g, 12.4 mmol) and K$_2$CO$_3$ (2.3 g, 16.6 mmol) in acetonitrile (10 ml) is stirred at room temperature for 18 hours. The reaction mixture is then concentrated in vacuo and the resulting residue is treated with 1M HCl (10 ml). The aqueous phase is extracted with EtOAc and purified over silica (sequential elution with EtOAc/hexanes mixture 1:1, 100% EtOAc, then EtOAc with 5% MeOH) to afford 2.58 g of the desired product.

The 3-ketopiperazine intermediate having the formula:

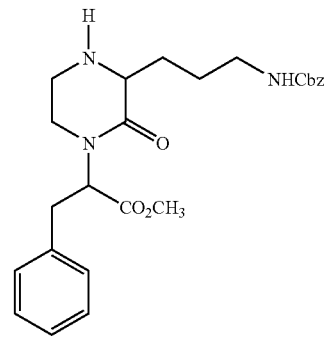

can be prepared by substituting phenylalanine methyl ester for 1-amino-3-naphthalen-2-yl-propionic acid methyl ester in the synthesis of compound 38 described herein above.

EXAMPLE 6

2-[4-[2-[2-Acetylamino-3-(4-hydroxyphenyl)-propionylamino]-3-(4-fluorophenyl)propionyl]-3-(3-aminopropyl)-2-oxo-piperazin-1-yl]-N-methyl-3-naphthalen-2-yl-propionamide (44)

Preparation of 2-[4-[2[2-acetylamino-3-(4-hydroxyphenyl)propionylamino]-3-(4-fluorophenyl)propionyl]-3-(3-N-Cbz-aminopropyl)-2-oxo-piperazin-1-yl]-3-naphthalen-2-yl-propionic acid methyl ester (43): A solution of 2-[3-(3-N-Cbz-aminopropyl)-2-oxo-piperazin-1-yl]-3-naphthalen-2-yl-propionic acid methyl ester, 42, (50.4 g, 100 mmol), 2-[2-acetylamino-3-(4-hydroxyphenyl)-propionylamino]-3-(4-fluorophenyl)propionic acid (38.8 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminoopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which purified over silica gel.

Preparation of 2-[4-[2-[2-acetylamino-3-(4-hydroxyphenyl)propionylamino]-3-(4-fluorophenyl)propionyl]-3-(3-aminopropyl)-2-oxo-piperazin-1-yl]-3-naphthalen-2-yl-propionic acid methyl ester (44): A solution of 2-[4-[2[2-acetylamino-3-(4-hydroxyphenyl)-propionylamino]-3-(4-fluorophenyl)propionyl]-3-(3-N-Cbz-aminopropyl)-2-oxo-piperazin-1-yl]-3-naphthalen-2-yl-propionic acid methyl ester, 43, (8.74 g, 10 mmol) is suspended in methanol (100 ml) and hydrogenated in the presence of 10% Pd/C at 40 psi for 16 hours. The solution is filtered to remove the catalyst and the crude product is purified on a preparative HPLC using a linear gradient of acetonitrile in water with 0.1% TFA to afford the desired product corresponding to analog 287 of Table V.

Another iteration of this category of receptor ligand analogs relates to analogs having the formula:

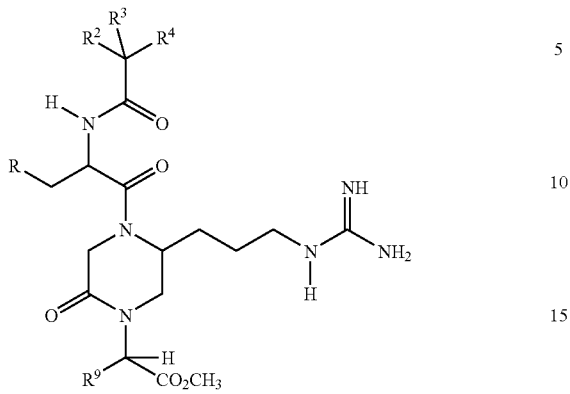

wherein R, $R^2$, $R^3$, $R^4$, and $R^9$ are defined in Table VI.

TABLE VI

| No. | R | $R^2$ | $R^3$ | $R^4$ | $R^9$ |
|---|---|---|---|---|---|
| 301 | phenyl | —NHCOCH$_3$ | H | benzyl | benzyl |
| 302 | 4-chlorophenyl | —NHCOCH$_3$ | H | benzyl | benzyl |
| 303 | 4-fluorophenyl | —NHCOCH$_3$ | H | benzyl | benzyl |
| 304 | 3,4-difluorophenyl | —NHCOCH$_3$ | H | benzyl | benzyl |
| 305 | phenyl | —NHCOCH$_3$ | H | 2-imidazolylmethyl | benzyl |
| 306 | 4-chlorophenyl | —NHCOCH$_3$ | H | 2-imidazolylmethyl | benzyl |
| 307 | 4-fluorophenyl | —NHCOCH$_3$ | H | 2-imidazolylmethyl | benzyl |
| 308 | 3,4-difluorophenyl | —NHCOCH$_3$ | H | 2-imidazolylmethyl | benzyl |
| 309 | phenyl | —NHCOCH$_3$ | H | 4-imidazolylmethyl | benzyl |
| 310 | 4-chlorophenyl | —NHCOCH$_3$ | H | 4-imidazolylmethyl | benzyl |
| 311 | 4-fluorophenyl | —NHCOCH$_3$ | H | 4-imidazolylmethyl | benzyl |
| 312 | 3,4-difluorophenyl | —NHCOCH$_3$ | H | 4-imidazolylmethyl | benzyl |
| 313 | phenyl | —NHCOCH$_3$ | H | 4-fluorobenzyl | benzyl |
| 314 | 4-chlorophenyl | —NHCOCH$_3$ | H | 4-fluorobenzyl | benzyl |
| 315 | 4-fluorophenyl | —NHCOCH$_3$ | H | 4-fluorobenzyl | benzyl |
| 316 | 3,4-difluorophenyl | —NHCOCH$_3$ | H | 4-fluorobenzyl | benzyl |
| 317 | phenyl | —NHCOCH$_3$ | H | 4-hydroxybenzyl | benzyl |
| 318 | 4-chlorophenyl | —NHCOCH$_3$ | H | 4-hydroxybenzyl | benzyl |
| 319 | 4-fluorophenyl | —NHCOCH$_3$ | H | 4-hydroxybenzyl | benzyl |
| 320 | 3,4-difluorophenyl | —NHCOCH$_3$ | H | 4-hydroxybenzyl | benzyl |
| 321 | phenyl | —NHCOCH$_3$ | H | 4-chlorobenzyl | benzyl |
| 322 | 4-chlorophenyl | —NHCOCH$_3$ | H | 4-chlorobenzyl | benzyl |
| 323 | 4-fluorophenyl | —NHCOCH$_3$ | H | 4-chlorobenzyl | benzyl |
| 324 | 3,4-difluorophenyl | —NHCOCH$_3$ | H | 4-chlorobenzyl | benzyl |
| 325 | phenyl | —NHCOCH$_3$ | H | 4-acetoxybenzyl | benzyl |
| 326 | 4-chlorophenyl | —NHCOCH$_3$ | H | 4-acetoxybenzyl | benzyl |
| 327 | 4-fluorophenyl | —NHCOCH$_3$ | H | 4-acetoxybenzyl | benzyl |
| 328 | 3,4-difluorophenyl | —NHCOCH$_3$ | H | 4-acetoxybenzyl | benzyl |
| 329 | phenyl | —NHCOCH$_3$ | H | benzyl | 2-naphthylmethyl |
| 330 | 4-chlorophenyl | —NHCOCH$_3$ | H | benzyl | 2-naphthylmethyl |
| 331 | 4-fluorophenyl | —NHCOCH$_3$ | H | benzyl | 2-naphthylmethyl |
| 332 | 3,4-difluorophenyl | —NHCOCH$_3$ | H | benzyl | 2-naphthylmethyl |
| 333 | phenyl | —NHCOCH$_3$ | H | 2-imidazolylmethyl | 2-naphthylmethyl |
| 334 | 4-chlorophenyl | —NHCOCH$_3$ | H | 2-imidazolylmethyl | 2-naphthylmethyl |
| 335 | 4-fluorophenyl | —NHCOCH$_3$ | H | 2-imidazolylmethyl | 2-naphthylmethyl |
| 336 | 3,4-difluorophenyl | —NHCOCH$_3$ | H | 2-imidazolylmethyl | 2-naphthylmethyl |
| 337 | phenyl | —NHCOCH$_3$ | H | 4-imidazolylmethyl | 2-naphthylmethyl |
| 338 | 4-chlorophenyl | —NHCOCH$_3$ | H | 4-imidazolylmethyl | 2-naphthylmethyl |
| 339 | 4-fluorophenyl | —NHCOCH$_3$ | H | 4-imidazolylmethyl | 2-naphthylmethyl |
| 340 | 3,4-difluorophenyl | —NHCOCH$_3$ | H | 4-imidazolylmethyl | 2-naphthylmethyl |
| 341 | phenyl | —NHCOCH$_3$ | H | 4-fluorobenzyl | 2-naphthylmethyl |
| 342 | 4-chlorophenyl | —NHCOCH$_3$ | H | 4-fluorobenzyl | 2-naphthylmethyl |
| 343 | 4-fluorophenyl | —NHCOCH$_3$ | H | 4-fluorobenzyl | 2-naphthylmethyl |
| 344 | 3,4-difluorophenyl | —NHCOCH$_3$ | H | 4-fluorobenzyl | 2-naphthylmethyl |
| 345 | phenyl | —NHCOCH$_3$ | H | 4-hydroxybenzyl | 2-naphthylmethyl |
| 346 | 4-chlorophenyl | —NHCOCH$_3$ | H | 4-hydroxybenzyl | 2-naphthylmethyl |
| 347 | 4-fluorophenyl | —NHCOCH$_3$ | H | 4-hydroxybenzyl | 2-naphthylmethyl |
| 348 | 3,4-difluorophenyl | —NHCOCH$_3$ | H | 4-hydroxybenzyl | 2-naphthylmethyl |
| 349 | phenyl | —NHCOCH$_3$ | H | 4-chlorobenzyl | 2-naphthylmethyl |
| 350 | 4-chlorophenyl | —NHCOCH$_3$ | H | 4-chlorobenzyl | 2-naphthylmethyl |
| 351 | 4-fluorophenyl | —NHCOCH$_3$ | H | 4-chlorobenzyl | 2-naphthylmethyl |
| 352 | 3,4-difluorophenyl | —NHCOCH$_3$ | H | 4-chlorobenzyl | 2-naphthylmethyl |

TABLE VI-continued

| No. | R | R² | R³ | R⁴ | R⁹ |
|---|---|---|---|---|---|
| 353 | phenyl | —NHCOCH₃ | H | 4-acetoxybenzyl | 2-naphthylmethyl |
| 354 | 4-chlorophenyl | —NHCOCH₃ | H | 4-acetoxybenzyl | 2-naphthylmethyl |
| 355 | 4-fluorophenyl | —NHCOCH₃ | H | 4-acetoxybenzyl | 2-naphthylmethyl |
| 356 | 3,4-difluorophenyl | —NHCOCH₃ | H | 4-acetoxybenzyl | 2-naphthylmethyl |
| 357 | 4-hydroxyphenyl | —NHCOCH₃ | H | 2-imidazolylmethyl | 2-naphthylmethyl |
| 358 | 4-hydroxyphenyl | —NHCOCH₃ | H | 4-fluorobenzyl | 2-naphthylmethyl |
| 359 | 4-hydroxyphenyl | —NHCOCH₃ | H | 4-hydroxybenzyl | 2-naphthylmethyl |
| 360 | 4-hydroxyphenyl | —NHCOCH₃ | H | 4-chlorobenzyl | 2-naphthylmethyl |

The following is an outline of a synthetic pathway for preparing analogs 301–360, however, other embodiments of the 3-ketopiperazine scaffold can be prepared using modifications to this general scheme.

Reagents and conditions: (h) BocNHC(SCH₃)=NBoc, HgCl₂, rt.

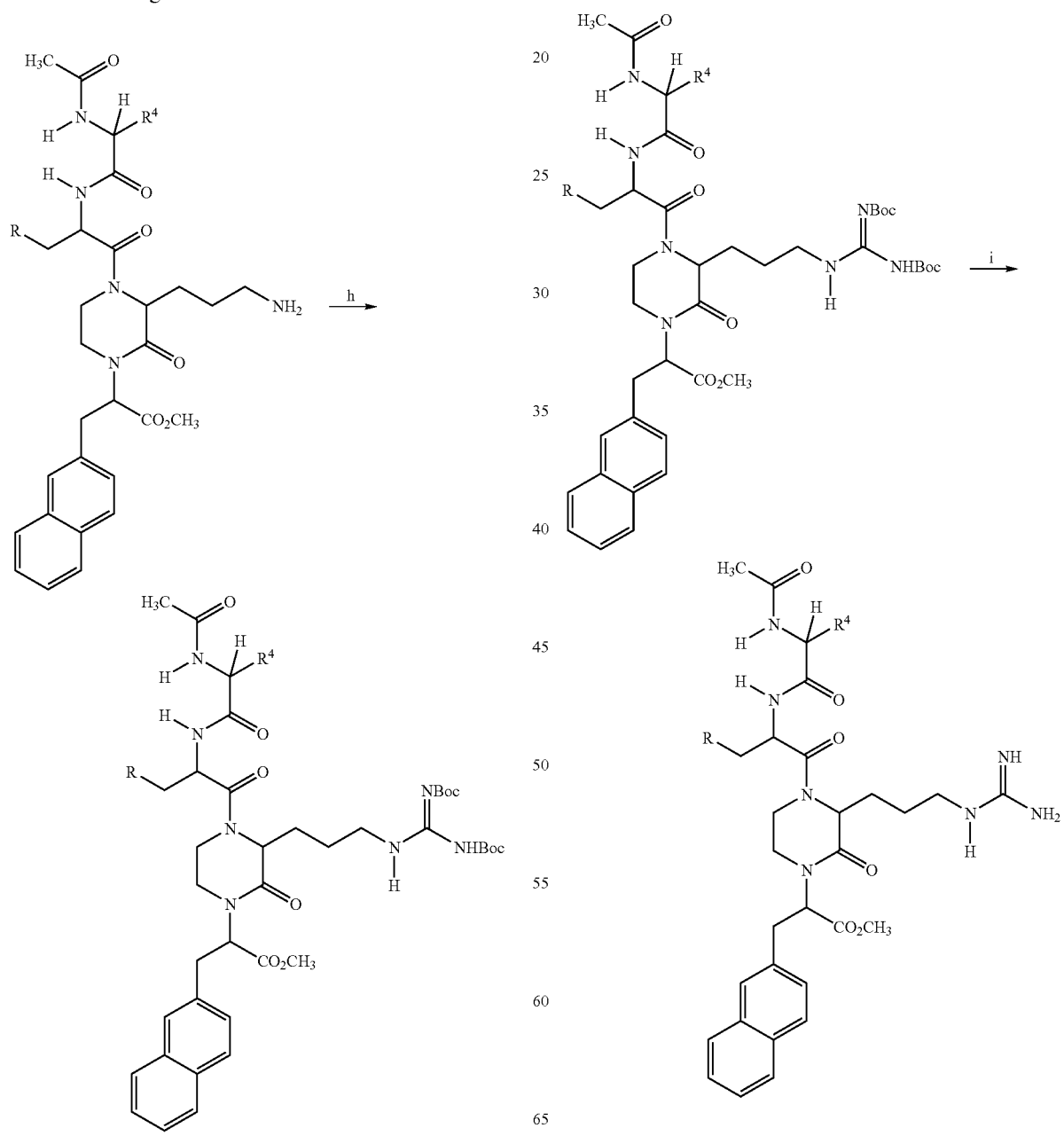

Reagents and conditions: (i) TFA:CH₂Cl₂, rt;

EXAMPLE 7

2-[4-[2-[2-Acetylamino-3-(4-hydroxyphenyl)propionylamino]-3-(4-fluorophenyl)propionyl]-3-(3-guanidinopropyl)-2-oxo-piperazin-1-yl-propionic acid methyl ester (46)

Preparation of 2-[4-[2-[2-Acetylamino-3-(4-hydroxyphenyl)propionylamino]-3-(4-fuorophenyl)propionyl]-3-(3-N,N'-bis(tert-butoxycarbonyl)guanidinopropyl)-2-oxo-piperazin-1-yl-propionic acid methyl ester (45): Mercury(II) chloride (5.7 g, 12 mmol) is added to a solution 2-[4-[2-[2-acetylamino-3-(4-hydroxyphenyl)propionylamino]-3-(4-fluorophenyl)propionyl]-3-(3-aminopropyl)-2-oxo-piperazin-1-yl]-3-naphthalen-2-yl-propion acid methyl ester, 44, (7.4, 10 mmol), 1,3-bis(tert-butoxycarbonyl)-2-methyl-2-thiopseudo urea (2.9 g, 10 mmol) and triethylamine (4.2 mL, 30 mmol) in dry DMF (100.0 mL) and the reaction mixture is stirred at 0° C. for 1.0 hour. The reaction mixture is then diluted with EtOAc, filtered through a pad of Celite, and the filtrate is concentrated in vacuo to afford the crude product. The crude isolate is purified over silica gel ($CH_2Cl_2$/methanol, 14:1) to afford the desired product.

Preparation of 2-[4-[2-[2-Acetylamino-3-(4-hydroxyphenyl)propionylamino]-3-(4-fluorophenyl)propionyl]-3-(3-guanidinopropyl)-2-oxo-piperazin-1-yl-propionic acid methyl ester (46) A solution of 2-[4-[2-[2-Acetylamino-3-(4-hydroxyphenyl)propionylamino]-3-(4-fluorophenyl)propionyl]-3-(3-N,N'-bis(tert-butoxycarbonyl)guanidinopropyl)-2-oxo-piperazin-1-yl-propionic acid methyl ester, 45, (10.4 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Another iteration of this category relates to analogs wherein $R^{10}$ is a —$CONH_2$ unit which provides receptor ligands having the formula:

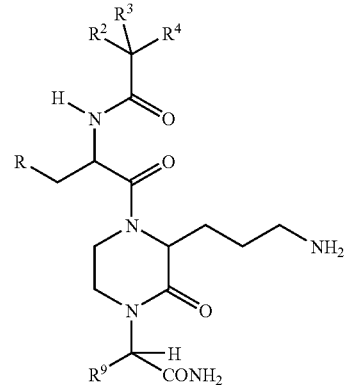

wherein R, $R^2$, $R^3$, $R^4$, and $R^9$ are defined in Table VII or receptor ligands having the formula:

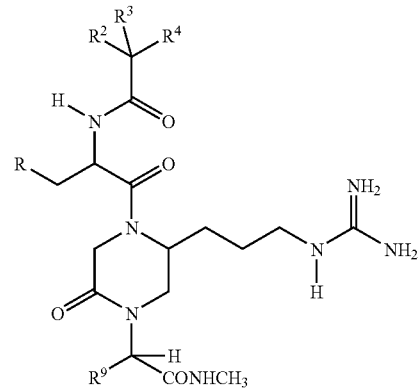

wherein R, $R^2$, $R^3$, $R^4$, and $R^9$ are defined in Table VIII.

TABLE VII

| No. | R | $R^2$ | $R^3$ | $R^4$ | $R^9$ |
|---|---|---|---|---|---|
| 361 | phenyl | —$NHCOCH_3$ | H | benzyl | benzyl |
| 362 | 4-chlorophenyl | —$NHCOCH_3$ | H | benzyl | benzyl |
| 363 | 4-fluorophenyl | —$NHCOCH_3$ | H | benzyl | benzyl |
| 364 | 3,4-difluorophenyl | —$NHCOCH_3$ | H | benzyl | benzyl |
| 365 | phenyl | —$NHCOCH_3$ | H | 2-imidazolylmethyl | benzyl |
| 366 | 4-chlorophenyl | —$NHCOCH_3$ | H | 2-imidazolylmethyl | benzyl |
| 367 | 4-fluorophenyl | —$NHCOCH_3$ | H | 2-imidazolylmethyl | benzyl |
| 368 | 3,4-difluorophenyl | —$NHCOCH_3$ | H | 2-imidazolylmethyl | benzyl |
| 369 | phenyl | —$NHCOCH_3$ | H | 4-imidazolylmethyl | benzyl |
| 370 | 4-chlorophenyl | —$NHCOCH_3$ | H | 4-imidazolylmethyl | benzyl |
| 371 | 4-fluorophenyl | —$NHCOCH_3$ | H | 4-imidazolylmethyl | benzyl |
| 372 | 3,4-difluorophenyl | —$NHCOCH_3$ | H | 4-imidazolylmethyl | benzyl |
| 373 | phenyl | —$NHCOCH_3$ | H | 4-fluorobenzyl | benzyl |
| 374 | 4-chlorophenyl | —$NHCOCH_3$ | H | 4-fluorobenzyl | benzyl |
| 375 | 4-fluorophenyl | —$NHCOCH_3$ | H | 4-fluorobenzyl | benzyl |
| 376 | 3,4-difluorophenyl | —$NHCOCH_3$ | H | 4-fluorobenzyl | benzyl |
| 377 | phenyl | —$NHCOCH_3$ | H | 4-hydroxybenzyl | benzyl |
| 378 | 4-chlorophenyl | —$NHCOCH_3$ | H | 4-hydroxybenzyl | benzyl |
| 379 | 4-fluorophenyl | —$NHCOCH_3$ | H | 4-hydroxybenzyl | benzyl |
| 380 | 3,4-difluorophenyl | —$NHCOCH_3$ | H | 4-hydroxybenzyl | benzyl |
| 381 | phenyl | —$NHCOCH_3$ | H | 4-chlorobenzyl | benzyl |
| 382 | 4-chlorophenyl | —$NHCOCH_3$ | H | 4-chlorobenzyl | benzyl |

TABLE VII-continued

| No. | R | R² | R³ | R⁴ | R⁹ |
|---|---|---|---|---|---|
| 383 | 4-fluorophenyl | —NHCOCH₃ | H | 4-chlorobenzyl | benzyl |
| 384 | 3,4-difluorophenyl | —NHCOCH₃ | H | 4-chlorobenzyl | benzyl |
| 385 | phenyl | —NHCOCH₃ | H | 4-acetoxybenzyl | benzyl |
| 386 | 4-chlorophenyl | —NHCOCH₃ | H | 4-acetoxybenzyl | benzyl |
| 387 | 4-fluorophenyl | —NHCOCH₃ | H | 4-acetoxybenzyl | benzyl |
| 388 | 3,4-difluorophenyl | —NHCOCH₃ | H | 4-acetoxybenzyl | benzyl |
| 389 | phenyl | —NHCOCH₃ | H | benzyl | 2-naphthylmethyl |
| 390 | 4-chlorophenyl | —NHCOCH₃ | H | benzyl | 2-naphthylmethyl |
| 391 | 4-fluorophenyl | —NHCOCH₃ | H | benzyl | 2-naphthylmethyl |
| 392 | 3,4-difluorophenyl | —NHCOCH₃ | H | benzyl | 2-naphthylmethyl |
| 393 | phenyl | —NHCOCH₃ | H | 2-imidazolylmethyl | 2-naphthylmethyl |
| 394 | 4-chlorophenyl | —NHCOCH₃ | H | 2-imidazolylmethyl | 2-naphthylmethyl |
| 395 | 4-fluorophenyl | —NHCOCH₃ | H | 2-imidazolylmethyl | 2-naphthylmethyl |
| 396 | 3,4-difluorophenyl | —NHCOCH₃ | H | 2-imidazolylmethyl | 2-naphthylmethyl |
| 397 | phenyl | —NHCOCH₃ | H | 4-imidazolylmethyl | 2-naphthylmethyl |
| 398 | 4-chlorophenyl | —NHCOCH₃ | H | 4-imidazolylmethyl | 2-naphthylmethyl |
| 399 | 4-fluorophenyl | —NHCOCH₃ | H | 4-imidazolylmethyl | 2-naphthylmethyl |
| 400 | 3,4-difluorophenyl | —NHCOCH₃ | H | 4-imidazolylmethyl | 2-naphthylmethyl |
| 401 | phenyl | —NHCOCH₃ | H | 4-fluorobenzyl | 2-naphthylmethyl |
| 402 | 4-chlorophenyl | —NHCOCH₃ | H | 4-fluorobenzyl | 2-naphthylmethyl |
| 403 | 4-fluorophenyl | —NHCOCH₃ | H | 4-fluorobenzyl | 2-naphthylmethyl |
| 404 | 3,4-difluorophenyl | —NHCOCH₃ | H | 4-fluorobenzyl | 2-naphthylmethyl |
| 405 | phenyl | —NHCOCH₃ | H | 4-hydroxybenzyl | 2-naphthylmethyl |
| 406 | 4-chlorophenyl | —NHCOCH₃ | H | 4-hydroxybenzyl | 2-naphthylmethyl |
| 407 | 4-fluorophenyl | —NHCOCH₃ | H | 4-hydroxybenzyl | 2-naphthylmethyl |
| 408 | 3,4-difluorophenyl | —NHCOCH₃ | H | 4-hydroxybenzyl | 2-naphthylmethyl |
| 409 | phenyl | —NHCOCH₃ | H | 4-chlorobenzyl | 2-naphthylmethyl |
| 410 | 4-chlorophenyl | —NHCOCH₃ | H | 4-chlorobenzyl | 2-naphthylmethyl |
| 411 | 4-fluorophenyl | —NHCOCH₃ | H | 4-chlorobenzyl | 2-naphthylmethyl |
| 412 | 3,4-difluorophenyl | —NHCOCH₃ | H | 4-chlorobenzyl | 2-naphthylmethyl |
| 413 | phenyl | —NHCOCH₃ | H | 4-acetoxybenzyl | 2-naphthylmethyl |
| 414 | 4-chlorophenyl | —NHCOCH₃ | H | 4-acetoxybenzyl | 2-naphthylmethyl |
| 415 | 4-fluorophenyl | —NHCOCH₃ | H | 4-acetoxybenzyl | 2-naphthylmethyl |
| 416 | 3,4-difluorophenyl | —NHCOCH₃ | H | 4-acetoxybenzyl | 2-naphthylmethyl |
| 417 | 4-hydroxyphenyl | —NHCOCH₃ | H | 2-imidazolylmethyl | 2-naphthylmethyl |
| 418 | 4-hydroxyphenyl | —NHCOCH₃ | H | 4-fluorobenzyl | 2-naphthylmethyl |
| 419 | 4-hydroxyphenyl | —NHCOCH₃ | H | 4-hydroxybenzyl | 2-naphthylmethyl |
| 420 | 4-hydroxyphenyl | —NHCOCH₃ | H | 4-chlorobenzyl | 2-naphthylmethyl |

TABLE VIII

| No. | R | R² | R³ | R⁴ | R⁹ |
|---|---|---|---|---|---|
| 421 | phenyl | —NHCOCH₃ | H | benzyl | benzyl |
| 422 | 4-chlorophenyl | —NHCOCH₃ | H | benzyl | benzyl |
| 423 | 4-fluorophenyl | —NHCOCH₃ | H | benzyl | benzyl |
| 424 | 3,4-difluorophenyl | —NHCOCH₃ | H | benzyl | benzyl |
| 425 | phenyl | —NHCOCH₃ | H | 2-imidazolylmethyl | benzyl |
| 426 | 4-chlorophenyl | —NHCOCH₃ | H | 2-imidazolylmethyl | benzyl |
| 427 | 4-fluorophenyl | —NHCOCH₃ | H | 2-imidazolylmethyl | benzyl |
| 428 | 3,4-difluorophenyl | —NHCOCH₃ | H | 2-imidazolylmethyl | benzyl |
| 429 | phenyl | —NHCOCH₃ | H | 4-imidazolylmethyl | benzyl |
| 430 | 4-chlorophenyl | —NHCOCH₃ | H | 4-imidazolylmethyl | benzyl |
| 431 | 4-fluorophenyl | —NHCOCH₃ | H | 4-imidazolylmethyl | benzyl |
| 432 | 3,4-difluorophenyl | —NHCOCH₃ | H | 4-imidazolylmethyl | benzyl |
| 433 | phenyl | —NHCOCH₃ | H | 4-fluorobenzyl | benzyl |
| 434 | 4-chlorophenyl | —NHCOCH₃ | H | 4-fluorobenzyl | benzyl |
| 435 | 4-fluorophenyl | —NHCOCH₃ | H | 4-fluorobenzyl | benzyl |
| 436 | 3,4-difluorophenyl | —NHCOCH₃ | H | 4-fluorobenzyl | benzyl |
| 437 | phenyl | —NHCOCH₃ | H | 4-hydroxybenzyl | benzyl |
| 438 | 4-chlorophenyl | —NHCOCH₃ | H | 4-hydroxybenzyl | benzyl |
| 439 | 4-fluorophenyl | —NHCOCH₃ | H | 4-hydroxybenzyl | benzyl |
| 440 | 3,4-difluorophenyl | —NHCOCH₃ | H | 4-hydroxybenzyl | benzyl |
| 441 | phenyl | —NHCOCH₃ | H | 4-chlorobenzyl | benzyl |
| 442 | 4-chlorophenyl | —NHCOCH₃ | H | 4-chlorobenzyl | benzyl |
| 443 | 4-fluorophenyl | —NHCOCH₃ | H | 4-chlorobenzyl | benzyl |
| 444 | 3,4-difluorophenyl | —NHCOCH₃ | H | 4-chlorobenzyl | benzyl |
| 445 | phenyl | —NHCOCH₃ | H | 4-acetoxybenzyl | benzyl |
| 446 | 4-chlorophenyl | —NHCOCH₃ | H | 4-acetoxybenzyl | benzyl |
| 447 | 4-fluorophenyl | —NHCOCH₃ | H | 4-acetoxybenzyl | benzyl |
| 448 | 3,4-difluorophenyl | —NHCOCH₃ | H | 4-acetoxybenzyl | benzyl |

TABLE VIII-continued

| No. | R | $R^2$ | $R^3$ | $R^4$ | $R^9$ |
|---|---|---|---|---|---|
| 449 | phenyl | —NHCOCH₃ | H | benzyl | 2-naphthylmethyl |
| 450 | 4-chlorophenyl | —NHCOCH₃ | H | benzyl | 2-naphthylmethyl |
| 451 | 4-fluorophenyl | —NHCOCH₃ | H | benzyl | 2-naphthylmethyl |
| 452 | 3,4-difluorophenyl | —NHCOCH₃ | H | benzyl | 2-naphthylmethyl |
| 453 | phenyl | —NHCOCH₃ | H | 2-imidazolylmethyl | 2-naphthylmethyl |
| 454 | 4-chlorophenyl | —NHCOCH₃ | H | 2-imidazolylmethyl | 2-naphthylmethyl |
| 455 | 4-fluorophenyl | —NHCOCH₃ | H | 2-imidazolylmethyl | 2-naphthylmethyl |
| 456 | 3,4-difluorophenyl | —NHCOCH₃ | H | 2-imidazolylmethyl | 2-naphthylmethyl |
| 457 | phenyl | —NHCOCH₃ | H | 4-imidazolylmethyl | 2-naphthylmethyl |
| 458 | 4-chlorophenyl | —NHCOCH₃ | H | 4-imidazolylmethyl | 2-naphthylmethyl |
| 459 | 4-fluorophenyl | —NHCOCH₃ | H | 4-imidazolylmethyl | 2-naphthylmethyl |
| 460 | 3,4-difluorophenyl | —NHCOCH₃ | H | 4-imidazolylmethyl | 2-naphthylmethyl |
| 461 | phenyl | —NHCOCH₃ | H | 4-fluorobenzyl | 2-naphthylmethyl |
| 462 | 4-chlorophenyl | —NHCOCH₃ | H | 4-fluorobenzyl | 2-naphthylmethyl |
| 463 | 4-fluorophenyl | —NHCOCH₃ | H | 4-fluorobenzyl | 2-naphthylmethyl |
| 464 | 3,4-difluorophenyl | —NHCOCH₃ | H | 4-fluorobenzyl | 2-naphthylmethyl |
| 465 | phenyl | —NHCOCH₃ | H | 4-hydroxybenzyl | 2-naphthylmethyl |
| 466 | 4-chlorophenyl | —NHCOCH₃ | H | 4-hydroxybenzyl | 2-naphthylmethyl |
| 467 | 4-fluorophenyl | —NHCOCH₃ | H | 4-hydroxybenzyl | 2-naphthylmethyl |
| 468 | 3,4-difluorophenyl | —NHCOCH₃ | H | 4-hydroxybenzyl | 2-naphthylmethyl |
| 469 | phenyl | —NHCOCH₃ | H | 4-chlorobenzyl | 2-naphthylmethyl |
| 470 | 4-chlorophenyl | —NHCOCH₃ | H | 4-chlorobenzyl | 2-naphthylmethyl |
| 471 | 4-fluorophenyl | —NHCOCH₃ | H | 4-chlorobenzyl | 2-naphthylmethyl |
| 472 | 3,4-difluorophenyl | —NHCOCH₃ | H | 4-chlorobenzyl | 2-naphthylmethyl |
| 473 | phenyl | —NHCOCH₃ | H | 4-acetoxybenzyl | 2-naphthylmethyl |
| 474 | 4-chlorophenyl | —NHCOCH₃ | H | 4-acetoxybenzyl | 2-naphthylmethyl |
| 475 | 4-fluorophenyl | —NHCOCH₃ | H | 4-acetoxybenzyl | 2-naphthylmethyl |
| 476 | 3,4-difluorophenyl | —NHCOCH₃ | H | 4-acetoxybenzyl | 2-naphthylmethyl |
| 477 | 4-hydroxyphenyl | —NHCOCH₃ | H | 2-imidazolylmethyl | 2-naphthylmethyl |
| 478 | 4-hydroxyphenyl | —NHCOCH₃ | H | 4-fluorobenzyl | 2-naphthylmethyl |
| 479 | 4-hydroxyphenyl | —NHCOCH₃ | H | 4-hydroxybenzyl | 2-naphthylmethyl |
| 480 | 4-hydroxyphenyl | —NHCOCH₃ | H | 4-chlorobenzyl | 2-naphthylmethyl |

The following is an outline of a synthetic pathway for preparing analogs 361–420. In the following scheme $R^9$ is 2-naphthylmethyl, however, other embodiments of this piperazine scaffold can be prepared using modifications to this general scheme. For example, when phenylalanine is substituted for 1-amino-3-naphthalen-2-yl propionic acid in the synthesis of compound 38, the result is analogs wherein $R^9$ is benzyl.

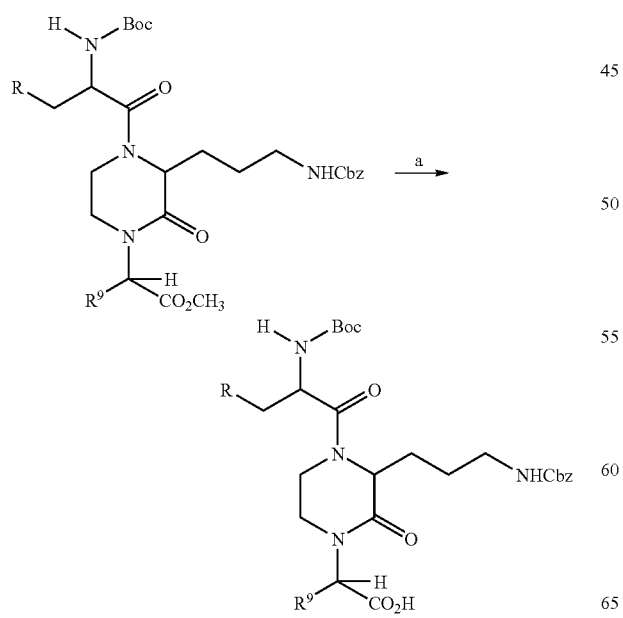

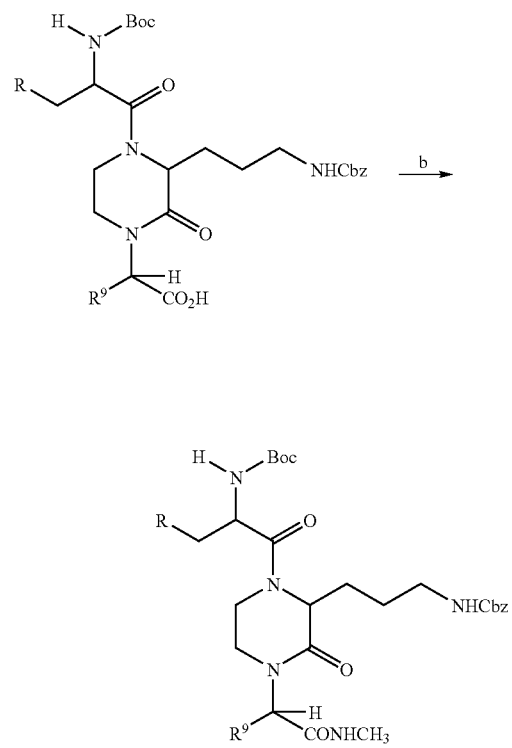

Reagents and conditions: (a) LiOH, 0°C.

Reagents and conditions: (b) NH₂CH₃, PyBOP, rt.

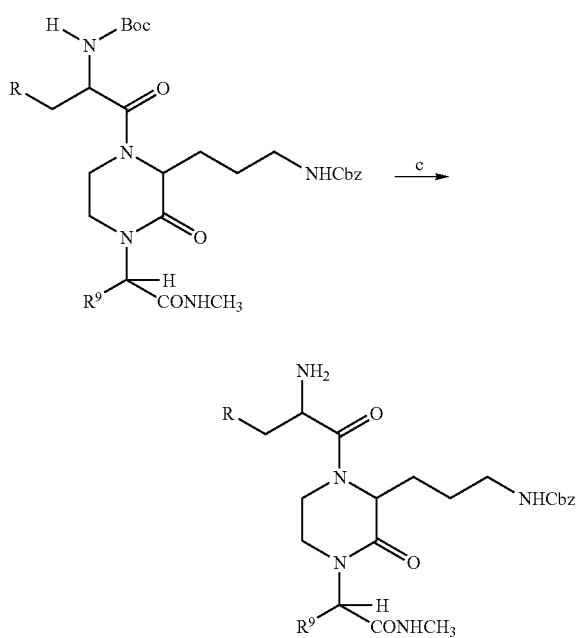

Reagents and conditions: (c) TFA/CH₂Cl₂, rt.

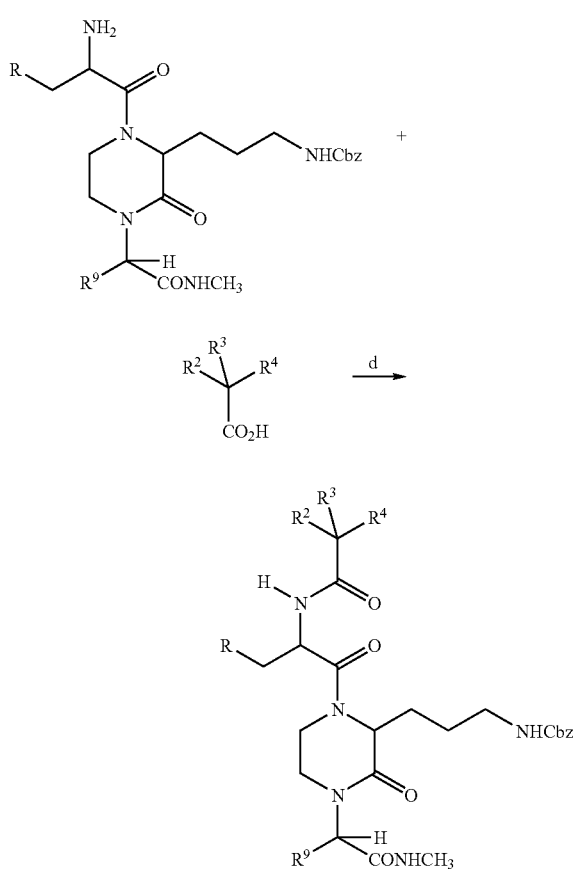

Reagents and conditions: (d) HOBt, EDCI, N-methylmorpholine, DMF, 0°C.

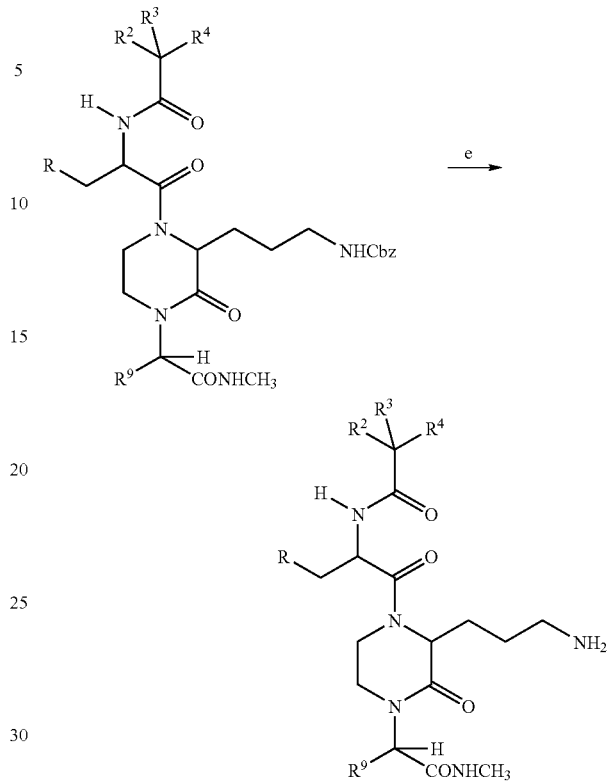

Reagents and conditions: (e) H₂, 10% Pd/C; MeOH.

EXAMPLE 8

2-4-[2-[2-Acetylamino-3-(4-hydroxyphenyl)propionylamino]-3-(4-fluorophenyl)propionyl]-3-(3-aminopropyl)-2-oxo-piperazin-1-yl]-N-methyl-3-naphthalen-2-yl-propionamide (51)

Preparation of 2-{3-(N-Cbz-aminopropyl)-4-[2-N-Boc-amino-3-(4-fluorophenyl)-propionyl-2-oxo-piperazin-1-yl)-3-napthalen-2-yl propionic acid (47): A mixture 2-[5-N-Cbz-amino-2-(2-N-Boc-amino)pentanoylamino]-3-naphthalen-2-yl-propionic acid methyl ester (0.755 g, 1 mmol) in THF (15 ml) is cooled in an ice-bath and treated with a solution of LiOH (0.12 g, 5 mmol) in water (7.5 ml). The solution is stirred for 1 hour at 0° C. then allowed to warm to room temperature and stir an additional 3 hours. The reaction is then diluted with water (30 ml), cooled in an ice-bath and acidified with 1M HCl to pH 3–4. The resulting solution is extracted with EtOAc. The organic phase is dried and concentrated in vacuo to afford 0.58 g (75%) of the desired product.

Preparation of {3-[1-[2-N-Boc-amino-3-(4-fluorophenyl)propionyl]-4-(1-methylcarbamoyl-2-naphthalen-2-ylethyl)-3-oxo-piperazin-2-yl]propyl}-carbamic acid benzyl ester (48): To a mixture of 2-{3-(N-Cbz-aminopropyl)-4-[2-N-Boc-amino-3-(4-fluorophenyl)-propionyl-2-oxo-piperazin-1-yl)-3-napthalen-2-yl propionic acid, 47, (0.6 g, 0.77 mmol), 2 M methylamine (3 ml), in DMF (15 ml) is added benzotriazole-1-yl-oxy-tris-pyrrolidinol-phosphonium hexafluorophosphate (PyBOP) (0.6 g, 1.15 mmol). The solution is stirred for 18 hours then diluted with water (80 ml) and the solution extracted with EtOAc. The organic phase is dried, concentrated in vacuo and the resulting crude product is purified over silica gel (EtOAc/hexanes 1:3, followed by 1:1 and 10% methanol in EtOAc) to afford 0.56 g of the desired product.

Preparation of {3-[1-[2-amino-3-(4-fluorophenyl)propionyl]-4-(1-methylcarbamoyl-2-naphtyalen-2-ylethyl)-3-oxo-piperazin-2-yl]propyl}-carbamic acid benzyl ester (49): A solution of 3-[1-[2-N-Boc-amino-3-(4-fluorophenyl)propionyl]-4-(1-methylcarbamoyl-2-naphthalen-2-ylethyl)-3-oxo-piperazin-2-yl]propyl}-carbamic acid benzyl ester, 48, trifluoroacetic acid (50 mL), and dichloromethane (500 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Preparation of {3-[1-[2-[2-acetylamino-2-(4-hydroxyphenyl)-2-acetyamino]-3-(4-fluorophenylpropionyl]-4-(1-methylcarbamoyl-2-naphthylen-2-ylethyl)-3-oxo-piperazin-2-yl]propyl}-carbamic acid benzyl ester (50): {3-[1-[2-amino-3-(4-fluorophenyl)propionyl]-4-(1-methylcarbamoyl-2-naphtyalen-2-ylethyl)-3-oxo-piperazin-2-yl]propyl}-carbamic acid benzyl ester, 49, (66.8 g, 100 mmol), N-acetyl-L-tyrosine (26.8 g, 120 mmol), 1-hydroxybenzotriazole (16.2 g, 120 mmol), and N-methylmorpholine (132 mL, 120 mmol) in DMF (150 mL) is cooled to 0° C. and 1-(3-dimethylaminoopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford the desired compound.

Preparation of 2-4-[2-[2-acetylamino-3-(4-hydroxyphenyl)propionylamino]-3-(4-fluorophenyl)propionyl]-3-(3-aminopropyl)-2-oxo-piperazin-1-yl]-N-methyl-3-naphthalen-2-yl-propionamide (51): {3-[1-[2-[2-acetylamino-2-(4-hydroxyphenyl)-2-acetyamino]-3-(4-fluorophenylpropionyl]-4-(1-methylcarbamoyl-2-naphthylen-2-ylethyl)-3-oxo-piperazin-2-yl]propyl}-carbamic acid benzyl ester, 50, (8.59 g, 10 mmol) is suspended in methanol (100 ml) and hydrogenated in the presence of 10% Pd/C at 40 psi for 16 hours. The solution is filtered to remove the catalyst and the crude product is purified on a preparative HPLC using a linear gradient of acetonitrile in water with 0.1% TFA to afford the desired product, receptor ligand analog 457.

The receptor ligands of the present invention exemplified in Table VIII, analogs 421–480 comprise a guanidinopropyl moiety. These analogs can be suitably prepared by modifying the procedures which are described hereinabove for converting compound 35 to compound 37.

Another aspect of the present invention relates to 3-ketopiperazine receptor ligands having the formula:

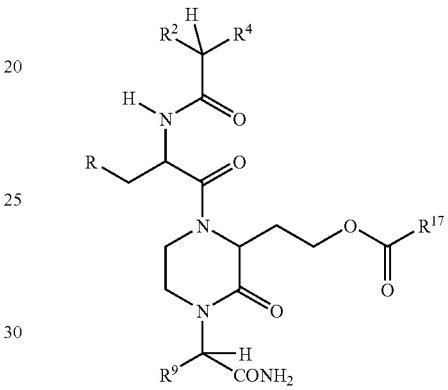

wherein R, $R^2$, $R^4$, $R^9$ and $R^{17}$ are defined in Table IX herein below.

TABLE IX

| No. | R | $R^2$ | $R^3$ | $R^9$ | $R^{17}$ |
|---|---|---|---|---|---|
| 481 | phenyl | —NHCOCH$_3$ | benzyl | phenyl | methyl |
| 482 | 4-chlorophenyl | —NHCOCH$_3$ | benzyl | phenyl | methyl |
| 483 | 4-fluorophenyl | —NHCOCH$_3$ | benzyl | phenyl | methyl |
| 484 | 3,4-difluorophenyl | —NHCOCH$_3$ | benzyl | phenyl | methyl |
| 485 | phenyl | —NHCOCH$_3$ | 2-imidazolylmethyl | phenyl | methyl |
| 486 | 4-chlorophenyl | —NHCOCH$_3$ | 2-imidazolylmethyl | phenyl | methyl |
| 487 | 4-fluorophenyl | —NHCOCH$_3$ | 2-imidazolylmethyl | phenyl | methyl |
| 488 | 3,4-difluorophenyl | —NHCOCH$_3$ | 2-imidazolylmethyl | phenyl | methyl |
| 489 | phenyl | —NHCOCH$_3$ | 4-imidazolylmethyl | phenyl | methyl |
| 490 | 4-chlorophenyl | —NHCOCH$_3$ | 4-imidazolylmethyl | phenyl | methyl |
| 491 | 4-fluorophenyl | —NHCOCH$_3$ | 4-imidazolylmethyl | phenyl | methyl |
| 492 | 3,4-difluorophenyl | —NHCOCH$_3$ | 4-imidazolylmethyl | phenyl | methyl |
| 493 | phenyl | —NHCOCH$_3$ | 4-fluorobenzyl | phenyl | methyl |
| 494 | 4-chlorophenyl | —NHCOCH$_3$ | 4-fluorobenzyl | phenyl | methyl |
| 495 | 4-fluorophenyl | —NHCOCH$_3$ | 4-fluorobenzyl | phenyl | methyl |
| 496 | 3,4-difluorophenyl | —NHCOCH$_3$ | 4-fluorobenzyl | phenyl | methyl |
| 497 | phenyl | —NHCOCH$_3$ | 4-hydroxybenzyl | phenyl | methyl |
| 498 | 4-chlorophenyl | —NHCOCH$_3$ | 4-hydroxybenzyl | phenyl | methyl |
| 499 | 4-fluorophenyl | —NHCOCH$_3$ | 4-hydroxybenzyl | phenyl | methyl |
| 500 | 3,4-difluorophenyl | —NHCOCH$_3$ | 4-hydroxybenzyl | phenyl | methyl |
| 501 | phenyl | —NHCOCH$_3$ | 4-chlorobenzyl | phenyl | methyl |
| 502 | 4-chlorophenyl | —NHCOCH$_3$ | 4-chlorobenzyl | phenyl | methyl |
| 503 | 4-fluorophenyl | —NHCOCH$_3$ | 4-chlorobenzyl | phenyl | methyl |
| 504 | 3,4-difluorophenyl | —NHCOCH$_3$ | 4-chlorobenzyl | phenyl | methyl |
| 505 | phenyl | —NHCOCH$_3$ | 4-acetoxybenzyl | phenyl | methyl |
| 506 | 4-chlorophenyl | —NHCOCH$_3$ | 4-acetoxybenzyl | phenyl | methyl |
| 507 | 4-fluorophenyl | —NHCOCH$_3$ | 4-acetoxybenzyl | phenyl | methyl |
| 508 | 3,4-difluorophenyl | —NHCOCH$_3$ | 4-acetoxybenzyl | phenyl | methyl |
| 509 | phenyl | —NHCOCH$_3$ | benzyl | 2-naphthylmethyl | methyl |
| 510 | 4-chlorophenyl | —NHCOCH$_3$ | benzyl | 2-naphthylmethyl | methyl |
| 511 | 4-fluorophenyl | —NHCOCH$_3$ | benzyl | 2-naphthylmethyl | methyl |
| 512 | 3,4-difluorophenyl | —NHCOCH$_3$ | benzyl | 2-naphthylmethyl | methyl |

TABLE IX-continued

| No. | R | $R^2$ | $R^3$ | $R^9$ | $R^{17}$ |
|---|---|---|---|---|---|
| 513 | phenyl | —NHCOCH$_3$ | 2-imidazolylmethyl | 2-naphthylmethyl | methyl |
| 514 | 4-chlorophenyl | —NHCOCH$_3$ | 2-imidazolylmethyl | 2-naphthylmethyl | methyl |
| 515 | 4-fluorophenyl | —NHCOCH$_3$ | 2-imidazolylmethyl | 2-naphthylmethyl | methyl |
| 516 | 3,4-difluorophenyl | —NHCOCH$_3$ | 2-imidazolylmethyl | 2-naphthylmethyl | methyl |
| 517 | phenyl | —NHCOCH$_3$ | 4-imidazolylmethyl | 2-naphthylmethyl | methyl |
| 518 | 4-chlorophenyl | —NHCOCH$_3$ | 4-imidazolylmethyl | 2-naphthylmethyl | methyl |
| 519 | 4-fluorophenyl | —NHCOCH$_3$ | 4-imidazolylmethyl | 2-naphthylmethyl | methyl |
| 520 | 3,4-difluorophenyl | —NHCOCH$_3$ | 4-imidazolylmethyl | 2-naphthylmethyl | methyl |
| 521 | phenyl | —NHCOCH$_3$ | 4-fluorobenzyl | 2-naphthylmethyl | methyl |
| 522 | 4-chlorophenyl | —NHCOCH$_3$ | 4-fluorobenzyl | 2-naphthylmethyl | methyl |
| 523 | 4-fluorophenyl | —NHCOCH$_3$ | 4-fluorobenzyl | 2-naphthylmethyl | methyl |
| 524 | 3,4-difluorophenyl | —NHCOCH$_3$ | 4-fluorobenzyl | 2-naphthylmethyl | methyl |
| 525 | phenyl | —NHCOCH$_3$ | 4-hydroxybenzyl | 2-naphthylmethyl | methyl |
| 526 | 4-chlorophenyl | —NHCOCH$_3$ | 4-hydroxybenzyl | 2-naphthylmethyl | methyl |
| 527 | 4-fluorophenyl | —NHCOCH$_3$ | 4-hydroxybenzyl | 2-naphthylmethyl | methyl |
| 528 | 3,4-difluorophenyl | —NHCOCH$_3$ | 4-hydroxybenzyl | 2-naphthylmethyl | methyl |
| 529 | phenyl | —NHCOCH$_3$ | 4-chlorobenzyl | 2-naphthylmethyl | methyl |
| 530 | 4-chlorophenyl | —NHCOCH$_3$ | 4-chlorobenzyl | 2-naphthylmethyl | methyl |
| 531 | 4-fluorophenyl | —NHCOCH$_3$ | 4-chlorobenzyl | 2-naphthylmethyl | methyl |
| 532 | 3,4-difluorophenyl | —NHCOCH$_3$ | 4-chlorobenzyl | 2-naphthylmethyl | methyl |
| 533 | phenyl | —NHCOCH$_3$ | 4-acetoxybenzyl | 2-naphthylmethyl | methyl |
| 534 | 4-chlorophenyl | —NHCOCH$_3$ | 4-acetoxybenzyl | 2-naphthylmethyl | methyl |
| 535 | 4-fluorophenyl | —NHCOCH$_3$ | 4-acetoxybenzyl | 2-naphthylmethyl | methyl |
| 536 | 3,4-difluorophenyl | —NHCOCH$_3$ | 4-acetoxybenzyl | 2-naphthylmethyl | methyl |

The following is an outline of a synthetic pathway for preparing analogs 481–536, however, other embodiments of the 3-ketopiperazine scaffold, for example, $R^{17}$ equal to ethyl, propyl, and the like can be prepared by using modification to this general scheme.

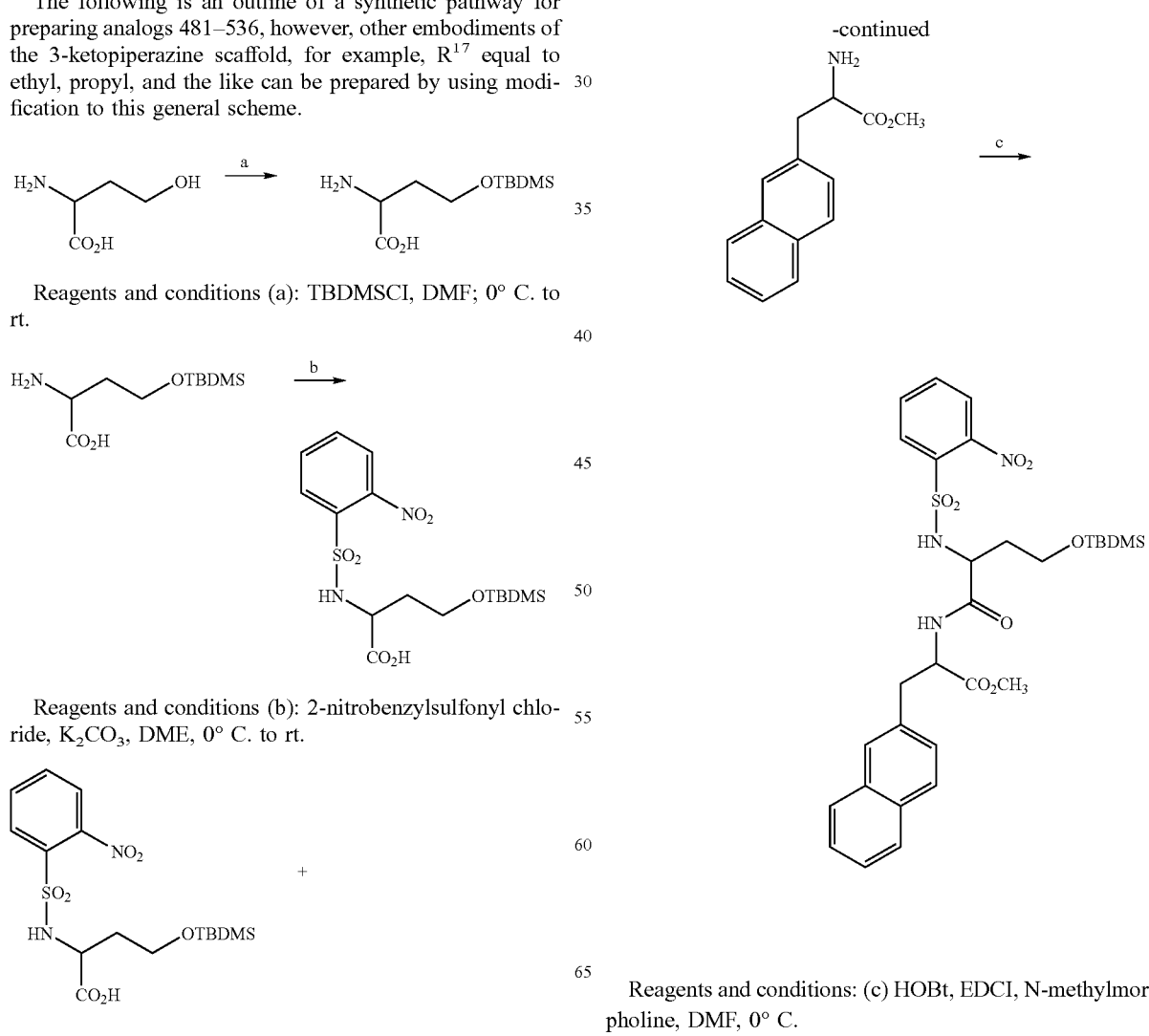

Reagents and conditions (a): TBDMSCI, DMF; 0° C. to rt.

Reagents and conditions (b): 2-nitrobenzylsulfonyl chloride, K$_2$CO$_3$, DME, 0° C. to rt.

Reagents and conditions: (c) HOBt, EDCI, N-methylmorpholine, DMF, 0° C.

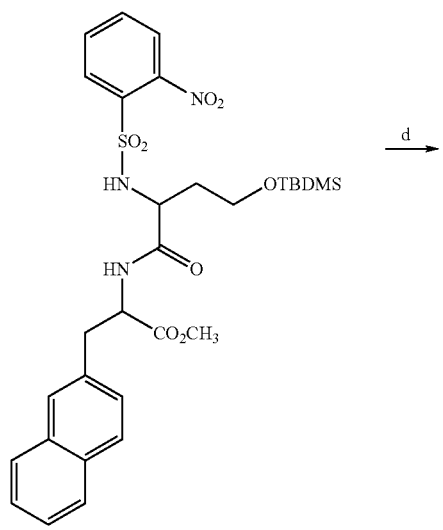
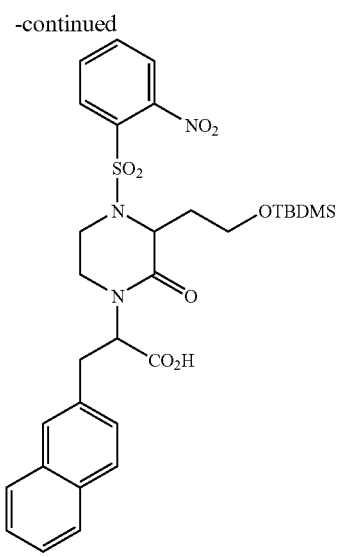
-continued
Reagents and conditions: (e) LiOH, 0° C.
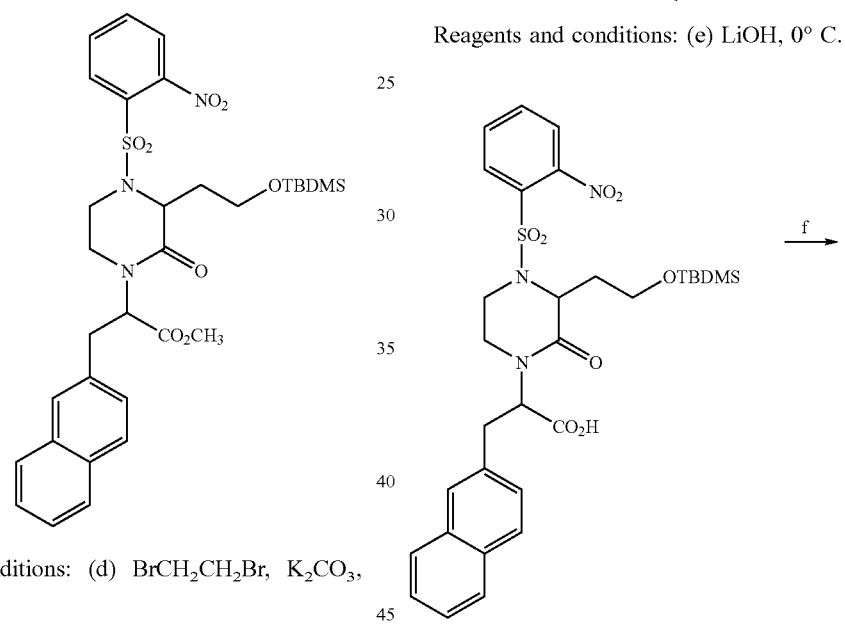
Reagents and conditions: (d) BrCH$_2$CH$_2$Br, K$_2$CO$_3$, DMF; 55° C.
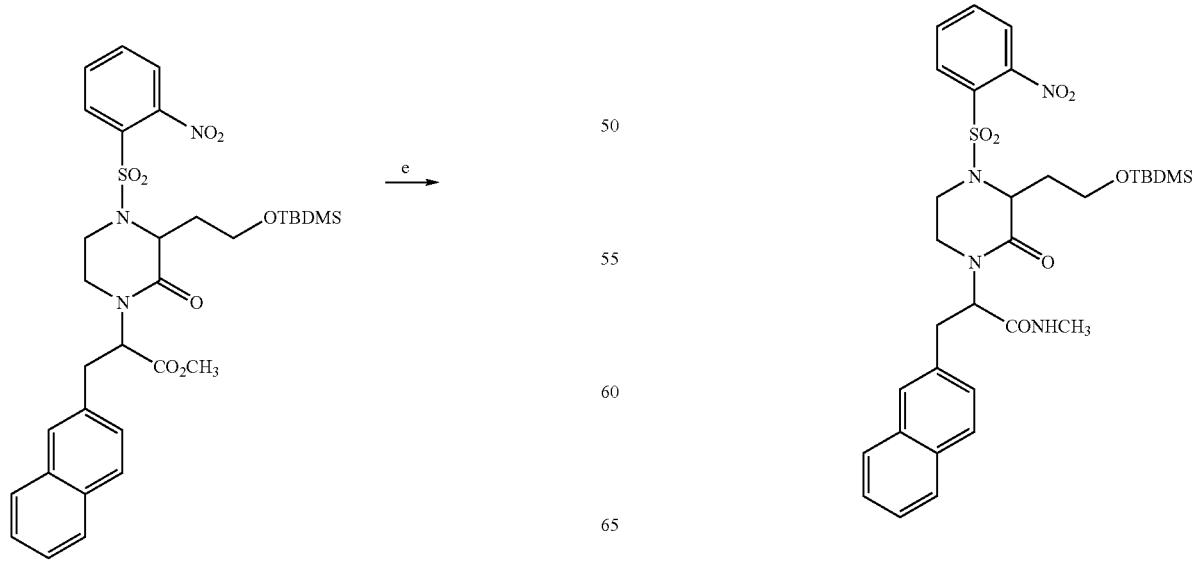
Reagents and conditions: (f) NH$_2$CH$_3$, PyBOP, rt.

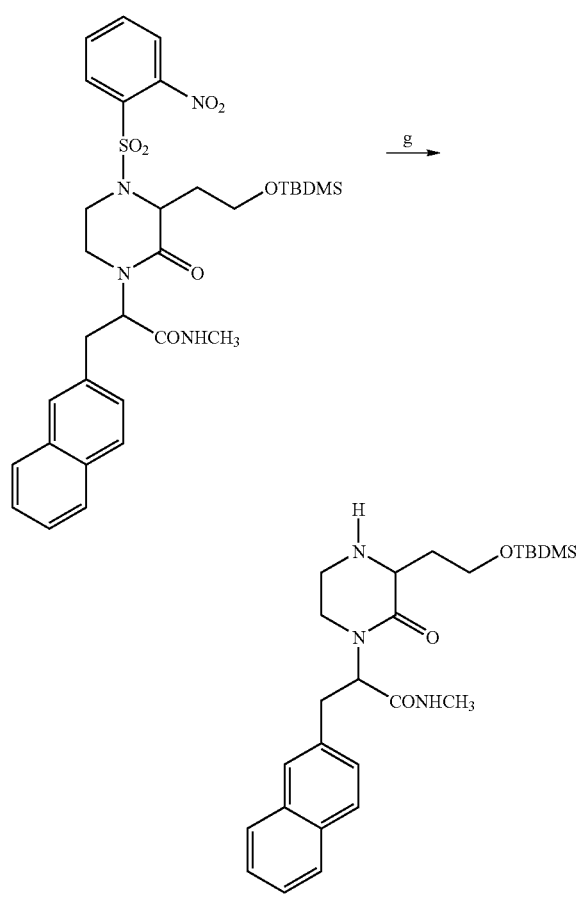
Reagents and conditions: (g) p-thiophenol, K$_2$CO$_3$, acetonitrile; rt.
Reagents and conditions: (h) (Boc)$_2$O, TEA, DCM, rt.
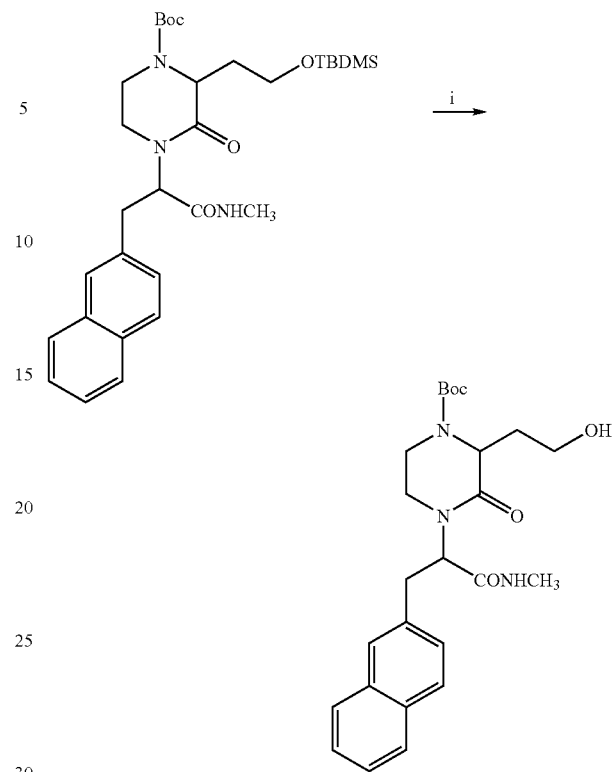
Reagents and conditions: (i) tetrabutylammonium fluoride, water, rt.
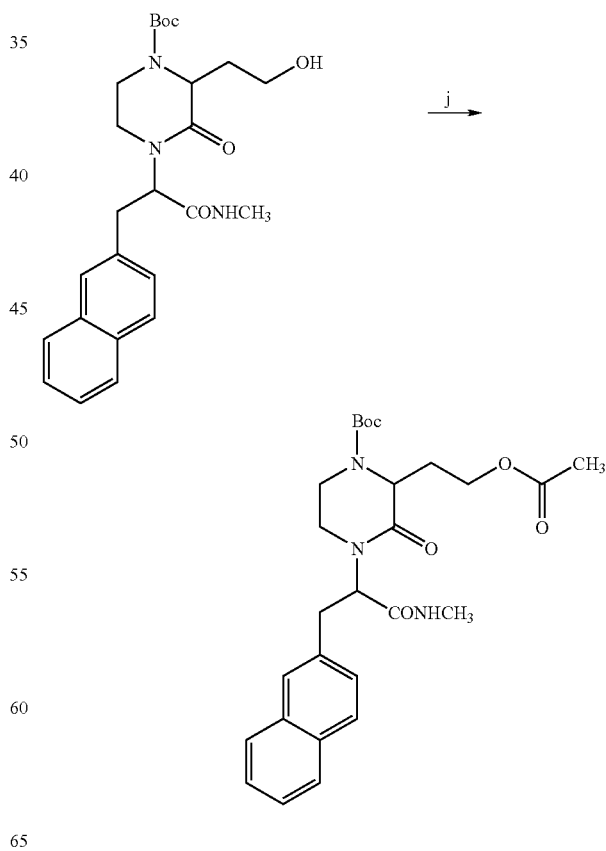
Reagents and conditions: (j) Ac$_2$O, pyridine, DMAP, DCM, rt.

101
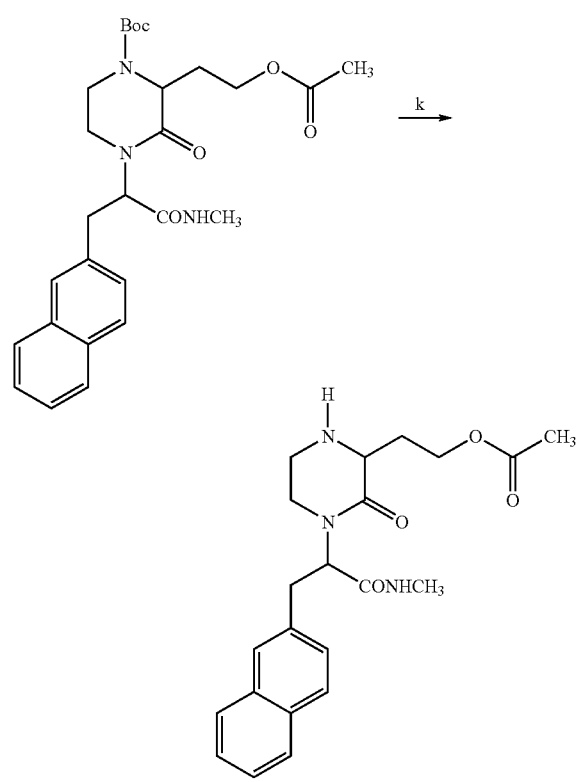
Reagents and conditions: (k) TFA, DCM, rt.
102
Reagents and conditions: (l) HOBt, EDCI, N-methylmorpholine, DMF, 0° C.
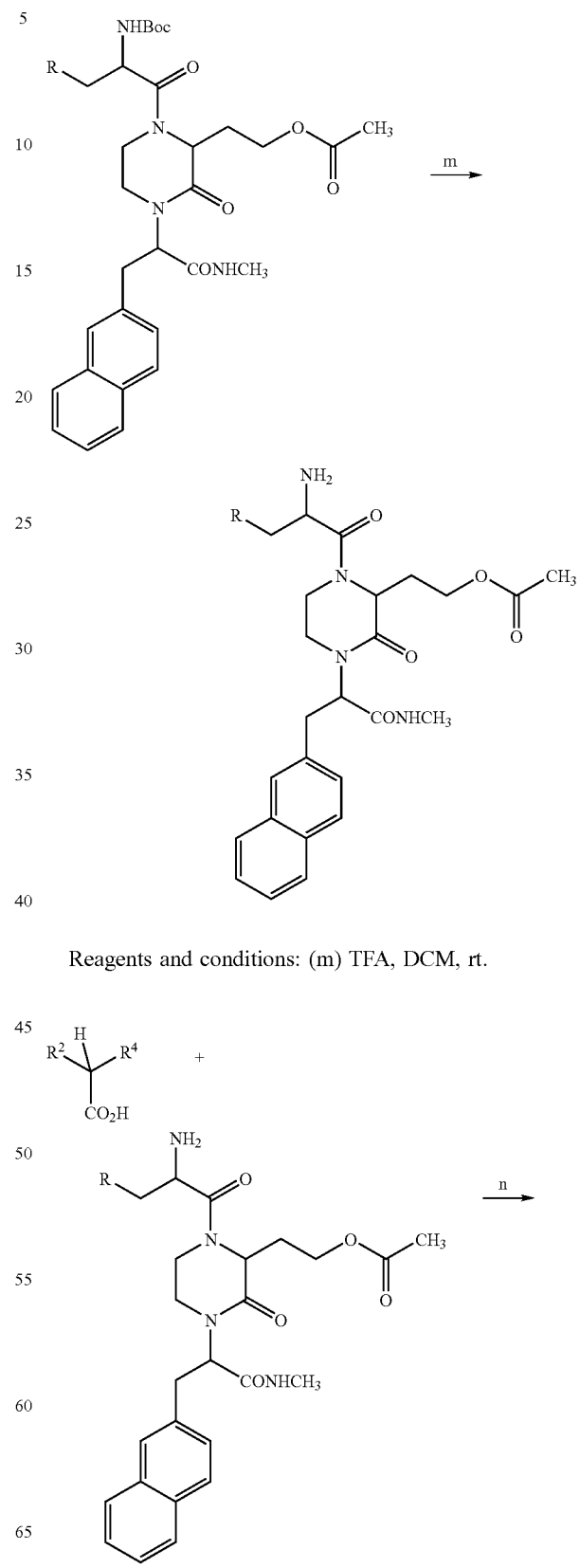
Reagents and conditions: (m) TFA, DCM, rt.

-continued

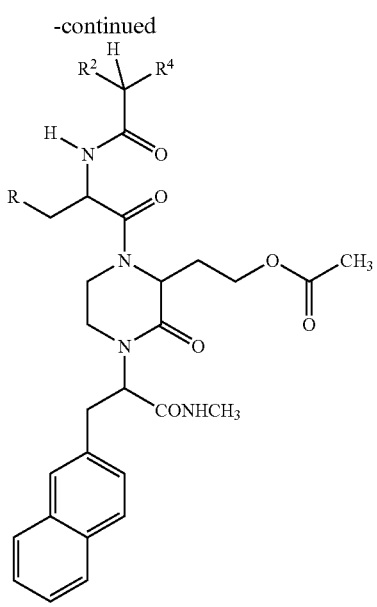

Reagents and conditions: (n) HOBt, EDCI, N-methylmorpholine, DMF, 0° C.

Preparation of 3-Ketopiperazine Intermediate

The following is a procedure for preparing the 3-ketopiperazine intermediate having the formula:

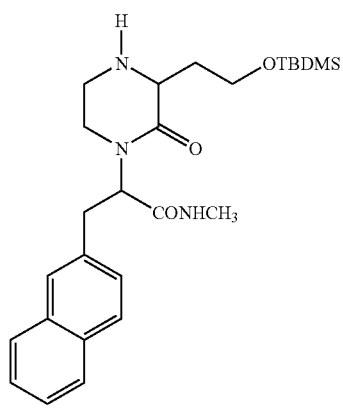

2-{3-[2-(tert-Butyldimethylsilanyloxy)ethyl]-2-oxo-piperizin-1-yl}-N-methyl-3-naphthalen-2-yl-propionamide (58)

Preparation of 2-amino-4-(tert-butyldimethylsilanyloxy) butyric acid (52): Imidazole (20.4 g, 300 mmol) is added to a solution of homoserine (11.9 g, 100 mmol) in DMF (100 mL) and the solution is stirred 15 minutes then cooled to 0° C. tert-Butyldimethylsilyl chloride (13.7 g, 91 mmol) added and the mixture is stirred for ten minutes at 0° C. the for 4 hours at room temperature. The reaction mixture is poured into water (3 L) and the resulting solid is collected by filtration. The isolated product is dried and used without further purification.

Preparation of 4-(tert-butyldimethylsilanyloxy)-2-(2-nitrobenzenesulfonylamino) butyric acid (53): 2-Amino-4-(tert-butyldimethylsilanyloxy)butyric acid, 52, (23.3 g, 10 mmol) is dissolved in a mixture of 1,2-dimethoxyethane (800 mL), water (800 mL) and $K_2CO_3$ (20.7 g, 150 mmol) and the resulting solution is cooled to 0° C. After 15 minutes, 2-nitrobenzylsulfonyl chloride (26.6 g, 120 mmol) is added, the cooling bath removed, and the mixture is stirred for 18 hours. The reaction mixture is acidified with 1N HCl to a pH of from 3 to 4 and the solution extracted several times with EtOAc. The combined organic layers are dried and concentrated in vacuo and the crude product is purified over silica gel to afford 19.3 g (46%) of the desired product.

Preparation of 2-[4-(tert-butyldimethylsilanyloxy)-2-(2-nitrobenzenesulfoylamino)-butyrylamino]-3-naphthalen-2-yl propionic acid methyl ester (54): A solution of 4-(tert-butyldimethylsilanyloxy)-2-(2-nitrobenzenesulfonylamino) butyric acid, 53, (41.9 g, 100 mmol), 2-amino-3-naphthalen-2-yl propionic acid methyl ester (41.9 g, 100 mmol), 2-amino-3-naphthalen-2-yl propionic acid methyl ester (22.9 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminoopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to give the crude product which is purified over silica gel to afford 34.7 g (55%).

Preparation of 2-[3-[2-(tert-butyldimethylsilanyloxy) ethyl]-4-(2-nitrobenzenesulfonyl)-2-oxo-piperizin-1-yl]-3-naphtalen-2-yl propionic acid methyl ester (55): A mixture of 2-[4-(tert-butyldimethylsilanyloxy)-2-(2-nitrobenzenesulfoylamino)-butyrylamino]-3-naphthalen-2-yl propionic acid methyl ester, 54, (63 g, 100 mmol), 1,2-dibromoethane (10.3 mL, 120 mmol), potassium carbonate (138 g, 1 mol) in DMF (500 ml) is stirred at 55° C. for 18 hours. The reaction mixture is cooled to room temperature, treated with 1 M $KHSO_4$ and the resulting solution is extracted with ethyl acetate. The crude product is purified over silica (sequential elution with EtOAc/hexanes mixtures 1:2, 1:1, 100% EtOAc, then EtOAc with 5% MeOH) to afford 50.8 g (77%) of the desired product.

Preparation of 2-[3-[2-tert-butyldimethylsilanyloxy) ethyl]-4-(2-nitrobenzenesulfonyl)-2-oxo-pipperazin-1-yl]-3-naphthalen-2-yl propionic acid (56): A mixture 2-[3-[2-(tert-butyldimethylsilanyloxy)ethyl]-4-(2-nitrobenzenesulfonyl)-2-oxo-piperizin-1-yl]-3-naphtalen-2-yl propionic acid methyl ester, 55, (65.6 g, 100 mmol) in THF (1000 mL) is cooled in an ice-bath and treated with a solution of LiOH (21 g, 500 mmol) in water (750 mL). The solution is stirred for 1 hour at 0° C. then allowed to warm to room temperature and stir an additional 3 hours. The reaction is then diluted with water (3 L), cooled in an ice-bath and acidified with 1 M HCl to pH 3–4. The resulting solution is extracted with EtOAc. The organic phase is dried and concentrated in vacuo to afford 48.2 g (75%) of the desired product.

Preparation of 2-[3-[2-(tert-butyldimethylsilanyloxy) ethyl]-4-(2-nitrobenzene-sulfonyl)-2-oxo-piperazin-1-yl]-N-methyl-3-naphthalen-2-yl propionamide (57): To a mixture of 2-[3-[2-tert-butyldimethylsilanyloxy)ethyl]-4-(2-nitrobenzenesulfonyl)-2-oxo-pipperazin-1-yl]-3-naphthalen-2-yl propionic acid, 56, (6.4 g, 10 mmol), 2 M methylamine (40 ml) in DMF (200 mL) is added benzotriazole-1-yl-oxy-tris-pyrrolidinol-phosphonium hexafluorophosphate (PyBOP) (7.8 g, 15 mmol). The solution is stirred for 18 hours then diluted with water (500 mL) and the solution extracted with EtOAc. The organic phase is dried, concentrated in vacuo and the resulting crude product is purified over silica gel (EtOAc/hexanes 1:3, followed by 1:1 and 10% methanol in EtOAc) to afford the desired product.

Preparation of 2-{3-[2-(tert-Butyldimethylsilanyloxy) ethyl]-2-oxo-piperizin-1-yl}-N-methyl-3-naphthalen-2-yl-propionamide (58): 2-[3-[2-(tert-butyldimethylsilanyloxy) ethyl]-4-(2-nitrobenzene-sulfonyl)-2-oxo-piperazin-1-yl]-N-methyl-3-naphthalen-2-yl propionamide, 57, (6.5 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

EXAMPLE 9

Acetic acid 2-[1-{2-[2-acetylamino-3-(hydroxyphenyl)propionylamino]-3-(4-fluorophenyl)propionyl}-4-(1-methylcarbamoyl-2-naphthalen-2-ylethyl)-piperazin-2-yl]ethyl ester Preparation of 2-[2-(tert-butyldimethylsilanyloxy)ethyl]-4-(1-methylcarbamoyl-2-naphthalen-2-ylethyl)-piperazine-1-carboxylic acid tert-butyl ester (59): Di-tert-butyl dicarbonate (26.2 g, 120 mmol) is added to a stirred solution of 2-{3-[2-(tert-butyldimethylsilanyloxy)ethyl]-2-oxo-piperizin-1-yl}-N-methyl-3-naphthalen-2-yl-propionamide, 58, (45.5 g, 100 mol) and triethylamine (32 mL, 230 mmol) dissolved in dichloromethane (150 mL) at 0° C. The resulting solution is allowed to warm to room temperature and stirred for 4 hours. The solution is then diluted with dichloromethane (100 mL), washed twice with 1 N HCl and twice with aq. NaHCO₃ solution. The organic layer is then dried over Na₂SO₄, filtered and concentrated in vacuo to give the desired product which is sufficiently pure for use without purification.

Preparation of 2-(2-hydroxyethyl)-4-(1-methylcarbamoyl-2-naphthalen-2-ylethyl)piperazine-1-carboxylic acid tert-butyl ester (60): A solution of 2-[2-(tert-butyldimethylsilanyloxy)ethyl]-4-(1-methylcarbamoyl-2-naphthalen-2-ylethyl)-piperazine-1-carboxylic acid tert-butyl ester, 59, (15.9 g, 23.5 mmol) and 1 M tetrabutylammonium fluoride (40 mL) is stirred for 24 hours. The reaction solution is filtered through a pad of silica gel, the filtrate is concentrated in vacuo, and the resulting crude product purified over silica gel (EtOAc/hexane 1:2, 1:1, then 5% methanol in EtOAc) to afford the desired product.

Preparation of 2-(2-acetoxyethyl)-4-(1-methylcarbamoyl-2-naphthalen-2-ylethyl)-piperazine-1-carboxylic acid tert-butyl ester (61): A solution of 2-(2-hydroxyethyl)-4-(1-methylcarbamoyl-2-naphthalen-2-ylethyl)piperazine-1-carboxylic acid tert-butyl ester, 60, (4.4 g, 10 mmol), acetic anhydride (13 mL), pyridine (1 mL) and N,N-dimethylaminopyridine (0.25 g) in dichloromethane (50 mL) is stirred for 1.5 hours. The solution is then extracted with water and 1 n HCl. The organic phase is dried, concentrated in vacuo, and the resulting crude product purified over silica gel (EtOAc/hexane 1:3 then 1:1) to afford the desired product.

Preparation of acetic acid 2-[4-(1-methylcarbamoyl-2-naphthalen-2-ylethyl-piperazin-2-yl]ethyl ester (62): 2-(2-acetoxyethyl)-4-(1-methylcarbamoyl-2-naphthalen-2-yl-ethyl)-piperazine-1-carboxylic acid tert-butyl ester, 61, (4.8 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Preparation of acetic acid 2-[1-(2-N-Boc-amino-3-(4-fluorophenyl)propionyl)-4-(1-methylcarbamoyl-2-naphthalen-2-ylethyl)piperazin-2-yl]-ethyl ester (63): A solution of acetic acid 2-[4-(1-methylcarbamoyl-2-naphthalen-2-yl-ethyl-piperazin-2-yl] ethyl ester, 62, (38.3 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which purified over silica gel.

Preparation of acetic acid 2-{1-[2-amino-3-(4-fluorophenyl)propionyl]-4-(1-methylcarbamoyl-2-naphthalen-2-yl-ethyl)piperazin-2-yl}-ethyl ester (64): (6.3 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Preparation of acetic acid 2-[1-{2-[2-acetylamino-3-(hydroxyphenyl)propionyl-amino]-3-(4-fluorophenyl)propionyl}-4-(1-methylcarbamoyl-2-naphthalen-2-ylethyl)-piperazin-2-yl]ethyl ester (65): A solution of acetic acid 2-{1-[2-amino-3-(4-fluorophenyl)propionyl]-4-(1-methylcarbamoyl-2-naphthalen-2-ylethyl)piperazin-2-yl}-ethyl ester, 64, (54.9 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which purified over silica gel.

Another iteration of this category and an iteration of the aspect of the invention, which relates to Y units wherein $R^{15}$ comprises —NH₂ or —OH, encompasses receptor ligands having the formula:

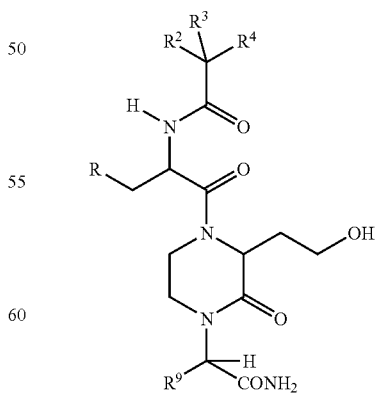

wherein R, $R^2$, $R^3$, $R^4$, and $R^9$ are defined in Table X herein below.

TABLE X

| No. | R | $R^2$ | $R^3$ | $R^4$ | $R^9$ |
|---|---|---|---|---|---|
| 537 | phenyl | —NHC(O)CH$_3$ | H | benzyl | phenyl |
| 538 | benzyl | —NHC(O)CH$_3$ | H | benzyl | phenyl |
| 539 | 3-fluorophenyl | —NHC(O)CH$_3$ | H | benzyl | phenyl |
| 540 | 4-fluorophenyl | —NHC(O)CH$_3$ | H | benzyl | phenyl |
| 541 | 3,5-difluorophenyl | —NHC(O)CH$_3$ | H | benzyl | phenyl |
| 542 | 4-chlorophenyl | —NHC(O)CH$_3$ | H | benzyl | phenyl |
| 543 | 4-hydroxyphenyl | —NHC(O)CH$_3$ | H | benzyl | phenyl |
| 544 | phenyl | —NHC(O)CH$_3$ | H | 4-imidazolylmethyl | phenyl |
| 545 | benzyl | —NHC(O)CH$_3$ | H | 4-imidazolylmethyl | phenyl |
| 546 | 3-fluorophenyl | —NHC(O)CH$_3$ | H | 4-imidazolylmethyl | phenyl |
| 547 | 4-fluorophenyl | —NHC(O)CH$_3$ | H | 4-imidazolylmethyl | phenyl |
| 548 | 3,5-difluorophenyl | —NHC(O)CH$_3$ | H | 4-imidazolylmethyl | phenyl |
| 549 | 4-chlorophenyl | —NHC(O)CH$_3$ | H | 4-imidazolylmethyl | phenyl |
| 550 | 4-hydroxyphenyl | —NHC(O)CH$_3$ | H | 4-imidazolylmethyl | phenyl |
| 551 | phenyl | —NHC(O)CH$_3$ | H | 4-chlorobenzyl | phenyl |
| 552 | benzyl | —NHC(O)CH$_3$ | H | 4-chlorobenzyl | phenyl |
| 553 | 3-fluorophenyl | —NHC(O)CH$_3$ | H | 4-chlorobenzyl | phenyl |
| 554 | 4-fluorophenyl | —NHC(O)CH$_3$ | H | 4-chlorobenzyl | phenyl |
| 555 | 3,5-difluorophenyl | —NHC(O)CH$_3$ | H | 4-chlorobenzyl | phenyl |
| 556 | 4-chlorophenyl | —NHC(O)CH$_3$ | H | 4-chlorobenzyl | phenyl |
| 557 | 4-hydroxyphenyl | —NHC(O)CH$_3$ | H | 4-chlorobenzyl | phenyl |
| 558 | phenyl | —NHC(O)CH$_3$ | H | 4-hydroxybenzyl | phenyl |
| 559 | benzyl | —NHC(O)CH$_3$ | H | 4-hydroxybenzyl | phenyl |
| 560 | 3-fluorophenyl | —NHC(O)CH$_3$ | H | 4-hydroxybenzyl | phenyl |
| 561 | 4-fluorophenyl | —NHC(O)CH$_3$ | H | 4-hydroxybenzyl | phenyl |
| 562 | 3,5-difluorophenyl | —NHC(O)CH$_3$ | H | 4-hydroxybenzyl | phenyl |
| 563 | 4-chlorophenyl | —NHC(O)CH$_3$ | H | 4-hydroxybenzyl | phenyl |
| 564 | 4-hydroxyphenyl | —NHC(O)CH$_3$ | H | 4-hydroxybenzyl | phenyl |
| 565 | phenyl | —NHC(O)CH$_3$ | H | benzyl | 2-naphthyl |
| 566 | benzyl | —NHC(O)CH$_3$ | H | benzyl | 2-naphthyl |
| 567 | 3-fluorophenyl | —NHC(O)CH$_3$ | H | benzyl | 2-naphthyl |
| 568 | 4-fluorophenyl | —NHC(O)CH$_3$ | H | benzyl | 2-naphthyl |
| 569 | 3,5-difluorophenyl | —NHC(O)CH$_3$ | H | benzyl | 2-naphthyl |
| 570 | 4-chlorophenyl | —NHC(O)CH$_3$ | H | benzyl | 2-naphthyl |
| 571 | 4-hydroxyphenyl | —NHC(O)CH$_3$ | H | benzyl | 2-naphthyl |
| 572 | phenyl | —NHC(O)CH$_3$ | H | 4-imidazolylmethyl | 2-naphthyl |
| 573 | benzyl | —NHC(O)CH$_3$ | H | 4-imidazolylmethyl | 2-naphthyl |
| 574 | 3-fluorophenyl | —NHC(O)CH$_3$ | H | 4-imidazolylmethyl | 2-naphthyl |
| 575 | 4-fluorophenyl | —NHC(O)CH$_3$ | H | 4-imidazolylmethyl | 2-naphthyl |
| 576 | 3,5-difluorophenyl | —NHC(O)CH$_3$ | H | 4-imidazolylmethyl | 2-naphthyl |
| 577 | 4-chlorophenyl | —NHC(O)CH$_3$ | H | 4-imidazolylmethyl | 2-naphthyl |
| 578 | 4-hydroxyphenyl | —NHC(O)CH$_3$ | H | 4-imidazolylmethyl | 2-naphthyl |
| 579 | phenyl | —NHC(O)CH$_3$ | H | 4-chlorobenzyl | 2-naphthyl |
| 580 | benzyl | —NHC(O)CH$_3$ | H | 4-chlorobenzyl | 2-naphthyl |
| 581 | 3-fluorophenyl | —NHC(O)CH$_3$ | H | 4-chlorobenzyl | 2-naphthyl |
| 582 | 4-fluorophenyl | —NHC(O)CH$_3$ | H | 4-chlorobenzyl | 2-naphthyl |
| 583 | 3,5-difluorophenyl | —NHC(O)CH$_3$ | H | 4-chlorobenzyl | 2-naphthyl |
| 584 | 4-chlorophenyl | —NHC(O)CH$_3$ | H | 4-chlorobenzyl | 2-naphthyl |
| 585 | 4-hydroxyphenyl | —NHC(O)CH$_3$ | H | 4-chlorobenzyl | 2-naphthyl |
| 586 | phenyl | —NHC(O)CH$_3$ | H | 4-hydroxybenzyl | 2-naphthyl |
| 587 | benzyl | —NHC(O)CH$_3$ | H | 4-hydroxybenzyl | 2-naphthyl |
| 588 | 3-fluorophenyl | —NHC(O)CH$_3$ | H | 4-hydroxybenzyl | 2-naphthyl |
| 589 | 4-fluorophenyl | —NHC(O)CH$_3$ | H | 4-hydroxybenzyl | 2-naphthyl |
| 590 | 3,5-difluorophenyl | —NHC(O)CH$_3$ | H | 4-hydroxybenzyl | 2-naphthyl |
| 591 | 4-chlorophenyl | —NHC(O)CH$_3$ | H | 4-hydroxybenzyl | 2-naphthyl |
| 592 | 4-hydroxyphenyl | —NHC(O)CH$_3$ | H | 4-hydroxybenzyl | 2-naphthyl |
| 593 | 4-fluorophenyl | H | H | benzyl | 2-naphthyl |
| 594 | phenyl | H | H | benzyl | 2-naphthyl |
| 595 | 4-fluorophenyl | H | H | 4-hydroxybenzyl | 2-naphthyl |
| 596 | phenyl | —NHC(O)CH$_3$ | H | 2-naphthylmethyl | 2-naphthyl |

The following is an outline of a synthetic pathway for preparing analogs 537–596, however, other embodiments of this 3-ketopiperazine scaffold, for example, 3-hydroxypropyl analogs, and the like can be prepared by using modification to this general scheme.

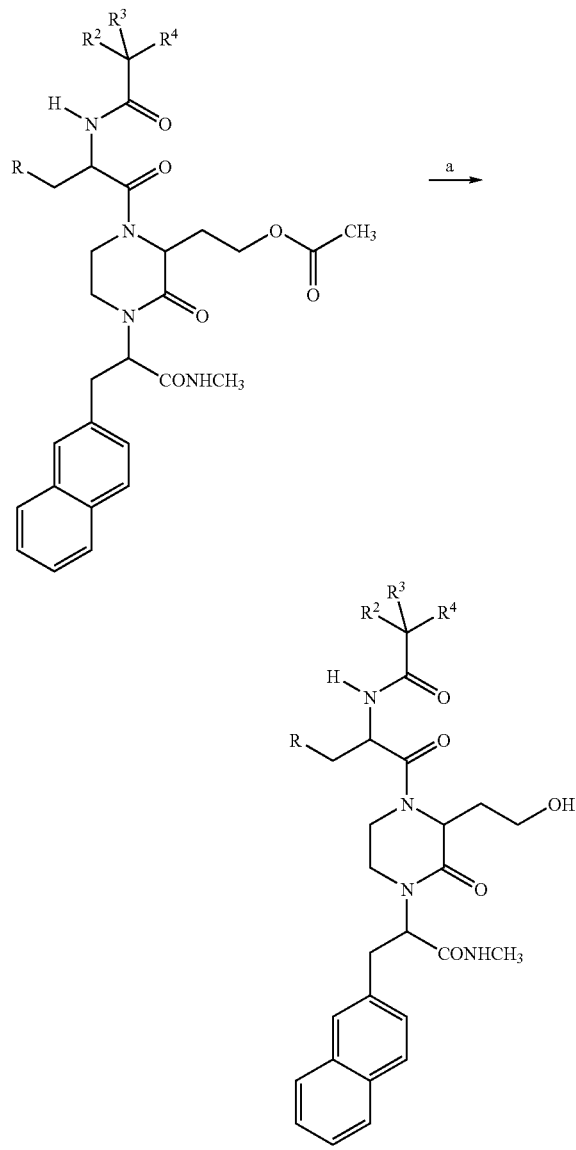

Reagents and conditions: (a) NaOCH$_3$/CH$_3$OH

EXAMPLE 10

Preparation of 2-[4-[2-[2-acetylamino-3-(4-hydroxyphenyl)propionylamino]-3-(4-fluorophenyl)propionyl]-3-(2-hydroxyethyl)piperazin-1-yl]-N-methyl-3-naphthalene-2-yl-propionamide (66): To a solution acetic acid 2-[1-{2-[2-acetylamino-3-(hydroxyphenyl)propionylamino]-3-(4-fluorophenyl)propionyl}-4-(1-methylcarbamoyl-2-naphthalen-2-ylethyl)piperazin-2-yl]ethyl ester, 65, (7.5 g, 10 mmol) in methanol (50 mL) is added freshly prepared NaOCH$_3$ (0.55 g, 10.1 mmol) and the solution stirred overnight. The solution is concentrated in vacuo, the resulting residue partitioned between dichloromethane and water, the organic layer is dried and concentrated in vacuo to afford the desired product.

Another category of receptor ligand analogs according to the present invention relates to 2,5-substituted 3-ketopiperazines comprising the conformationally restricted ring scaffold having the formula:

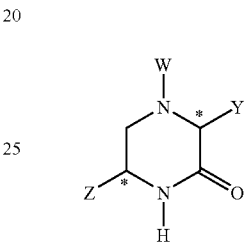

wherein the carbon atoms indicated with an asterisk can have any configuration. Table X relates to non-limiting examples of one aspect of analogs in this category, said analogs having the formula:

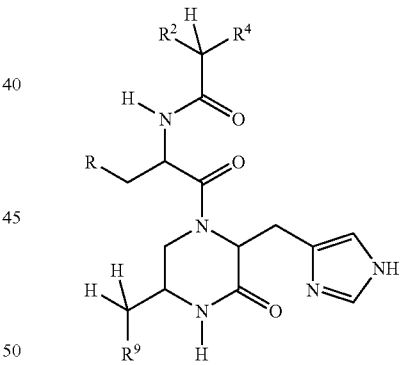

wherein R, R$^2$, R$^4$, and R$^9$ are defined in Table X.

TABLE XI

| No. | R | R$^2$ | R$^3$ | R$^4$ | R$^9$ |
|---|---|---|---|---|---|
| 597 | phenyl | —NHC(O)CH$_3$ | H | benzyl | phenyl |
| 598 | benzyl | —NHC(O)CH$_3$ | H | benzyl | phenyl |
| 599 | 3-fluorophenyl | —NHC(O)CH$_3$ | H | benzyl | phenyl |
| 600 | 4-fluorophenyl | —NHC(O)CH$_3$ | H | benzyl | phenyl |
| 601 | 3,5-difluorophenyl | —NHC(O)CH$_3$ | H | benzyl | phenyl |
| 602 | 4-chlorophenyl | —NHC(O)CH$_3$ | H | benzyl | phenyl |
| 603 | 4-hydroxyphenyl | —NHC(O)CH$_3$ | H | benzyl | phenyl |
| 604 | phenyl | —NHC(O)CH$_3$ | H | 4-imidazolylmethyl | phenyl |

TABLE XI-continued

| No. | R | R² | R³ | R⁴ | R⁹ |
|---|---|---|---|---|---|
| 605 | benzyl | —NHC(O)CH₃ | H | 4-imidazolylmethyl | phenyl |
| 606 | 3-fluorophenyl | —NHC(O)CH₃ | H | 4-imidazolylmethyl | phenyl |
| 607 | 4-fluorophenyl | —NHC(O)CH₃ | H | 4-imidazolylmethyl | phenyl |
| 608 | 3,5-difluorophenyl | —NHC(O)CH₃ | H | 4-imidazolylmethyl | phenyl |
| 609 | 4-chlorophenyl | —NHC(O)CH₃ | H | 4-imidazolylmethyl | phenyl |
| 610 | 4-hydroxyphenyl | —NHC(O)CH₃ | H | 4-imidazolylmethyl | phenyl |
| 611 | phenyl | —NHC(O)CH₃ | H | 4-chlorobenzyl | phenyl |
| 612 | benzyl | —NHC(O)CH₃ | H | 4-chlorobenzyl | phenyl |
| 613 | 3-fluorophenyl | —NHC(O)CH₃ | H | 4-chlorobenzyl | phenyl |
| 614 | 4-fluorophenyl | —NHC(O)CH₃ | H | 4-chlorobenzyl | phenyl |
| 615 | 3,5-difluorophenyl | —NHC(O)CH₃ | H | 4-chlorobenzyl | phenyl |
| 616 | 4-chlorophenyl | —NHC(O)CH₃ | H | 4-chlorobenzyl | phenyl |
| 617 | 4-hydroxyphenyl | —NHC(O)CH₃ | H | 4-chlorobenzyl | phenyl |
| 618 | phenyl | —NHC(O)CH₃ | H | 4-hydroxybenzyl | phenyl |
| 619 | benzyl | —NHC(O)CH₃ | H | 4-hydroxybenzyl | phenyl |
| 620 | 3-fluorophenyl | —NHC(O)CH₃ | H | 4-hydroxybenzyl | phenyl |
| 621 | 4-fluorophenyl | —NHC(O)CH₃ | H | 4-hydroxybenzyl | phenyl |
| 622 | 3,5-difluorophenyl | —NHC(O)CH₃ | H | 4-hydroxybenzyl | phenyl |
| 623 | 4-chlorophenyl | —NHC(O)CH₃ | H | 4-hydroxybenzyl | phenyl |
| 624 | 4-hydroxyphenyl | —NHC(O)CH₃ | H | 4-hydroxybenzyl | phenyl |
| 625 | phenyl | —NHC(O)CH₃ | H | benzyl | 2-naphthyl |
| 626 | benzyl | —NHC(O)CH₃ | H | benzyl | 2-naphthyl |
| 627 | 3-fluorophenyl | —NHC(O)CH₃ | H | benzyl | 2-naphthyl |
| 628 | 4-fluorophenyl | —NHC(O)CH₃ | H | benzyl | 2-naphthyl |
| 629 | 3,5-difluorophenyl | —NHC(O)CH₃ | H | benzyl | 2-naphthyl |
| 630 | 4-chlorophenyl | —NHC(O)CH₃ | H | benzyl | 2-naphthyl |
| 631 | 4-hydroxyphenyl | —NHC(O)CH₃ | H | benzyl | 2-naphthyl |
| 632 | phenyl | —NHC(O)CH₃ | H | 4-imidazolylmethyl | 2-naphthyl |
| 633 | benzyl | —NHC(O)CH₃ | H | 4-imidazolylmethyl | 2-naphthyl |
| 634 | 3-fluorophenyl | —NHC(O)CH₃ | H | 4-imidazolylmethyl | 2-naphthyl |
| 635 | 4-fluorophenyl | —NHC(O)CH₃ | H | 4-imidazolylmethyl | 2-naphthyl |
| 636 | 3,5-difluorophenyl | —NHC(O)CH₃ | H | 4-imidazolylmethyl | 2-naphthyl |
| 637 | 4-chlorophenyl | —NHC(O)CH₃ | H | 4-imidazolylmethyl | 2-naphthyl |
| 638 | 4-hydroxyphenyl | —NHC(O)CH₃ | H | 4-imidazolylmethyl | 2-naphthyl |
| 639 | phenyl | —NHC(O)CH₃ | H | 4-chlorobenzyl | 2-naphthyl |
| 640 | benzyl | —NHC(O)CH₃ | H | 4-chlorobenzyl | 2-naphthyl |
| 641 | 3-fluorophenyl | —NHC(O)CH₃ | H | 4-chlorobenzyl | 2-naphthyl |
| 642 | 4-fluorophenyl | —NHC(O)CH₃ | H | 4-chlorobenzyl | 2-naphthyl |
| 643 | 3,5-difluorophenyl | —NHC(O)CH₃ | H | 4-chlorobenzyl | 2-naphthyl |
| 644 | 4-chlorophenyl | —NHC(O)CH₃ | H | 4-chlorobenzyl | 2-naphthyl |
| 645 | 4-hydroxyphenyl | —NHC(O)CH₃ | H | 4-chlorobenzyl | 2-naphthyl |
| 646 | phenyl | —NHC(O)CH₃ | H | 4-hydroxybenzyl | 2-naphthyl |
| 647 | benzyl | —NHC(O)CH₃ | H | 4-hydroxybenzyl | 2-naphthyl |
| 648 | 3-fluorophenyl | —NHC(O)CH₃ | H | 4-hydroxybenzyl | 2-naphthyl |
| 649 | 4-fluorophenyl | —NHC(O)CH₃ | H | 4-hydroxybenzyl | 2-naphthyl |
| 650 | 3,5-difluorophenyl | —NHC(O)CH₃ | H | 4-hydroxybenzyl | 2-naphthyl |
| 651 | 4-chlorophenyl | —NHC(O)CH₃ | H | 4-hydroxybenzyl | 2-naphthyl |
| 652 | 4-hydroxyphenyl | —NHC(O)CH₃ | H | 4-hydroxybenzyl | 2-naphthyl |
| 653 | 4-fluorophenyl | H | H | benzyl | 2-naphthyl |
| 654 | phenyl | H | H | benzyl | 2-naphthyl |
| 655 | 4-fluorophenyl | H | H | 4-hydroxybenzyl | 2-naphthyl |
| 656 | phenyl | —NHC(O)CH₃ | H | 2-naphthylmethyl | 2-naphthyl |

The following is an outline of a synthetic pathway for preparing analogs 597–656, however, other embodiments and iterations of the 3-ketopiperazine scaffold can be prepared using modification to this general procedure.

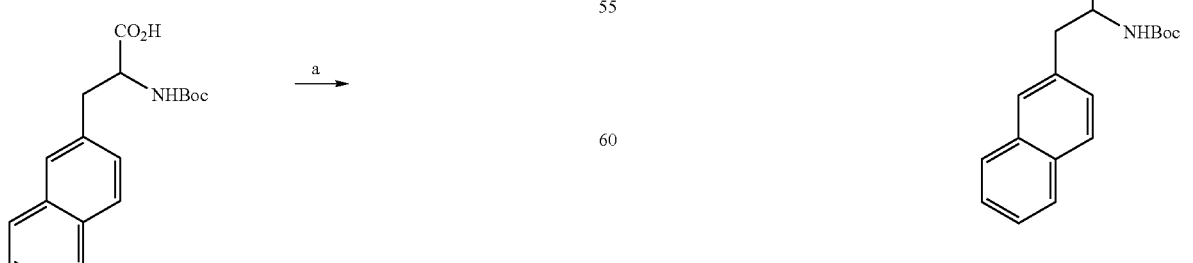

Reagents and conditions: (a) O,N-dimethylhyroxylamine, HOBt, EDCI, N-methylmorpholine, DMF, 0° C.

113
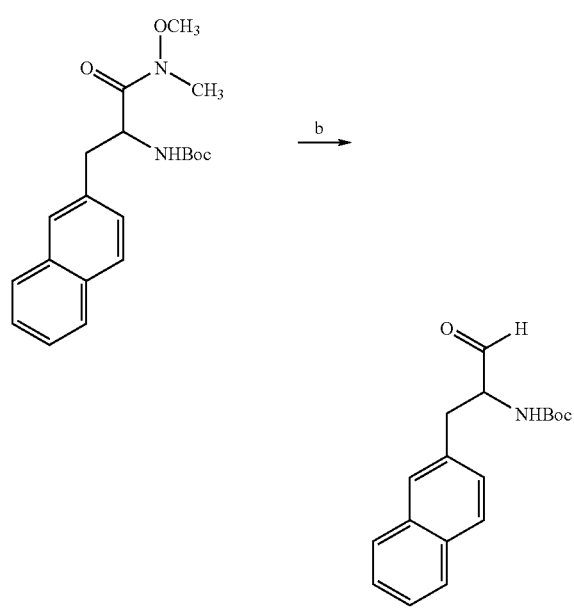
Reagents and conditions: (b) LAH, THF, −60° C.
114
Reagents and conditions: (c) NaBH(OAc)₃, DMF, 0° C. to rt.
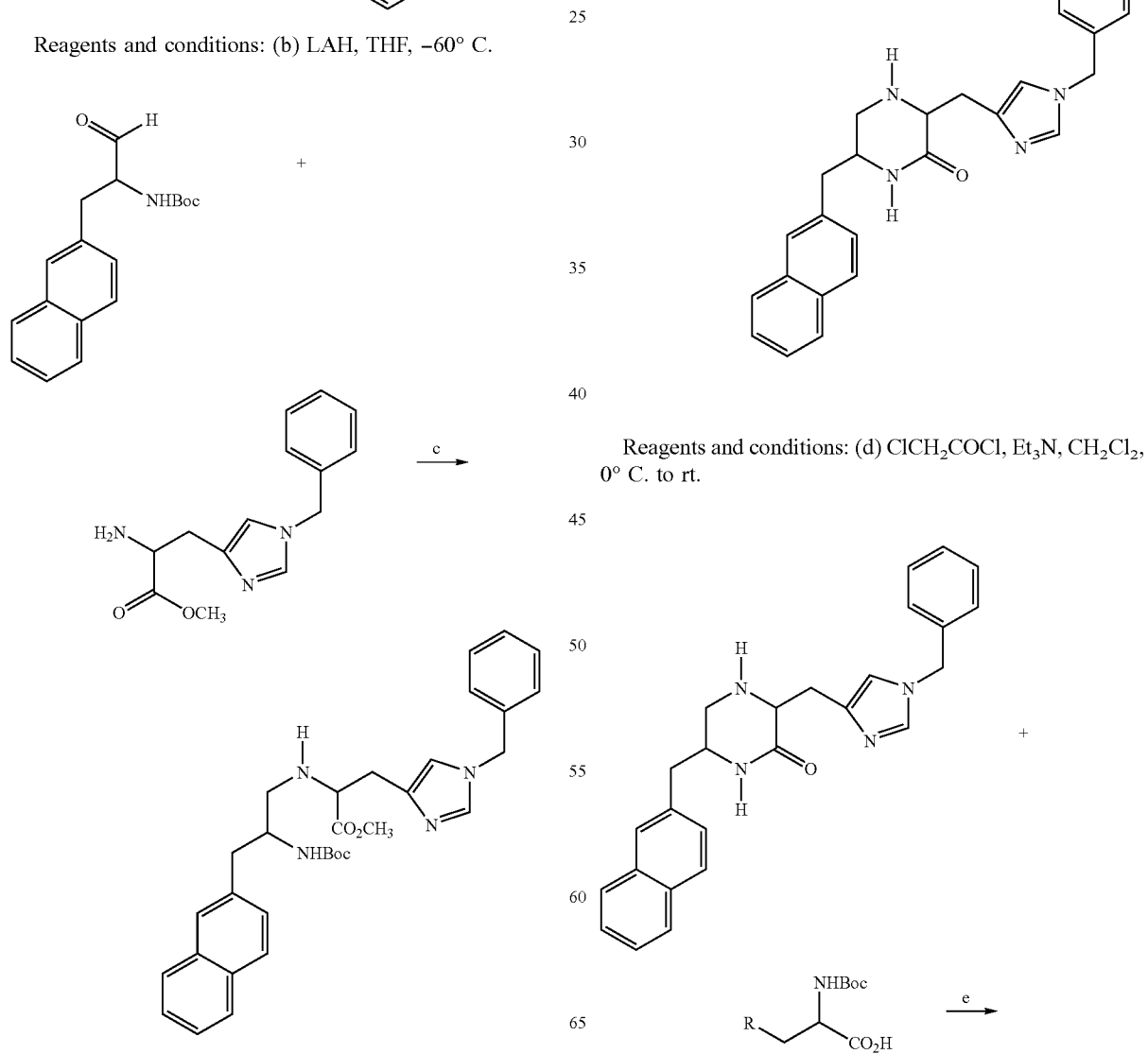
Reagents and conditions: (d) ClCH₂COCl, Et₃N, CH₂Cl₂, 0° C. to rt.

-continued
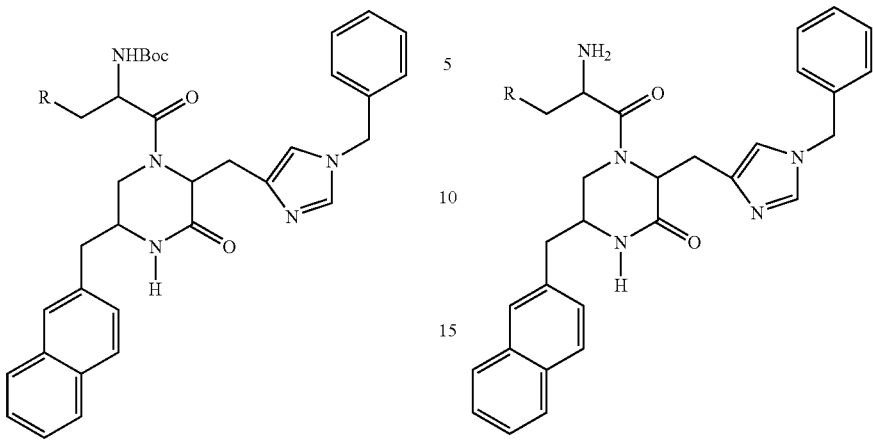
Reagents and conditions: (e) N-Boc-amino acid, EDCI, HOBt, DMF.
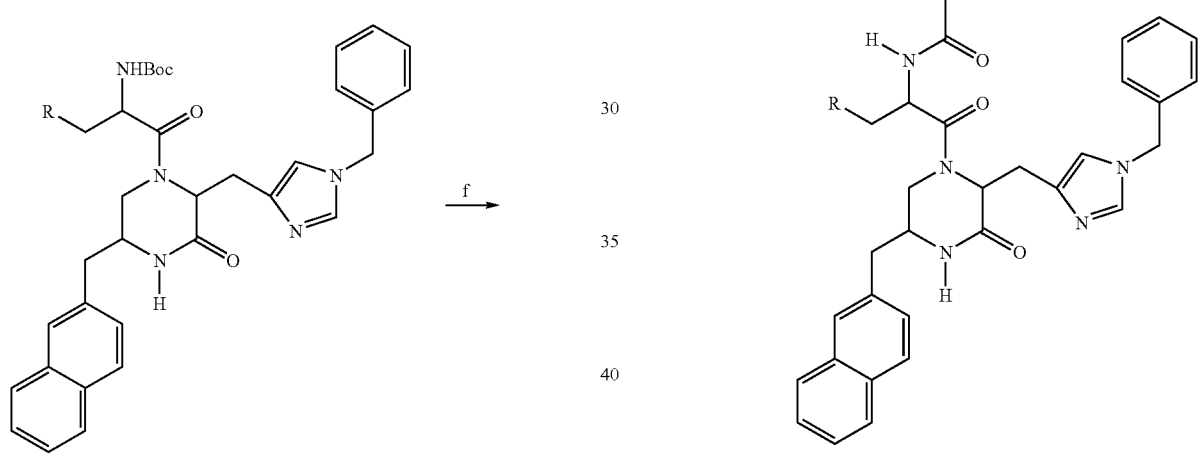
Reagents and conditions: (f) TFA/CH$_2$Cl$_2$, rt.
Reagents and conditions: (g) EDCI, HOBt, DMF.
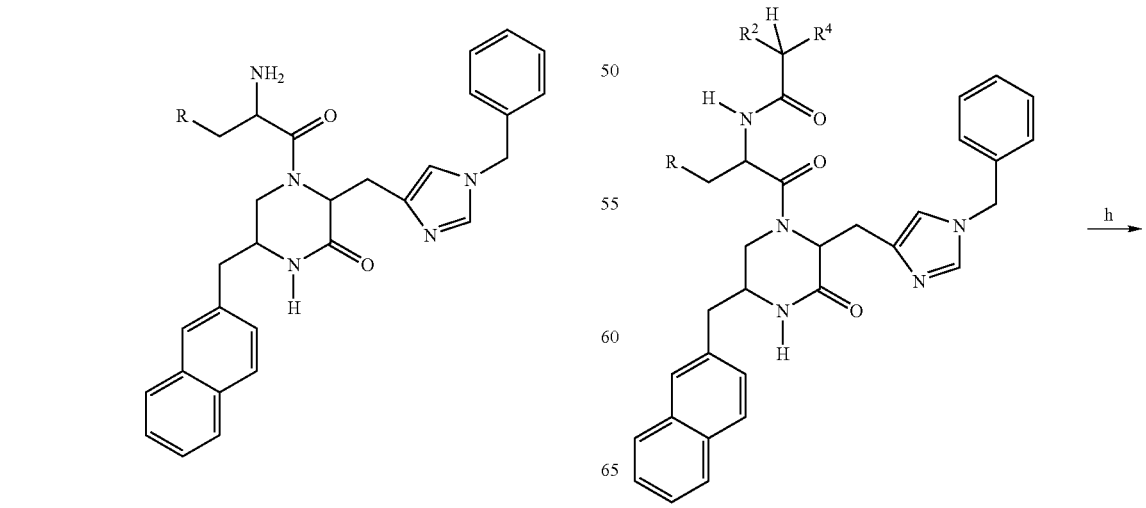

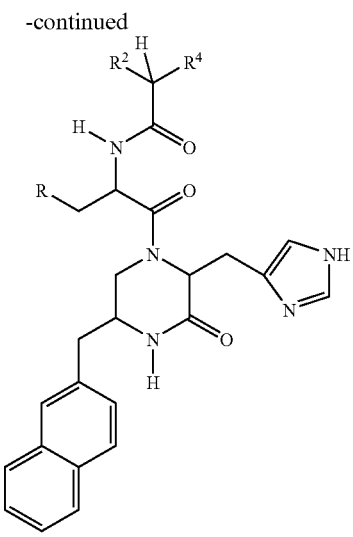

Reagents and conditions: (h) Pd-black, cyclohexene, EtOH/AcOH, reflux.

Preparation of 2,5-Substituted 3-Ketopiperazine Intermediate

The following is a procedure for preparing the 2,5-substituted 3-ketopiperazine scaffold intermediate having the formula:

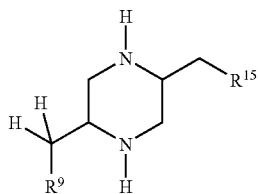

wherein for the following example $R^9$ is 2-naphthyl, and $R^{15}$ is 1-benzyl-1H-imidazol-4-yl.

3-(1-Benzyl-1H-imidazol-4-ylmethyl)-6-naphthalen-2-ylmethylpiperazin-2-one (70)

Preparation of [1-(methoxymethylcarbamoyl)-2-naphthalen-2-ylethyl]carbamic acid tert-butyl ester (67): 2-N-Boc-amino-3-naphthalen-2-yl propionic acid (2.0 g, 6.3 mmol), O,N-dimethoxy-hydroxylamine hydrochloride (0.61 g, 6.6 mmol), hydroxybenzotriazole (1.2 g, 9.4 mmol), and N-methylmorpholine (2 mL, 18.9 mmol) in DMF (15 mL) is cooled to 0° C. and 1-(3-dimethylaminopropyl)-3-ethylcarbodiimide (1.8 g, 9.4 mmol) is slowly added. The resulting mixture is stirred for 2 hours at 0° C. then allowed to warm and stir at room temperature 18 hours. The reaction solution is diluted with water and the resulting solid is collected by filtration, re-dissolved in EtOAc and extracted concentrated in vacuo to afford an oily residue which is purified over silica gel to afford 2.0 g (88%) of a white solid.

Preparation of (1-formyl-2-naphthalen-2-ylethyl)carbamic acid tert-butyl ester (68): To a solution of [1-(methoxymethylcarbamoyl)-2-naphthalen-2-ylethyl]carbamic acid tert-butyl ester, 67, (5.0 g, 13.4 mmol) in THF (40 mL) at −30° C. to −25° C. is added LAH (16.7 mL of a 1M solution in THF) over about 10 minutes and the reaction is then cooled to −55° C. and the stirring is continued for 3 hours. After cooling to −60° C., the reaction is quenched by the addition of citric acid in methanol (1:1 by weight). During quenching the temperature is maintained at about −45° C. The mixture is then allowed to warm to room temperature and partitioned between EtOAc and water and the water phase extracted again with EtOAc. The organic phases are combined and washed with sat NaCl, dried and concentrated in vacuo to afford the crude aldehyde as a white solid which is used without further purification.

Preparation of 3-(1-benzyl-1H-imidazol-4-yl)-2-(2-N-Boc-amino-3-naphthalen-2-ylpropylamino-propionic acid methyl ester (69): The crude aldehyde 1-formyl-2-naphthalen-2-ylethyl)carbamic acid tert-butyl ester, 68, is dissolved in THF (40 mL) and a solution of 2-amino-3-(1-benzyl-1H-imidazol-4-yl)propionic acid methyl ester hydrochloride (4.6 g, 13.9 mmol) in DMF (40 mL) is added. The solution is cooled to 0° C. and sodium triacetoxyborohydride (5.9 g, 27.8 mmol) is added. The suspension as stirred at 0° C. and allowed to warm over 2 hours to room temperature then stirred 18 hours. A saturated aqueous solution of sodium bicarbonate is added until the evolution of gas stops. The solution is extracted with diethyl ether, dried and concentrated to afford the crude product which is purified over silica gel to afford 4.6 g of a yellow oil.

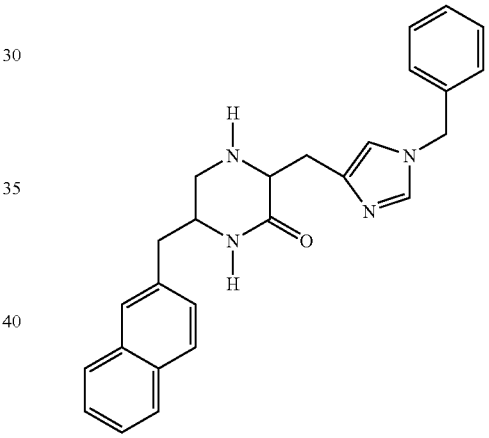

Preparation of 3-(1-benzyl-1H-imidazol-4-ylmethyl)-6-naphthalen-2-ylmethylpiperazin-2-one (70): 3-(1-benzyl-1H-imidazol-4-yl)-2-(2-N-Boc-amino-3-naphthalen-2-yl-propylamino-propionic acid methyl ester, 69, (4.6 g, 8.5 mmol) is dissolved in trifluoroacetic acid/dichloromethane (1:1) (20 mL) and allowed to stir one hour at room temperature. The solution is concentrated in vacuo to an oil which is taken up in diethyl ether several times and concentrated in vacuo to remove all traces of trifluoroacetic acid. The resulting oil is dissolved in ethanol (35 mL) and refluxed for 3 hours. The solvent is removed in vacuo to afford the desired product.

EXAMPLE 11

2-Acetylamino-N-{1-(4-fluorobenzyl)-2-[2-(1H-imidazol-4-ylmethyl)-5-naphthalen-2-ylmethyl-3-oxo-piperazin-1-yl]-2-oxo-ethyl}-3-(4-hydroxyphenyl)propionamide (74)

Preparation of [2-[2-(1-benzyl-1H-imidazol-4-ylmethyl)-5-naphthalen-2-ylmethyl-3-oxo-piperazin-1-yl]-1-(4-fluorobenzyl)-2-oxo-ethyl]carbamic acid tert-butyl ester (71): To a solution of 3-(1-benzyl-1H-imidazol-4-ylmethyl)-6-naphthalen-2-ylmethyl-piperazin-2-one, 70, (1.63 g, 4 mmol), (R)-2-N-(tert-butoxycarbonyl)amino-3-(4-fluorophenyl)propanoic acid (1.4 g, 4.8 mmol), 1-hydroxybenzotriazole (0.6 g, 4.4 mmol), and N-methylmorpholine (1.3 mL, 12.0 mmol) in DMF (15 mL) is cooled to 0° C. and 1-(3-dimethylaminopropyl)-3-ethylcarbodiimide (1.2 g, 6 mmol) is slowly added. The resulting mixture is stirred for 2 hours at 0° C. then allowed to warm and stir at room temperature another 18 hours. The reaction solution is diluted with water and the solution extracted with EtOAc. The organic layers are combined, dried, concentrated in vacuo to afford a sticky orange solid which is purified over silica gel (EtOAc/MeOH 9:1) to yield 1.2 g of a white solid.

Preparation of 4-[2-amino-3-(4-fluorophenyl)propionyl]-3-(1-benzyl-1H-imidazol-4-ylmethyl)-6-naphthalen-2-ylmethylpiperiazin-2-one (72): [2-[2-(1-benzyl-1H-imidazol-4-ylmethyl)-5-naphthalen-2-ylmethyl-3-oxo-piperazin-1-yl]-1-(4-fluorobenzyl)-2-oxo-ethyl]carbamic acid tert-butyl ester, 71, (30 mg, 0.044 mmol) is dissolved in trifluoroacetic acid/dichloromethane (0.5 mL). After one hour the solution is concentrated in vacuo and the residue purified by reverse phase $C_{18}$ prep HPLC to afford 25 mg of a white solid.

Preparation of 2-acetylamino-N-[2-[2-(1-benzyl-1H-imidazol-4-ylmethyl)-5-naphthalen-2-ylmethyl-3-oxo-piperazin-1-yl]-1-(4-fluorobenzyl)-2-oxo-ethyl]-3-(4-hydroxyphenyl)propionamide (73): To a solution of 4-[2-amino-3-(4-fluorophenyl)propionyl]-3-(1-benzyl-1H-imidazol-4-ylmethyl)-6-naphthalen-2-ylmethylpiperiazin-2-one, 72, (0.415 g, 0.615 mmol), N-acetyl-L-tyrosine (0.140 g, 0.615 mmol), 1-hydroxybenzotriazole (0.125 g, 0.922 mmol), and N-methylmorpholine (0.2 mL, 12.0 mmol) in DMF (4 mL) is cooled to 0° C. and 1-(3-dimethylaminopropyl)-3-ethylcarbodiimide (0.235 g, 1.23 mmol) is slowly added. The resulting mixture is stirred for 2 hours at 0° C. then allowed to warm and stir at room temperature another 18 hours. The reaction solution is diluted with water and the solution extracted with EtOAc. The organic layers are combined, dried, concentrated in vacuo and purified by reverse phase $C_{18}$ prep HPLC to afford 0.22 g of a brown-white solid.

Preparation of 2-acetylamino-N-{1-(4-fluorobenzyl)-2-[2-(1H-imidazol-4-ylmethyl)-5-naphthalen-2-ylmethyl-3-oxo-piperazin-1-yl]-2-oxo-ethyl]-3-(4-hydroxyphenyl)propionamide (74): 2-acetylamino-N-[2-[2-(1-benzyl-1H-imidazol-4-ylmethyl)-5-naphthalen-2-ylmethyl-3-oxo-piperazin-1-yl]-1-(4-fluorobenzyl)-2-oxo-ethyl]-3-(4-hydroxyphenyl)propionamide, 73, (0.22 g, 0.28 mmol) is dissolved in ethanol/acetic acid (4:1) (3 mL). Cyclohexene (3 mL) and Pd-black are added and the solution is refluxed with periodic replenishment of cyclohexene. The reaction is monitored by TLC and after 2 days is cooled and filtered through Celite to remove the catalyst. The filtrate is concentrated in vacuo to afford an oil which is purified by reverse phase $C_{18}$ prep HPLC to afford the desired product.

Another aspect of the present invention relates to analogs wherein at least two of $R^2$, $R^3$, and $R^4$ are taken together to form a ring, for example, receptor ligands having the formula:

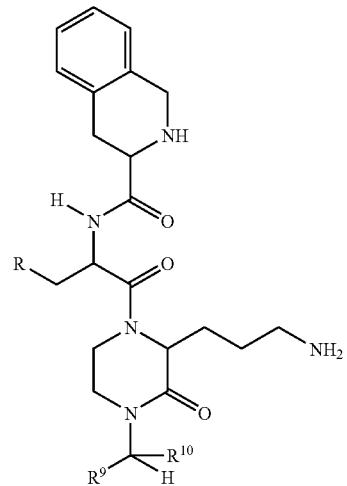

wherein R, $R^9$ and $R^{10}$ are defined in Table XII.

TABLE XII

| No. | R | $R^9$ | $R^{10}$ |
|---|---|---|---|
| 657 | phenyl | H | benzyl |
| 658 | 4-fluorophenyl | H | benzyl |
| 659 | 3,4-difluorophenyl | H | benzyl |
| 660 | 4-chlorophenyl | H | benzyl |
| 661 | 4-methyl | H | benzyl |
| 662 | 4-methoxy | H | benzyl |
| 663 | naphthyl | H | benzyl |
| 664 | phenyl | —CO$_2$CH$_3$ | benzyl |
| 665 | 4-fluorophenyl | —CO$_2$CH$_3$ | benzyl |
| 666 | 3,4-difluorophenyl | —CO$_2$CH$_3$ | benzyl |
| 667 | 4-chlorophenyl | —CO$_2$CH$_3$ | benzyl |
| 668 | 4-methyl | —CO$_2$CH$_3$ | benzyl |
| 669 | 4-methoxy | —CO$_2$CH$_3$ | benzyl |
| 670 | naphthyl | —CO$_2$CH$_3$ | benzyl |
| 671 | phenyl | —CONH$_2$ | benzyl |
| 672 | 4-fluorophenyl | —CONH$_2$ | benzyl |
| 673 | 3,4-difluorophenyl | —CONH$_2$ | benzyl |
| 674 | 4-chlorophenyl | —CONH$_2$ | benzyl |
| 675 | 4-methyl | —CONH$_2$ | benzyl |
| 676 | 4-methoxy | —CONH$_2$ | benzyl |
| 677 | naphthyl | —CONH$_2$ | benzyl |
| 678 | phenyl | —CONHCH$_3$ | benzyl |
| 679 | 4-fluorophenyl | —CONHCH$_3$ | benzyl |
| 680 | 3,4-difluorophenyl | —CONHCH$_3$ | benzyl |
| 681 | 4-chlorophenyl | —CONHCH$_3$ | benzyl |
| 682 | 4-methyl | —CONHCH$_3$ | benzyl |
| 683 | 4-methoxy | —CONHCH$_3$ | benzyl |
| 684 | naphthyl | —CONHCH$_3$ | benzyl |
| 685 | phenyl | H | 2-naphthylmethyl |
| 686 | 4-fluorophenyl | H | 2-naphthylmethyl |
| 687 | 3,4-difluorophenyl | H | 2-naphthylmethyl |
| 688 | 4-chlorophenyl | H | 2-naphthylmethyl |
| 689 | 4-methyl | H | 2-naphthylmethyl |
| 690 | 4-methoxy | H | 2-naphthylmethyl |
| 691 | naphthyl | H | 2-naphthylmethyl |
| 692 | phenyl | —CO$_2$CH$_3$ | 2-naphthylmethyl |
| 693 | 4-fluorophenyl | —CO$_2$CH$_3$ | 2-naphthylmethyl |
| 694 | 3,4-difluorophenyl | —CO$_2$CH$_3$ | 2-naphthylmethyl |
| 695 | 4-chlorophenyl | —CO$_2$CH$_3$ | 2-naphthylmethyl |
| 696 | 4-methyl | —CO$_2$CH$_3$ | 2-naphthylmethyl |
| 697 | 4-methoxy | —CO$_2$CH$_3$ | 2-naphthylmethyl |
| 698 | naphthyl | —CO$_2$CH$_3$ | 2-naphthylmethyl |
| 699 | phenyl | —CONH$_2$ | 2-naphthylmethyl |
| 700 | 4-fluorophenyl | —CONH$_2$ | 2-naphthylmethyl |
| 701 | 3,4-difluorophenyl | —CONH$_2$ | 2-naphthylmethyl |
| 702 | 4-chlorophenyl | —CONH$_2$ | 2-naphthylmethyl |
| 703 | 4-methyl | —CONH$_2$ | 2-naphthylmethyl |
| 704 | 4-methoxy | —CONH$_2$ | 2-naphthylmethyl |

TABLE XII-continued

| No. | R | $R^9$ | $R^{10}$ |
|---|---|---|---|
| 705 | naphthyl | —CONH$_2$ | 2-naphthylmethyl |
| 706 | phenyl | —CONHCH$_3$ | 2-naphthylmethyl |
| 707 | 4-fluorophenyl | —CONHCH$_3$ | 2-naphthylmethyl |
| 708 | 3,4-difluorophenyl | —CONHCH$_3$ | 2-naphthylmethyl |
| 709 | 4-chlorophenyl | —CONHCH$_3$ | 2-naphthylmethyl |
| 710 | 4-methyl | —CONHCH$_3$ | 2-naphthylmethyl |
| 711 | 4-methoxy | —CONHCH$_3$ | 2-naphthylmethyl |
| 712 | naphthyl | —CONHCH$_3$ | 2-naphthylmethyl |

The following is an outline of a synthetic pathway for preparing analogs 657–663 and 685–691, however, other embodiments and iterations of the 3-ketopiperazine scaffold can be prepared using modification to this general procedure.

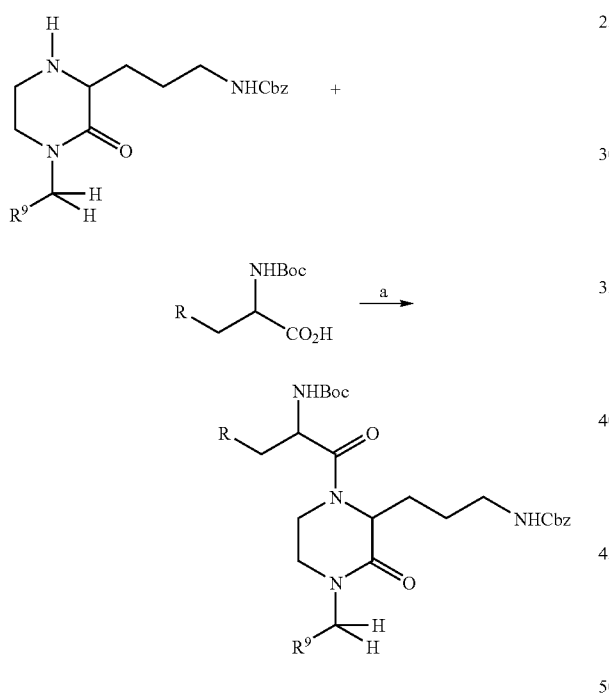

Reagents and conditions: (a) HOBt, EDCI, N-methylmorpholine, DMF, 0° C.

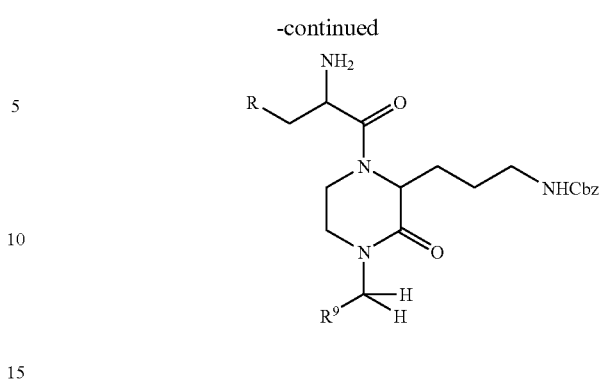

Reagents and conditions: (b) TFA/CH$_2$Cl$_2$, rt.

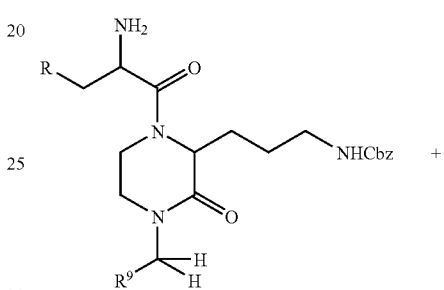

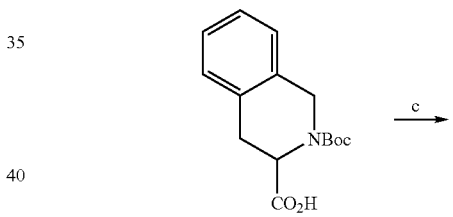

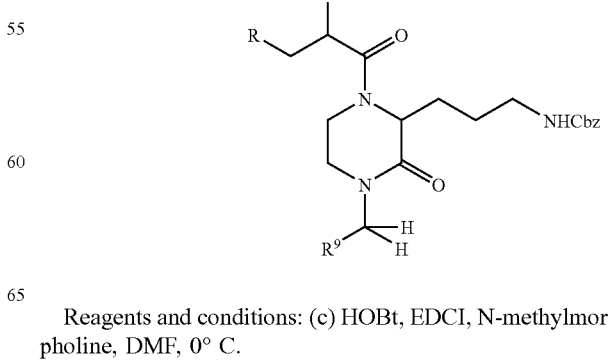

Reagents and conditions: (c) HOBt, EDCI, N-methylmorpholine, DMF, 0° C.

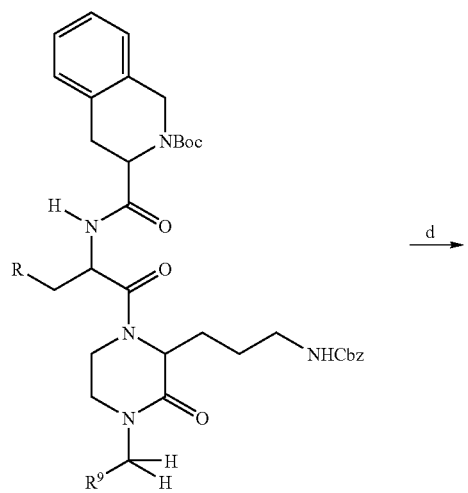

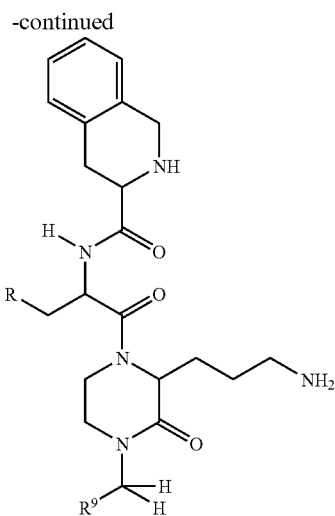

Reagents and conditions: (e) H$_2$, 10% Pd/C; MeOH.

Preparation of 3-Ketopiperazine Intermediate

The following is a procedure for preparing the 3-ketopiperazine intermediate having the formula:

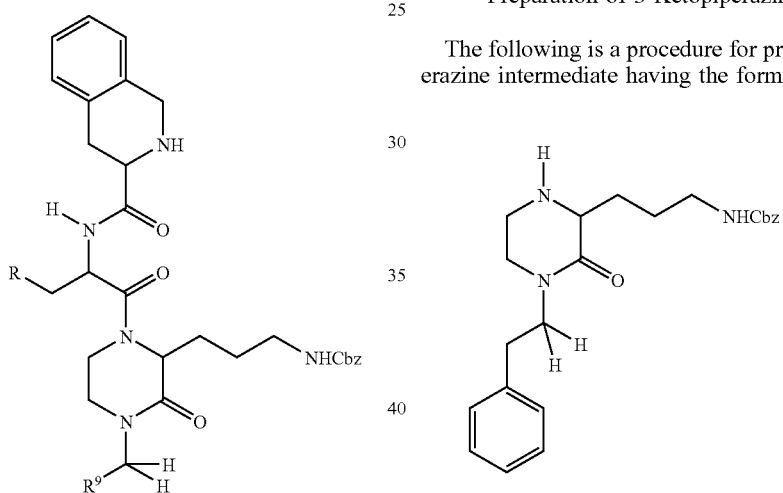

wherein for this example R$^9$ is benzyl.

[3-(3-Oxo-4-phenethylpiperazin-2-yl)propyl]-carbamic acid benzyl ester (76)

Preparation of (4-N-Cbz-amino-1-phenethylcarbamoyl-butyl)carbamic acid tert-butyl ester (75): A solution of phenethylamine (12.1 g, 100 mmol), 5-benzyloxycarbony-lamino-2-tert-butoxycarbonylamino-pentanoic acid (33.6 g, 100 mmol), hydroxybenzotriazole (16.2 g, 120 mmol), and N-methylmorpholine (132 mL, 120 mmol) in DMF (150 mL) is cooled to 0° C. and 1-(3-dimethylaminoopropyl)-3-ethylcarbodiimide (24.9 g, 130 mmol) is slowly added. The resulting mixture is stirred for 2 hours at 0° C. then allowed to warm and stir at room temperature another 2 hours. The reaction solution is diluted with water and the resulting solid is collected by filtration, re-dissolved in EtOAc and extracted with water, dried and concentrated in vacuo to afford a residue which purified over silica gel.

Preparation of (4-amino-4-phenetylcarbamoylbutyl)car-bamic acid benzyl ester (76): (4-N-Cbz-amino-1-phenethyl-carbamoylbutyl)carbamic acid tert-butyl ester, 75, (47.0 g, 100 mmol) is dissolved in 300 ml of a solution prepared Reagents and conditions: (b) TFA/CH$_2$Cl$_2$, rt.

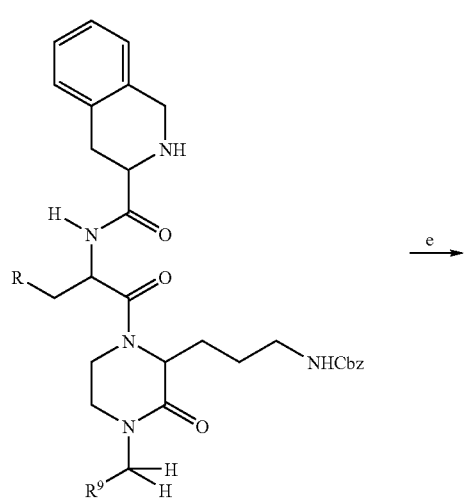

from 2:1:0.1 parts of dichloromethane TFA and water. The reaction mixture is stirred for 3 hours. The solvent is removed in vacuo and the residue treated with 1,2-dichloromethane which is also removed in vacuo. This is repeated several times and affords the crude rude residue which is used for the next step without further purification.

Preparation of [3-(3-Oxo-4-phenethylpiperazin-2-yl)propyl]-carbamic acid benzyl ester (77): A mixture of 4-amino-4-phenetylcarbamoylbutyl) carbamic acid benzyl ester, 76, (36.9 g, 100 mmol), dibromoethane (12.9 mL, 4.36 mmol), potassium carbonate (69 g, 500 mmol) in DMF (500 ml) is stirred at 55° C. for 18 hours. The reaction mixture is cooled to room temperature, treated with 1 M KHSO$_4$ and the resulting solution is extracted with ethyl acetate. The crude product is purified over silica (sequential elution with EtOAc/hexanes mixtures 1:2, 1:1, 100% EtOAc, then EtOAc with 5% MeOH) to afford the desired product.

EXAMPLE 12

2-(3-(3-Aminopropyl)-4-{3-(4-fluorophenyl)-2-[(1,2,3,4-tetrahydroioquinolin-3-carbonyl)amino]propionyl}-2-oxo-piperazin-1-yl)-3-naphthalen-2-yl propionic acid methyl ester (82)

Preparation of (3-{1-[2-N-Boc-amino-3-(4-fluorophenyl)propionyl]-3-oxo-4-phenethylpiperizin-2-yl}propyl)-carbamic acid benzyl ester (78): To a solution of [3-(3-Oxo-4-phenethyl-piperazin-2-yl)propyl]-carbamic acid benzyl ester, 77, (3.95 g, 10 mmol), (R)-2-N-(tert-butoxycarbonyl)amino-3-(4-fluorophenyl)propanoic acid (3.40 g, 12 mmol), 1-hydroxybenzotriazole (1.62 g, 12 mmol), and N-methylmorpholine (13 mL, 12 mmol) in DMF (15 mL) is cooled to 0° C. and 1-(3-dimethylaminopropyl)-3-ethylcarbodiimide (2.49 g, 13 mmol) is slowly added. The resulting mixture is stirred for 2 hours at 0° C. then allowed to warm and stir at room temperature another 2 hours. The reaction solution is diluted with water and the resulting solution extracted with EtOAc, dried and concentrated in vacuo to afford the desired product.

Preparation of (3-{1-[2-amino-3-(4-fluorophenyl)propionyl]-3-oxo-4-phenethyl-piperazin-2-yl}propyl)-carbamic acid benzyl ester (79): A solution of(3-{1-[2-N-Boc-amino-3-(4-fluorophenyll)propionyl]-3-oxo-4-phenethylpiperizin-2-yl}propyl)-carbamic acid benzyl ester, 78, (6.6 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Preparation of 3-[2-[2-(3-N-Cbz-aminopropyl)-3-oxo-4-phenethylpiperazin-1-yl]-1-(4-fluorobenzyl)-2-oxo-ethylcarbamoyl]-3,4-dihydro-1H-isoquinoline-2-carboxylic acid tert-butyl ester (80): A solution of (3-{1-[2-amino-3-(4-fluorophenyl)propionyl]-3-oxo-4-phenethyl-piperazin-2-yl}propyl)-carbamic acid benzyl ester, 79, (5.6 g, 10 mmol), N-Boc-1,2,3,4-tetrahydroisoquinoline-3-carboxylic acid (3.8 g, 10 mmole), hydroxybenzotriazole (1.62 g, 12 mmol), and N-methylmorpholine (13 mL, 12 mmol) in DMF (50 mL) is cooled to 0° C. and 1-(3-dimethylaminopropyl)-3-ethylcarbodiimide (2.49 g, 13 mmol) is slowly added. The resulting mixture is stirred for 2 hours at 0° C. then allowed to warm and stir at room temperature another 2 hours. The reaction solution is diluted with water and the resulting solution extracted with EtOAc, dried and concentrated in vacuo to afford the crude product which is purified over silica gel.

Preparation of [3-(1-{3-(4-fluorophenyl)-2-[(1,2,3,4-tetrahydroisoquinolin-3-carbonyl)amino]propionyl}-3-oxo-4-phenethylpiperazin-2-yl)propyl]carbamic acid benzyl ester (81): A solution of 3-[2-[2-(3-N-Cbz-aminopropyl)-3-oxo-4-phenethylpiperazin-1-yl]-1-(4-fluorobenzyl)-2-oxo-ethylcarbamoyl]-3,4-dihydro-1H-isoquinoline-2-carboxylic acid tert-butyl ester, 80, (8.2 g, 10 mmol), trifluoroacetic acid (5 mL), and dichloromethane (50 mL) is stirred at room temperature for 2 hours and then concentrated in vacuo. The crude product is dissolved in dichloromethane and the organic layer washed with saturated sodium bicarbonate, dried, and concentrated in vacuo to afford the desired product.

Preparation of 2-(3-(3-Aminopropyl)-4-{3-(4-fluorophenyl)-2-[(1,2,3,4-tetrahydroioquinolin-3-carbonyl)amino]propionyl}-2-oxo-piperazin-1-yl)-3-naphthalen-2-yl propionic acid methyl ester (82): A solution of [3-(1-{3-(4-fluorophenyl)-2-[(1,2,3,4-tetrahydroisoquinolin-3-carbonyl)amino]propionyl}-3-oxo-4-phenethylpiperazin-2-yl)propyl]carbamic acid benzyl ester, 81, (7.2 g, 10 mmol) is suspended in methanol (100 ml) and hydrogenated in the presence of 10% Pd/C at 40 psi for 24 hours. The solution is filtered to remove the catalyst and the crude product is purified on a preparative HPLC using a linear gradient of acetonitrile in water with 0.1% TFA to afford the desired product.

The present invention further relates to methods for treating one or more disease states. One aspect of the present invention relates to a method for treating a disorder selected from the group consisting of insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease, in an animal subject in need thereof, said method comprising the step of administering to said subject a compound as described herein above.

Another aspect of the present invention relates to methods for treating one or more disorders selected from the group consisting of a body weight disorder, CNS depression, behavior-related disorders, memory related disorders, cardiovascular function, inflammation, sepsis, septic shock, cardiogenic shock, hypovolemic shock, sexual dysfunction, erectile dysfunction, muscle atrophy, diseases associated with nerve growth and repair, and intrauterine fetal growth, in an animal subject in need thereof, said method comprising the step of administering to said subject a compound as described herein above.

One particular embodiment of the present invention is directed to a method for controlling a body weight disorder selected from the group consisting of obesity, anorexia and cachexia.

Melanocortin Functional Activity and Selectivity

Functional activity can be evaluated using various methods known in the art. Examples of such methods are measurement of second messenger responses, in particular cAMP, the use of modified cell systems yielding color reaction upon accumulation of second messenger elements such as cAMP, e.g. as described by Chen et al. 1995 (*Anal Biochem.* 1995, 226, 349–54), Cytosensor Microphysiometer techniques (see Boyfield et al. 1996), or the study of physiological effects caused by the compounds of the invention may be applied by using the compounds of the invention alone, or in combination with natural or synthetic MSH-peptides.

The compounds of the present invention will interact preferentially (i.e., selectively) to MC-4 and/or MC-3, relative to the other melanocortin receptors. Selectivity is particularly important when the compounds are administered to humans or other animals, to minimize the number of side effects associated with their administration. MC-3/MC-4 selectivity of a compound is defined herein as the ratio of the $EC_{50}$ of the compound for an MC-1 receptor ("$EC_{50}$-MC-1") over the $EC_{50}$ of the compound for the MC-3 ($EC_{50}$-MC-3)/MC-4 ($EC_{50}$-MC-4) receptor, the $EC_{50}$ values being measured as described above. The formulas are as follows:

MC-3 selectivity=[$EC_{50}$-MC-1]/[$EC_{50}$-MC-3]

MC-4 selectivity=[$EC_{50}$-MC-1]/[$EC_{50}$-MC-4]

A compound is defined herein as being "selective for the MC-3 receptor" when the above mentioned ratio "MC-3-selectivity" is at least about 10, preferably at least about 100, and more preferably at least about 500.

A compound is defined herein as being "selective for the MC-4 receptor" when the above mentioned ratio "MC-4-selectivity" is at least about 10, preferably at least about 100, and more preferably at least about 500.

Methods of Use and Compositions:

The present invention further relates to compositions which comprise the herein above described receptor ligands.

For example the present invention relates to a pharmaceutical composition comprising:

a) an effective amount of a compound, or one or more of the pharmaceutically acceptable salts thereof, and b) the balance pharmaceutically-acceptable carriers, excipients, and adjunct ingredients.

A "safe and effective amount" of a compound according to the present invention is an amount that is effective to interact with the MC-4 and/or MC-3 receptor, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the excipient employed, the solubility of the Formula (I) compound therein, and the dosage regimen desired for the composition.

In addition to the subject compound, the compositions of the subject invention contain one or more pharmaceutically-acceptable excipients. The term "pharmaceutically-acceptable excipient", as used herein, means one or more compatible solid or liquid ingredients which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable excipients must, of course, be of sufficiently high purity and sufficiently low toxicity to render them suitable for administration to the animal, preferably a mammal, more preferably a human being treated.

Some examples of substances which can serve as pharmaceutically-acceptable excipients or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; wetting agents and lubricants, such as sodium lauryl sulfate; coloring agents; flavoring agents; tableting agents, stabilizers; antioxidants; preservatives; pyrogen-free water; isotonic saline; and buffers, such as phosphate, citrate and acetate.

The choice of pharmaceutically-acceptable excipients to be used in conjunction with the subject compound is basically determined by the way the compound is to be administered. If the subject compound is to be injected, the preferred pharmaceutically-acceptable excipient is sterile water, physiological saline, or mixtures thereof, the pH of which has preferably been adjusted to about 4–10 with a pharmaceutical buffer; a compatible suspending agent may also be desirable.

In particular, pharmaceutically-acceptable excipients for systemic administration include sugars, starches, cellulose and its derivatives, malt, gelatin, talc, calcium sulfate, lactose, vegetable oils, synthetic oils, polyols, alginic acid, phosphate, acetate and citrate buffer solutions, emulsifiers, isotonic saline, and pyrogen-free water. Preferred excipients for parenteral administration include propylene glycol, ethyl oleate, pyrrolidone, ethanol, and sesame oil. Preferably, the pharmaceutically-acceptable excipient, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 1 mg to about 750 mg, more preferably from about 3 mg to about 500 mg, still more preferably from about 5 mg to about 300 mg, of a Formula (I) compound.

Based on their ability to agonize or antagonize the MC-4 and/or MC-3 receptor, the present invention also relates to the use of the ligands described herein in methods for treating obesity and other body weight disorders, including, for example, anorexia and cachexia. The compounds may also be used in methods for treating disorders that result from body weight disorders, including but not limited to insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease. The invention further relates to the treatment of disorders relating to behavior, memory (including learning), cardiovascular function, inflammation, sepsis, cardiogenic and hypovolemic shock, sexual dysfunction, penile erection, muscle atrophy, nerve growth and repair, intrauterine fetal growth, and the like.

The terms treating and treatment are used herein to mean that, at a minimum, administration of a compound of the present invention mitigates a disorder by acting via the MC-3 or MC-4 receptor. Thus, the terms include: preventing a disease state from occurring in a mammal, particularly when the mammal is predisposed to acquiring the disease, but has not yet been diagnosed with the disease; inhibiting progression of the disease state; and/or alleviating or reversing the disease state.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition and *Peptide and Protein Drug Delivery*, Marcel Dekker, NY, 1991.

The compositions of this invention may be in any of a variety of forms, suitable (for example) for oral, rectal, topical, nasal, ocular, transdermal, pulmonary or parenteral administration. Depending upon the particular route of administration desired, a variety of pharmaceutically-acceptable excipients well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of excipient employed in conjunction with the Formula (I) compound is sufficient to provide a practical quantity of material for administration per unit dose of the compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable excipient suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin, polyvinylpyrrolidone and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of excipient components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable excipients suitable for preparation of such compositions are well known in the art. Typical components of excipients for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben, propyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Because the compounds of the present invention are peptidic in nature, a preferred mode of administration is parenteral (more preferably intravenous injection) or nasal administration, in the form of a unit dose form. Preferred unit dose forms include suspensions and solutions, comprising a safe and effective amount of a Formula I compound. When administered parenterally, the unit dose form will typically comprise from about 1 mg to about 3 g, more typically from about 10 mg to about 1 g, of the Formula (I) compound, although the amount of compound administered will depend, for example, on its relative affinity for the MC-4/MC-3 receptor subtypes, its selectivity over other receptors, including the other melanocortin receptors, etc.

Compositions of the subject invention may optionally include other drug actives.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Methods of Administration:

As indicated, compositions of this invention can be administered topically or systemically. Systemic application includes any method of introducing a Formula (I) compound into the tissues of the body, e.g., intra-articular, intrathecal, epidural, intramuscular, transdermal, intravenous, intraperitoneal, subcutaneous, sublingual, rectal, nasal, pulmonary, and oral administration. The Formula (I) compounds of the present invention are preferably administered systemically, more preferably parenterally and most preferably via intravenous injection.

The specific dosage of compound to be administered, as well as the duration of treatment, and whether the treatment is topical or systemic are interdependent. The dosage and treatment regimen will also depend upon such factors as the specific Formula (I) compound used, the treatment indication, the personal attributes of the subject (such as weight), compliance with the treatment regimen, and the presence and severity of any side effects of the treatment.

Typically, for a human adult weighing approximately 70 kilograms, from about 1 mg to about 6 g, more typically from about 100 mg to about 3 g, of Formula (I) compound are administered per day for systemic administration. It is understood that these dosage ranges are by way of example only, and that daily administration can be adjusted depending on the factors listed above.

As is known and practiced in the art, all formulations for parenteral administration must be sterile. For mammals, especially humans, (assuming an approximate body weight of 70 kilograms) individual doses of from about 0.001 mg to about 100 mg are preferred.

A preferred method of systemic administration is intravenous delivery. Individual doses of from about 0.01 mg to about 100 mg, preferably from about 0.1 mg to about 100 mg are preferred when using this mode of delivery.

In all of the foregoing, of course, the compounds of the invention can be administered alone or as mixtures, and the compositions may further include additional drugs or excipients as appropriate for the indication.

The compound of the invention can be delivered to the preferred site in the body by using a suitable drug delivery system. Drug delivery systems are well known in the art. For example, a drug delivery technique useful for the compounds of the present invention is the conjugation of the compound to an active molecule capable of being transported through a biological barrier (see e.g. Zlokovic, B. V., *Pharmaceutical Research*, Vol. 12, pp. 1395–1406 (1995)). A specific example constitutes the coupling of the compound of the invention to fragments of insulin to achieve transport across the blood brain barrier (Fukuta, M., et al. *Pharmaceutical Res.*, Vol. 11, pp. 1681–1688 (1994)). For general reviews of technologies for drug delivery suitable for the compounds of the invention see Zlokovic, B. V., *Pharmaceutical Res.*, Vol. 12, pp. 1395–1406 (1995) and Pardridge, W M, *Pharmacol. Toxicol.*, Vol. 71, pp. 3–10 (1992).

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, including all enatiomeric and diasteriomeric forms and pharmaceutically acceptable salts thereof, said compound having the formula:

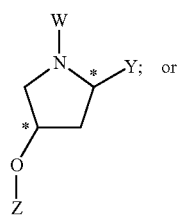

a)

or

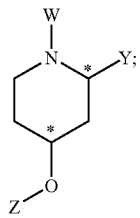

b)

-continued wherein the carbon atoms marked with an asterisk can have any stereochemical configuration;

W has the formula:

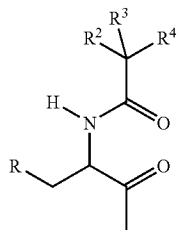

R is phenyl or substituted phenyl;

wherein $R^2$, $R^3$, and $R^4$ units are independently selected from the group:
a) rings consisting of:
   i) substituted or unsubstituted aromatic carbocyclic rings, said rings selected from phenyl, benzyl, α-naphthyl, or β-naphthyl;
   ii) substituted or unsubstituted aromatic heterocyclic rings, said rings selected from 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-imidazolylmethyl, 2-imidazolylmethyl, 4-imidazolylmethyl, 1-pyridinyl, 2-pyridinyl, 3-pyridinyl, or 4-pyridinyl;
   iii) and mixtures thereof;
b) hydrogen;
c) a unit selected from the group consisting of —CH$_2$C(O)CH$_3$, —NHC(O)CH$_3$, —NHC(O)CH$_2$CH$_3$, and —NHC(O)CH$_2$CH$_2$CH$_3$;
d) two of $R^2$, $R^3$, or $R^4$ can be taken together to form a ring consisting of:
   i) substituted or unsubstituted aromatic carbocyclic rings, said rings selected from phenyl, α-naphthyl, or β-naphthyl;
   ii) substituted or unsubstituted aromatic heterocyclic rings, said rings selected from 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-pyridinyl, 2-pyridinyl, 3-pyridinyl, or 4-pyridinyl; and
e) mixtures thereof;

Y is a pendant unit containing at least one heteroatom having the formula:

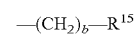

wherein $R^{15}$ is an ester selected from the group consisting of:
i) —C(O)OCH$_3$;
ii) —C(O)OCH$_2$CH$_3$;
iii) —C(O)OCH$_2$CH$_2$CH$_3$;

iv) —C(O)OCH$_2$CH$_2$CH$_2$CH$_3$;
v) —C(O)OCH(CH$_3$)$_2$;
vi) —C(O)OCH$_2$CH(CH$_3$)$_2$;
vii) —C(O)OCH$_2$CH=CHCH$_3$;
viii) —C(O)OCH$_2$CH$_2$CH(CH$_3$)$_2$;
ix) —C(O)OCH$_2$C(CH$_3$)$_3$;
x) —OC(O)CH$_3$;
xi) —OC(O)CH$_2$CH$_3$;
xii) —OC(O)CH$_2$CH$_2$CH$_3$;
xiii) —OC(O)CH(CH$_3$)$_2$;
xiv) —OC(O)CH$_2$CH$_2$CH$_2$CH$_3$;
xv) —OC(O)CH$_2$CH(CH$_3$)$_2$;
xvi) —OC(O)CH$_2$CH=CHCH$_3$;
xvii) —OC(O)CH$_2$C(CH$_3$)$_3$; and
xviii) —OC(O)CH$_2$CH$_2$CH(CH$_3$)$_2$;
an amide selected from the group consisting of:
i) —C(O)NHCH$_3$;
ii) —C(O)NHCH$_2$CH$_3$;
iii) —C(O)NHCH$_2$CH$_2$CH$_3$;
iv) —C(O)NHCH$_2$CH$_2$CH$_2$CH$_3$;
v) —C(O)NHCH(CH$_3$)$_2$;
vi) —C(O)NHCH$_2$CH(CH$_3$)$_2$;
vii) —C(O)NHCH$_2$CH=CHCH$_3$;
viii) —C(O)NHCH$_2$CH$_2$CH(CH$_3$)$_2$;
ix) —C(O)NHCH$_2$C(CH$_3$)$_3$;
x) —NHC(O)CH$_3$;
xi) —NHC(O)CH$_2$CH$_3$;
xii) —NHC(O)CH$_2$CH$_2$CH$_3$;
xiii) —NHC(O)CH(CH$_3$)$_2$;
xiv) —NHC(O)CH$_2$CH$_2$CH$_2$CH$_3$;
xv) —NHC(O)CH$_2$CH(CH$_3$)$_2$;
xvi) —NHC(O)CH$_2$CH=CHCH$_3$;
xvii) —NHC(O)CH$_2$C(CH$_3$)$_3$; and
xviii) —NHC(O)CH$_2$CH$_2$CH(CH$_3$)$_2$; or
a unit selected from the group consisting of:
a) —C(X)N(R$^{16}$)$_2$;
b) —C(X)NR$^{16}$N(R$^{16}$)$_2$;
c) —NR$^{16}$C(X)N(R$^{16}$)$_2$; and
d) —NHN(R$^{16}$)$_2$;
wherein X is =O, =S, or =NR$^{16}$, R$^{16}$ is hydrogen, methyl, cyano, hydroxy, and nitro:
the index b is from 1 to 4;
Z is a pendant unit, which contains an aromatic carbocyclic ring; said unit having the formula:

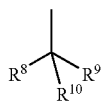

wherein R$^8$ is hydrogen; R$^9$ is phenyl, benzyl, 1-naphthyl, 2-naphthyl, 1-naphthylmethyl, 2-naphthylmethyl; R$^{10}$ is hydrogen, —C(X)$_2$R$^{17}$, —C(X)N(R$^{16}$)$_2$, —N(R$^{16}$)$_2$ and —NR$^{16}$C(X)R$^{17}$; R$^{16}$ is hydrogen, or C$_1$–C$_{10}$ alkyl; R$^{17}$ is C$_1$–C$_{16}$ linear or branched, substituted or unsubstituted alkyl, C$_7$–C$_{16}$ linear or branched, substituted or unsubstituted alkylenearyl; X is oxygen, sulfur, and =NR$^{16}$.

2. A compound according to claim 1 wherein R is selected from the group consisting of phenyl, benzyl, 3-fluorophenyl, 4-fluorophenyl, 3,5-difluorophenyl, 4-chlorophenyl, and 4-hydroxyphenyl.

3. A compound according to claim 1 wherein W has the formula:

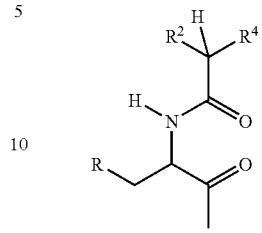

R$^2$ is a unit selected from the group consisting of —CH$_2$C(O)CH$_3$, —NHC(O)CH$_3$, —NHC(O)CH$_2$CH$_3$, and —NHC(O)CH$_2$CH$_2$CH$_3$; R$^4$ units are selected from the group:
a) rings consisting of:
   i) substituted or unsubstituted aromatic carbocyclic rings, said rings selected from phenyl, benzyl, α-naphthyl, or β-naphthyl;
   ii) substituted or unsubstituted aromatic heterocyclic rings, said rings selected from 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-imidazolylmethyl, 2-imidazolylmethyl, 4-imidazolylmethyl, 1-pyridinyl, 2-pyridinyl, 3-pyridinyl, or 4-pyridinyl.

4. A compound according to claim 3 wherein R$^2$ is —NHC(O)CH$_3$.

5. A compound according to claim 4 wherein R$^4$ is a unit selected from the group consisting of benzyl, 2-imidazolylmethyl, 4-imidazolylmethyl, 4-fluorobenzyl, 4-hydroxybenzyl, and 4-acetoxybenzyl.

6. A compound according to claim 1 wherein W has the formula:

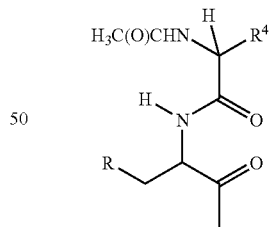

R is selected from the group consisting of phenyl, benzyl, 3-fluorophenyl, 4-fluorophenyl, 3,5-difluorophenyl, 4-chlorophenyl, and 4-hydroxyphenyl; R$^4$ is a unit selected from the group consisting of benzyl, 2-imidazolylmethyl, 4-imidazolylmethyl, 4-fluorobenzyl, 4-hydroxybenzyl, 4-acetoxybenxyl, 2-imidazolylmethyl, 4-imidazolylmethyl, 2-phenylethyl, 1-natphthylmethyl, and 2-naphthylmethyl.

7. A compound according to claim 1 wherein W has the formula:

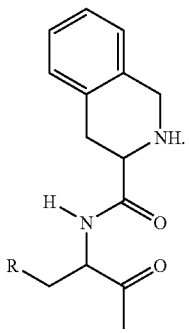

8. A compound according to claim 7 wherein R is selected from the group consisting of phenyl, benzyl, 3-fluorophenyl, 4-fluorophenyl, 3,5-difluorophenyl, 4-chlorophenyl, and 4-hydroxyphenyl.

9. A compound according to claim 1 wherein $R^{15}$ has the formula:

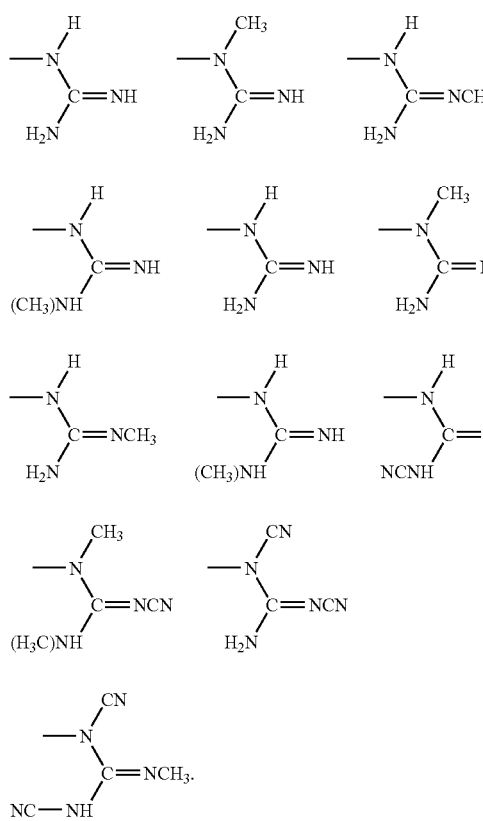

10. A compound according to claim 9 wherein Y has the formula:

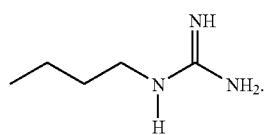

11. A compound according to claim 1 wherein $R^{10}$ is —$CO_2H$, —$CO_2CH_3$, —$CONHCH_3$, and —$CONH_2$.

12. A compound according to claim 11 wherein $R^9$ is benzyl or 2-naphthylmethyl.

13. A compound according to claim 12 wherein $R^9$ is phenyl or 2-naphthyl.

14. A compound according to claim 1 consisting of a scaffold selected from the group consisting of:

i)

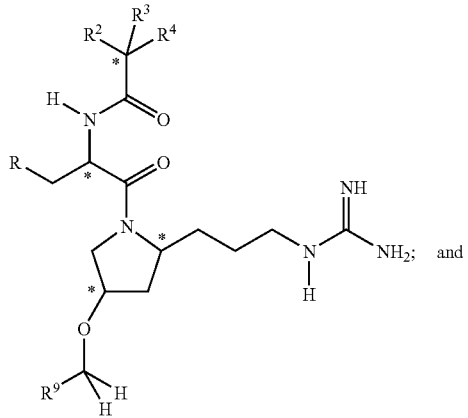

ii)

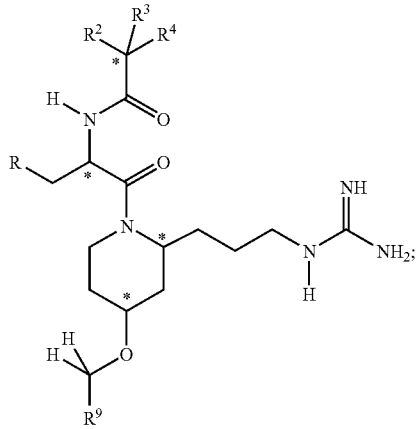

wherein R is selected from the group consisting of phenyl, benzyl, 3-fluorophenyl, 4-fluorophenyl, 3,5-difluorophenyl, 4-chlorophenyl, and 4-hydroxyphenyl; $R^2$ is a unit selected from the group consisting of hydrogen, —$CH_2C(O)CH_3$, —$NHC(O)CH_3$, —$NHC(O)CH_2CH_3$, and —$NHC(O)CH_2CH_2CH_3$; $R^3$ is hydrogen; $R^4$ is a unit selected from the group consisting of benzyl, 2-imidazolylmethyl, 4-imidazolylmethyl, 4-fluorobenzyl, 4-hydroxybenzyl, 4-acetoxybenxyl, 2-imidazolylmethyl, 4-imidazolyl-methyl, 2-phenylethyl, 1-natphthylmethyl, and 2-naphthylmethyl, $R^9$ is phenyl, benzyl, 1-naphthyl, 2-naphthyl, 1-naphthylmethyl, 2-naphthylmethyl; $R^{10}$ is hydrogen, —$CO_2CH_3$, —$CO_2H$; —$CONH_2$; and —$CONHCH_3$.

15. A pharmaceutical composition comprising:
A) an amount of a compound, including all enatiomeric and diastereomeric forms and pharmaceutically acceptable salts thereof, effective in controlling body weight, said compound having the formula:

a)

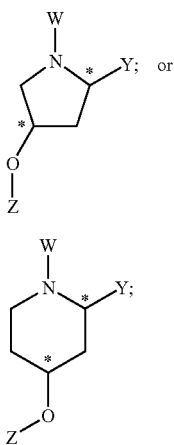

b)

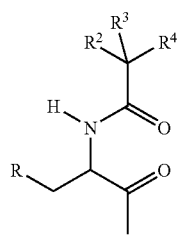

wherein the carbon atoms marked with an asterisk can have any stereochemical configuration;
W has the formula:

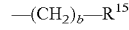

R is phenyl or substituted phenyl;
wherein $R^2$, $R^3$, and $R^4$ units are independently selected from the group:
a) rings consisting of:
   i) substituted or unsubstituted aromatic carbocyclic rings, said rings selected from phenyl, benzyl, α-naphthyl, or β-naphthyl;
   ii) substituted or unsubstituted aromatic heterocyclic rings, said rings selected from 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-imidazolylmethyl, 2-imidazolylmethyl, 4-imidazolylmethyl, 1-pyridinyl, 2-pyridinyl, 3-pyridinyl, or 4-pyridinyl;
   iii) and mixtures thereof;
b) hydrogen;
c) a unit selected from the group consisting of —$CH_2C(O)CH_3$, —$NHC(O)CH_3$, —$NHC(O)CH_2CH_3$, and —$NHC(O)CH_2CH_2CH_3$;
d) two of $R^2$, $R^3$, or $R^4$ can be taken together to form a ring consisting of:
   i) substituted or unsubstituted aromatic carbocyclic rings, said rings selected from phenyl, α-naphthyl, or β-naphthyl;
   ii) substituted or unsubstituted aromatic heterocyclic rings, said rings selected from 1-quinolinyl, 2-quinolinyl, 3-quinolinyl, 4-quinolinyl, 5-quinolinyl, 6-quinolinyl, 7-quinolinyl, 8-quinolinyl, 1-imidazolyl, 2-imidazolyl, 4-imidazolyl, 1-pyridinyl, 2-pyridinyl, 3-pyridinyl, or 4-pyridinyl; and
e) mixtures thereof;
Y is a pendant unit containing at least one heteroatom having the formula:

—$(CH_2)_b$—$R^{15}$ wherein $R^{15}$ is an ester selected from the group consisting of:
i) —$C(O)OCH_3$;
ii) —$C(O)OCH_2CH_3$;
iii) —$C(O)OCH_2CH_2CH_3$;
iv) —$C(O)OCH_2CH_2CH_2CH_3$;
v) —$C(O)OCH(CH_3)_2$;
vi) —$C(O)OCH_2CH(CH_3)_2$;
vii) —$C(O)OCH_2CH=CHCH_3$;
viii) —$C(O)OCH_2CH_2CH(CH_3)_2$;
ix) —$C(O)OCH_2C(CH_3)_3$;
x) —$OC(O)CH_3$;
xi) —$OC(O)CH_2CH_3$;
xii) —$OC(O)CH_2CH_2CH_3$;
xiii) —$OC(O)CH(CH_3)_2$;
xiv) —$OC(O)CH_2CH_2CH_2CH_3$;
xv) —$OC(O)CH_2CH(CH_3)_2$;
xvi) —$OC(O)CH_2CH=CHCH_3$;
xvii) —$OC(O)CH_2C(CH_3)_3$; and
xviii) —$OC(O)CH_2CH_2CH(CH_3)_2$;
an amide selected from the group consisting of:
i) —$C(O)NHCH_3$;
ii) —$C(O)NHCH_2CH_3$;
iii) —$C(O)NHCH_2CH_2CH_3$;
iv) —$C(O)NHCH_2CH_2CH_2CH_3$;
v) —$C(O)NHCH(CH_3)_2$;
vi) —$C(O)NHCH_2CH(CH_3)_2$;
vii) —$C(O)NHCH_2CH=CHCH_3$;
viii) —$C(O)NHCH_2CH_2CH(CH_3)_2$;
ix) —$C(O)NHCH_2C(CH_3)_3$;
x) —$NHC(O)CH_3$;
xi) —$NHC(O)CH_2CH_3$;
xii) —$NHC(O)CH_2CH_2CH_3$;
xiii) —$NHC(O)CH(CH_3)_2$;
xiv) —$NHC(O)CH_2CH_2CH_2CH_3$;
xv) —$NHC(O)CH_2CH(CH_3)_2$;
xvi) —$NHC(O)CH_2CH=CHCH_3$;
xvii) —$NHC(O)CH_2C(CH_3)_3$; and
xviii) —$NHC(O)CH_2CH_2CH(CH_3)_2$; or
a unit selected from the group consisting of:
a) —$C(X)N(R^{16})_2$;
b) —$C(X)NR^{16}N(R^{16})_2$;
c) —$NR^{16}C(X)N(R^{16})_2$; and
d) —$NHN(R^{16})_2$;
wherein X is =O, =S, or =$NR^{16}$, $R^{16}$ is hydrogen, methyl, cyano, hydroxy, and nitro;
the index b is from 1 to 4;
Z is a pendant unit, which contains an aromatic carbocyclic ring; said unit having the formula:

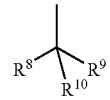

wherein $R^8$ is hydrogen; $R^9$ is phenyl, benzyl, 1-naphthyl, 2-naphthyl, 1-naphthylmethyl, 2-naphthylmethyl; $R^{10}$ is hydrogen, $—C(X)_2R^{17}$, $—C(X)N(R^{16})_2$, $—N(R^{16})_2$ and $—NR^{16}C(X)R^{17}$; $R^{16}$ is hydrogen, or $C_1–C_{10}$ alkyl; $R^{17}$ is $C_1–C_{16}$ linear or branched, substituted or unsubstituted alkyl, $C_7–C_{16}$ linear or branched, substituted or unsubstituted alkylenearyl; X is oxygen, sulfur, and $=NR^{16}$; and B) the balance carriers, excipients, and adjunct ingredients.

\* \* \* \* \*